US012698463B2

(12) United States Patent (10) Patent No.: US 12,698,463 B2
Roth et al. (45) Date of Patent: Aug. 4, 2026

(54) SPATIALLY CONTROLLED FABRICATION OF MULTI-SPHEROID TISSUES USING MAGNETIC BIOPRINTING

(71) Applicant: The Board of Trustees of the Leland Stanford Junior University, Stanford, CA (US)

(72) Inventors: Julien Roth, Redwood City, CA (US); Sungchul Shin, Redwood City, CA (US); Sarah C. Heilshorn, Mountain View, CA (US); Lucia Brunel, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 583 days.

(21) Appl. No.: 18/311,459

(22) Filed: May 3, 2023

(65) Prior Publication Data

US 2023/0357685 A1 Nov. 9, 2023

Related U.S. Application Data

(60) Provisional application No. 63/337,794, filed on May 3, 2022.

(51) Int. Cl.
*C12M 3/00* (2006.01)
*B82Y 5/00* (2011.01)
*C12M 1/32* (2006.01)
*C12N 5/00* (2006.01)
*C12N 13/00* (2006.01)

(52) U.S. Cl.
CPC .............. *C12M 21/08* (2013.01); *B82Y 5/00* (2013.01); *C12M 23/12* (2013.01); *C12N 5/0062* (2013.01); *C12N 13/00* (2013.01); *C12N 2513/00* (2013.01)

(58) Field of Classification Search
None
See application file for complete search history.

(56) References Cited

U.S. PATENT DOCUMENTS

| | | | |
|---|---|---|---|
| 10,961,495 B2 | 3/2021 | Kishii et al. | |
| 11,279,914 B2 | 3/2022 | Andersen et al. | |
| 2019/0127685 A1* | 5/2019 | Abdel Fattah ..... | G01N 33/5032 |
| 2020/0384690 A1 | 12/2020 | Meyers et al. | |
| 2021/0261924 A1 | 8/2021 | Andersen et al. | |

OTHER PUBLICATIONS

Mishriki et al. "Rapid Magnetic 3D Printing of Cellular Structures with MCF-7 Cell Inks" (2019) AAAS Research, art ID 9854593. 1-13 (Year: 2019).*

Ajiteru et al. "A digital light processing 3D printed magnetic Ajiteru et al. "A digital light processing 3D printed magnetic bioreactor system using silk magnetic bioink" (2021), Biofabrication, vol. 13, article No. 034102, 1-18 (Year: 2021).*

Goulart et al. (2019) 3D bioprinting of liver spheroids derived from human induced pluripotent stem cells sustain liver function and viability in vitro. Biofabrication 12, 015010.

Skylar-Scott et al. Biomanufacturing of organ-specific tissues with high cellular density and embedded vascular channels. Science Advances 5, eaaw2459, doi:10.1126/sciadv.aaw2459 (2019).

Ayan et al. Aspiration-assisted bioprinting for precise positioning of biologics. Science Advances 6, eaaw5111, doi:10.1126/sciadv. aaw5111 (2020).

Daly et al. 3D bioprinting of high cell-density heterogeneous tissue models through spheroid fusion within self-healing hydrogels. Nature Communications 12, 753, doi:10.1038/s41467-021-21029-2 (2021).

Ayan et al. Aspiration-assisted freeform bioprinting of pre-fabricated tissue spheroids in a yield-stress gel. Communications Physics 3, 183, doi: 10.1038/s42005-020-00449-4 (2020).

Kim et al. (2022) Aspiration-assisted freeform bioprinting of mesenchymal stem cell spheroids within alginate microgels. Biofabrication 14, 024103, doi:10.1088/1758-5090/ac4dd8 (2022).

Brunel et al. (2022) Engineered assistive materials for 3D bioprinting: support baths and sacrificial inks. Biofabrication 14, 032001, doi:10.1088/1758-5090/ac6bbe (2022).

Moldovan et al. (2017) Principles of the Kenzan Method for Robotic Cell Spheroid-Based Three-Dimensional Bioprinting <sup/>. Tissue Eng Part B Rev 23, 237-244, doi:10.1089/ten.TEB. 2016.0322 (2017).

Wu et al. (2008) Magnetic iron oxide nanoparticles: synthesis and surface functionalization strategies. Nanoscale Res Lett 3, 397-415, doi:10.1007/s11671-008-9174-9 (2008).

Mattix et al. (2014) Biological magnetic cellular spheroids as building blocks for tissue engineering. Acta Biomater. 10(2):623-629.

Ho et al. (2010) Generation and manipulation of magnetic multicellular spheroids. Biomaterials 31:3095-3102.

Ino et al. (2007) Cell patterning using magnetite nanoparticles and magnetic force. Biotechnol Bioeng. 2007; 97:1309-1317.

Ino et al. (2009) Application of magnetic force-based cell patterning for controlling cell—cell interactions in angiogenesis. Biotechnol Bioeng. 102:882-890.

Akiyama et al. (2010) Cell-patterning using poly (ethylene glycol)-modified magnetite nanoparticles. J Biomed Mater Res Part A. 92A:1123-1130.

Bratt-Leal et al. (2011) Magnetic manipulation and spatial patterning of multi-cellular stem cell aggregates. Integr Biol. Integr Biol (Camb) 3(12):1224-1232.

Ho et al. (2013) Manipulating magnetic 3D spheroids in hanging drops for applications in tissue engineering and drug screening. Adv Healthc Mater. 2(11):1430-1434.

Mattix et al. (2014) Janus magnetic cellular spheroids for vascular tissue engineering. Biomaterials 35(3):949-960.

(Continued)

*Primary Examiner* — Teresa E Knight

(74) *Attorney, Agent, or Firm* — Jenny L. Buchbinder; Bozicevic, Field & Francis LLP

(57) ABSTRACT

Methods and devices are provided for the fabrication of multi-spheroid tissues with precise spatial control over spheroid positioning. In particular, a 3D bioprinter is provided comprising an electromagnet and dual printheads comprising a first nozzle and a second nozzle, wherein the first nozzle extrudes a magnetic ink and the second nozzle manipulates the electromagnet to provide spatial control over construction of a multi-spheroid tissue.

24 Claims, 45 Drawing Sheets

Specification includes a Sequence Listing.

(56)     References Cited

OTHER PUBLICATIONS

Zhuang et al. (2021) Using Spheroids as Building Blocks Towards 3D Bioprinting of Tumor Microenvironment. Int J Bioprint. 7(4):444.
Paun et al. (2020) Magnetically-driven 2D cells organization on superparamagnetic micromagnets fabricated by laser direct writing. Sci Rep. Oct. 2, 2020;10(1):16418.
Whatley et al. (2014) Magnetic-directed patterning of cell spheroids. J. Biomed. Mater. Res. A. 102(5):1537-1547.
Bowser et al. (2019) Biofabrication of neural microphysiological systems using magnetic spheroid bioprinting. Biofabrication 12(1):015002.
Caleffi et al. (2021) Magnetic 3D cell culture: State of the art and current advances. Life Sci. 286:120028.

Parfenov et al. (2020) Magnetic levitational bioassembly of 3D tissue construct in space. Sci. Adv. 6(29):eaba4174.
Baillargeon et al. (2019) Automating a Magnetic 3D Spheroid Model Technology for High-Throughput Screening. SLAS Technol. 24(4):420-428.
Tseng et al. (2015) A spheroid toxicity assay using magnetic 3D bioprinting and real-time mobile device-based imaging. Sci Rep 5:13987.
Urkasemsin et al. (2020) Bioprinting Strategies for Secretory Epithelial Organoids. Methods Mol Biol. 2140:243-249.
Adine et al. (2018) Engineering innervated secretory epithelial organoids by magnetic three-dimensional bioprinting for stimulating epithelial growth in salivary glands. Biomaterials 180:52-66.

* cited by examiner

| CNF (wt%) | G' recovery following one cycle (mean % ± SD) | G' recovery following two cycles (mean % ± SD) |
|---|---|---|
| 0.25 | 108.6 ± 66.2 | 67.6 ± 27.7 |
| 0.5 | 86.8 ± 6.0 | 84.3 ± 25.6 |
| 1.0 | 66.3 ± 8.4 | 63.7 ± 10.3 |
| 1.5 | 61.9 ± 1.2 | 60.4 ± 3.7 |

SPATIALLY CONTROLLED FABRICATION OF MULTI-SPHEROID TISSUES USING MAGNETIC BIOPRINTING

CROSS-REFERENCE TO RELATED APPLICATION

This application claims benefit under 35 U.S.C. § 119(e) of provisional application 63/337,794, filed May 3, 2022, which application is hereby incorporated by reference in its entirety.

INCORPORATION BY REFERENCE OF A SEQUENCE LISTING

A Sequence Listing is provided herewith as a Sequence Listing XML file, "STAN-1965" created on Apr. 25, 2023 and having a size of 13,391 bytes. The contents of the Sequence Listing XML file are incorporated by reference herein in their entirety.

BACKGROUND OF THE INVENTION

The development of the human nervous system is predicated upon spatiotemporally controlled interactions between cells from distinct lineages (Kelley et al. Cell 185, 42-61 (2022)). These interactions occur early in gestation and are therefore inherently inaccessible for studies which probe neurodevelopmental phenomena or evaluate the efficacy of drugs targeting tissues in their native environment. Human neural assembloids, three-dimensional (3D) cultures derived from the integration organoids, have been used to model cell-cell interactions and circuit formation in the developing nervous system and to identify possible therapeutic targets for neuropsychiatric disorders (Birey et al. *Nature* 545, 54-59 (2017); Bagley et al. *Nature Methods* 14, 743-751 (2017); Xiang, et al. *Cell Stem Cell* 21, 383-398.e387 (2017); Miura et al. *Nature Biotechnology* 38, 1421-1430 (2020); Andersen et al. *Cell* 183, 1913-1929.e1926 (2020); Kasai et al. *Cell Reports* 30, 18-24.e15 (2020); Fligor et al. *Stem Cell Reports* 16, 2228-2241 (2021)). Conventionally, neural organoid fusion is achieved by manually transferring organoids with a wide pipette tip into a microcentrifuge tube containing culture medium where, over the course of several days, the constitutive organoids integrate to form an assembloid (Miura et al. *Nature Protocols* 17, 15-35 (2022)). While the construction of these structures enables temporal control of the interactions between organoids, multidimensional spatial control of their fusion remains a challenge.

3D bioprinting, a process wherein cells, often with accompanying biomaterials, are deposited and assembled into tissues, has been leveraged to control the spatial arrangement of spheroids and organoids[10]. Broadly, the printing of organ building blocks (OBBs) can be categorized into two distinct approaches: continuous bioprinting, wherein the OBBs are encapsulated within the bioink or support scaffold (Goulart et al. *Biofabrication* 12, 015010 (2019); Skylar-Scott et al. *Science Advances* 5, eaaw2459 (2019), and aspiration-assisted bioprinting (AAB), wherein individual OBBs are manipulated by vacuum pressure (Ayan et al. *Science Advances* 6, eaaw5111 (2020); Daly et al. *Nature Communications* 12, 753 (2021)). Continuous bioprinting of neural organoids, while capable of creating thick, patterned tissue structures (Skylar-Scott et al., supra), is limited by its inability to address the positioning of individual OBBs as well as the high cost associated with deriving enough OBBs to populate the bioink or scaffold.

While significantly lower-throughput, AAB would be better suited to spatially pattern the fusion of neural assembloids in 3D as it is capable of controlling the specific 3D position of each OBB. However, here, we demonstrate that AAB is poorly suited for the fabrication of neural assembloids, as neural organoids exhibit large diameters, relatively weak surface tension, and a propensity to undergo plastic deformation and degrade under relatively low vacuum force.

SUMMARY OF THE INVENTION

Methods and devices are provided for the fabrication of multi-spheroid tissues with precise spatial control over spheroid positioning. In particular, a 3D bioprinter is provided comprising an electromagnet and dual printheads comprising a first nozzle and a second nozzle, wherein the first nozzle extrudes a magnetic ink and the second nozzle manipulates the electromagnet to provide spatial control over construction of a multi-spheroid tissue.

In one aspect, a method of producing a multi-spheroid tissue is provided, the method comprising: (a) providing a plurality of spheroids; (b) coating a selected spheroid of the plurality with magnetic particles; (c) turning on an electromagnet, wherein the electromagnet is connected to a rod that becomes magnetized when the electromagnet is turned on; (d) lowering the magnetized rod over the selected spheroid until the magnetized rod magnetically attaches to the magnetic particles coating the selected spheroid; (e) raising the magnetized rod, wherein the selected spheroid is lifted by the magnetized rod; (f) moving the magnetized rod carrying the selected spheroid to a position over a support scaffold; (g) lowering the magnetized rod over a selected location in the support scaffold; (h) turning off the electromagnet to demagnetize the rod, wherein the selected spheroid detaches from the demagnetized rod and is deposited at the selected location in the support scaffold; and (i) repeating (a)-(h), wherein additional spheroids of the plurality are coated with magnetic particles, moved with the magnetized rod, and deposited at selected locations in the support scaffold; and (j) culturing the plurality of spheroids within the support scaffold under conditions suitable for growth of the spheroids, wherein fusion of the plurality of spheroids results in generation of the multi-spheroid tissue.

In certain embodiments, the plurality of spheroids are provided in a culture medium comprising the magnetic particles, wherein said raising the magnetized rod lifts the selected spheroid out of the culture medium.

In certain embodiments, the magnetic particles are embedded in a hydrogel, wherein said raising the magnetized rod lifts the selected spheroid out of a container containing the hydrogel.

In certain embodiments, the magnetic particles are embedded in a cytocompatible hydrogel. In some embodiments, the hydrogel comprises a cellulose nanofiber (CNF). In some embodiments, the hydrogel comprises 0.025 percent by weight (wt %) to 0.10 wt % CNF. In some embodiments, the hydrogel comprises about 0.025 wt % CNF.

In certain embodiments, the method further comprises removing the support scaffold from the multi-spheroid tissue. For example, a support scaffold comprising a CNF hydrogel can be removed from the multi-spheroid tissue by treating the CNF hydrogel with a cellulase to degrade the CNF hydrogel while leaving the multi-spheroid tissue intact.

In certain embodiments, the support scaffold has rheological properties that enable the smooth movement of the constitutive spheroids and maintains their position. In some embodiments, the support scaffold is shear-thinning and self-healing.

In certain embodiments, the spheroids are organoids.

In certain embodiments, the multi-spheroid tissue is an assembloid.

In certain embodiments, the method further comprises culturing the resultant multi-spheroid tissue in a suspension culture.

In certain embodiments, the plurality of spheroids is derived from induced pluripotent stem cells (iPSCs). In some embodiments, the iPSCs are human or non-human iPSCs.

In certain embodiments, the spheroids comprise differentiated cells. In certain embodiments, the spheroids are derived from somatic cells. The somatic cells may be human or non-human somatic cells. In some embodiments, a spheroid comprises one or more types of somatic cells.

In another aspect, a bioprinter for producing a multi-spheroid tissue is provided, the bioprinter comprising: a plurality of microwells, wherein the microwells can be used for generating and culturing a plurality of spheroids; a reservoir comprising a support scaffold; a dual printhead comprising a first nozzle and a second nozzle, wherein the first nozzle comprises an extrusion channel, and the second nozzle is coupled to an electromagnet, wherein the electromagnet is connected to a rod that becomes magnetized when the electromagnet is turned on and demagnetized when the electromagnet is turned off; a container containing magnetic ink comprising magnetic particles, wherein the container is connected to the extrusion channel to allow the first nozzle to deposit the magnetic ink; a processor, wherein the processor is programmed to perform steps comprising: (i) locating a microwell that contains a selected spheroid; (ii) moving the dual printhead to a position over the microwell that contains the selected spheroid; (iii) instructing the first nozzle to deposit the magnetic ink in the microwell containing the selected spheroid, wherein the selected spheroid is coated with the magnetic ink; (iv) turning on the electromagnet, wherein the rod becomes magnetized; (v) lowering the magnetized rod over the selected spheroid until the magnetized rod magnetically attaches to the magnetic particles of the magnetic ink coating the selected spheroid; (vi) raising the magnetized rod, wherein the selected spheroid is lifted out of the microwell; (vii) moving the magnetized rod carrying the selected spheroid to a selected position in the reservoir; (viii) lowering the magnetized rod over a selected location in the support scaffold; (ix) turning off the electromagnet to demagnetize the rod, wherein the selected spheroid detaches from the demagnetized rod and is deposited at the selected location in the support scaffold; and (x) repeating (i)-(ix), wherein additional selected spheroids are coated with the magnetic ink, lifted from the plurality of microwells with the magnetized rod, moved to the reservoir, and detached from the demagnetized rod and deposited at selected locations in the support scaffold to provide spatial control of the fusion of the plurality of spheroids to produce the multi-spheroid tissue.

In certain embodiments, the rod comprises a ferromagnetic metal. In some embodiments, the ferromagnetic metal is iron.

In certain embodiments, the rod has a diameter ranging from 1 mm to 5 mm, including any diameter within this range such as 1 mm, 1.5 mm, 2 mm, 2.5 mm, 3 mm, 3.5 mm, 4 mm, 4.5 mm, or 5 mm. In some embodiments, the rod has a diameter of about 2 mm.

In certain embodiments, the magnetic ink comprises iron oxide magnetic particles.

In certain embodiments, the magnetic ink comprises magnetic particles embedded in a cytocompatible hydrogel. In some embodiments, the hydrogel of the magnetic ink comprises a cellulose nanofiber (CNF). In some embodiments, the hydrogel of the magnetic ink comprises 0.025 percent by weight (wt %) to 0.10 wt % CNF. In some embodiments, the hydrogel of the magnetic ink comprises about 0.025 wt % CNF.

In certain embodiments, the magnetic particles are magnetic nanoparticles.

In certain embodiments, the magnetic ink comprises 0.5 wt % to 3 wt % magnetic nanoparticles, including any wt % in this range such as 0.5 wt %, 1 wt %, 1.5 wt %, 2 wt %, 2.5 wt %, or 3 wt %. In some embodiments, the magnetic ink comprises at least 1 wt % magnetic nanoparticles. In some embodiments, the magnetic ink comprises about 1 wt % magnetic nanoparticles.

In certain embodiments, the support scaffold comprises a cytocompatible hydrogel. In some embodiments, the hydrogel of the support scaffold comprises 0.4 wt % to 0.6 wt % CNF. In some embodiments, the hydrogel of the support scaffold comprises about 0.5 wt % CNF.

In certain embodiments, the processor is further programmed to instruct the bioprinter to add cellulase to the support scaffold after step (j), wherein the support scaffold is removed from the multi-spheroid tissue.

In certain embodiments, the voltage of the electromagnet and distance of the magnetic rod from the selected spheroid can be adjusted to control magnetic field strength surrounding the selected spheroid.

In certain embodiments, the bioprinter further comprises a pump. Exemplary pumps include, without limitation, a syringe pump, a diaphragm pump, a peristaltic pump, or a piston pump.

In certain embodiments, the bioprinter further comprises a multiway selector valve interfaced with a pump.

In certain embodiments, the bioprinter further comprises a media ramp comprising one or more containers or wells comprising one or more types of media, wherein the one or more containers or wells are fluidically connected to the multiway selector valve such that a user can select a medium from the one or more types of media for distribution to one or more selected microwells.

In certain embodiments, the bioprinter further comprises a container or well comprising cellulase, wherein the container or well comprising cellulase is fluidically connected to the multiway selector valve such that a user can add cellulase to one or more selected microwells.

In certain embodiments, the bioprinter further comprises a chip, wherein the plurality of microwells and the reservoir comprising the support scaffold are contained on the chip. In some embodiments, the chip further comprises a raised connector channel between the microwells and the reservoir comprising the support scaffold. In some embodiments, the chip comprises polydimethylsiloxane (PDMS).

In certain embodiments, the plurality of microwells is arranged linearly in rows, where each row of microwells is fluidically connected to an inlet. In some embodiments, for each row, the inlet further comprises a syringe alignment pad, wherein the syringe alignment pad is aligned with one end of the row of microwells.

In certain embodiments, for each row of microwells, the chip further comprises an offset platform for medium addition to the microwells, wherein the offset platform for medium addition to the microwells is located between the syringe alignment pad and the row of microwells.

In certain embodiments, the bioprinter further comprises a temperature controller that maintains the microwells and the reservoir at a suitable temperature for culturing the plurality of spheroids and the multi-spheroid tissue.

In certain embodiments, the plurality of microwells and the reservoir comprising the support scaffold are contained on a chip, wherein the plurality of microwells is arranged linearly in rows, where each row of microwells is fluidically connected to an inlet; wherein for each row of microwells, the inlet further comprises a syringe alignment pad located at a first end of the row of microwells; wherein for each row of microwells, the chip further comprises an offset platform for medium addition to the microwells, wherein the offset platform for medium addition to the microwells is located between the syringe alignment pad and the row of microwells; and wherein for each row of microwells, the chip further comprises a raised connector channel located between the microwells and the reservoir comprising the support scaffold. In some embodiments, the chip further comprises a plurality of reservoirs comprising support scaffolds, wherein for each row of microwells, the syringe alignment pad is located at the first end of the row of microwells and one of the reservoirs of the plurality is located at the second end of the row of microwells, wherein each reservoir further comprises an inlet fluidically connected to the reservoir.

In certain embodiments, the bioprinter further comprise a power source, wherein the power source controls a voltage applied to the electromagnet and the strength of the magnetic force used to lift the spheroids.

In certain embodiments, the bioprinter further comprises an inlet fluidically connected to the reservoir comprising the support scaffold.

In certain embodiments, the plurality of spheroids is a plurality of organoids.

In certain embodiments, the multi-spheroid tissue is an assembloid.

In certain embodiments, the bioprinter comprises multiple dual printheads.

In another aspect, a method of using the bioprinter, described herein, to produce a multi-spheroid tissue is provided, the method comprising: (a) adding cells to the plurality of microwells, (b) adding spheroid-specific media to the plurality of microwells; (c) culturing the cells under suitable conditions, wherein the plurality of spheroids is generated from the cells; (d) instructing the processor to perform the steps comprising: (i) locating a microwell that contains a selected spheroid; (ii) moving the dual printhead to a position over the microwell that contains the selected spheroid; (iii) instructing the first nozzle to deposit the magnetic ink in the microwell containing the selected spheroid, wherein the selected spheroid is coated with the magnetic ink; (iv) turning on the electromagnet, wherein the rod becomes magnetized; (v) lowering the magnetized rod over the selected spheroid until the magnetized rod magnetically attaches to the magnetic particles of the magnetic ink coating the selected spheroid; (vi) raising the magnetized rod, wherein the selected spheroid is lifted out of the microwell; (vii) moving the magnetized rod carrying the selected spheroid to a selected position in the reservoir; (viii) lowering the magnetized rod over a selected location in the support scaffold; (ix) turning off the electromagnet to demagnetize the rod, wherein the selected spheroid detaches from the demagnetized rod and is deposited at the selected location in the support scaffold; and (x) repeating (i)-(ix), wherein additional selected spheroids are coated with the magnetic ink, lifted from the plurality of microwells with the magnetized rod, moved to the reservoir, and detached from the demagnetized rod and deposited at selected locations in the support scaffold; and (e) culturing the plurality of spheroids within the support scaffold under conditions suitable for growth of the spheroids, wherein fusion of the plurality of spheroids results in generation of the multi-spheroid tissue.

In certain embodiments, the method further comprises removing the support scaffold from the multi-spheroid tissue by treating the CNF hydrogel with a cellulase to degrade the CNF hydrogel while leaving the multi-spheroid tissue intact.

In certain embodiments, the method further comprises adjusting voltage of the electromagnet and distance of the magnetic rod from the selected spheroid to control magnetic field strength surrounding the selected spheroid. In some embodiments, the voltage of the electromagnet is about 15 volts.

In certain embodiments, the method further comprises culturing the multi-spheroid tissue in a suspension culture.

In certain embodiments, the method further comprises culturing the multi-spheroid tissue until the multi-spheroid tissue is mature.

In certain embodiments, the coated spheroids are lifted and positioned in the support scaffold sequentially.

In certain embodiments, the bioprinter comprises multiple dual printheads, wherein multiple coated spheroids are lifted and positioned in the support scaffold simultaneously.

In another aspect, a multi-spheroid tissue produced by a method, described herein, is provided.

In another aspect, a method of screening a candidate agent is provided, the method comprising: contacting a multi-spheroid tissue, produced as described herein, with the candidate agent, and determining the effects of the agent on morphologic, genetic, or functional parameters.

In certain embodiments, determining the effect of the agent comprises performing immunohistochemistry, gene expression profiling, confocal microscopy, atomic force microscopy, super-resolution microscopy, light-sheet microscopy, two-photon microscopy, fluorescence microscopy, calcium imaging, electrophysiology measurements, patch clamping, migration assays, axonal growth and pathfinding assays, or phagocytosis assays.

In certain embodiments, the multi-spheroid tissue comprises IPSC-derived cells, somatic cells, or donor derived cells, or any combination thereof.

In certain embodiments, the multi-spheroid tissue comprises IPSC-derived neurons, IPSC-derived glia, or IPSC-derived muscle cells, or any combination thereof.

In certain embodiments, the multi-spheroid tissue comprises a retinal spheroid, a thalamic spheroid, and a forebrain spheroid. In some embodiments, the thalamic spheroid is fused to the retinal spheroid and the forebrain spheroid.

In certain embodiments, the multi-spheroid tissue comprises a gastric spheroid and an intestinal spheroid. In some embodiments, the gastric spheroid is fused to the intestinal spheroid.

In certain embodiments, the multi-spheroid tissue comprises neural organoids, mesenchymal stromal cell (MSC) spheroids, or human umbilical vein endothelial cell (HU-VEC) spheroids.

In certain embodiments, the multi-spheroid tissue comprises a dorsal forebrain neural organoid, a ventral forebrain neural organoid, or a combination thereof.

In certain embodiments, the multi-spheroid tissue further comprises a frontal lobe diffuse intrinsic pontine glioma (DIPG) organoid, a pons DIPG organoid, or a combination thereof.

In certain embodiments, the method further comprises using optogenetics to excite or inhibit one or more selected IPSC-derived neurons of interest using light.

In another aspect, a computer implemented method for controlling a bioprinter for producing a multi-spheroid tissue is provided, the computer performing steps comprising: (a) locating a microwell that contains a selected spheroid; (b) moving the dual printhead to a position over the microwell that contains the selected spheroid; (c) instructing the first nozzle to deposit the magnetic ink in the microwell containing the selected spheroid, wherein the selected spheroid is coated with the magnetic ink; (d) turning on the electromagnet, wherein the rod becomes magnetized; (e) lowering the magnetized rod over the selected spheroid until the magnetized rod magnetically attaches to the magnetic particles of the magnetic ink coating the selected spheroid; (f) raising the magnetized rod, wherein the selected spheroid is lifted out of the microwell; (g) moving the magnetized rod carrying the selected spheroid to a selected position in the reservoir; (h) lowering the magnetized rod over a selected location in the support scaffold; (i) turning off the electromagnet to demagnetize the rod, wherein the selected spheroid detaches from the demagnetized rod and is deposited at the selected location in the support scaffold; and (j) repeating (a)-(i), wherein additional selected spheroids are coated with the magnetic ink, lifted from the plurality of microwells with the magnetized rod, moved to the reservoir, and detached from the demagnetized rod and deposited at selected locations in the support scaffold to provide spatial control of the fusion of the plurality of spheroids to produce the multi-spheroid tissue.

In certain embodiments, the implemented method further comprises instructing the bioprinter to add cellulase to the support scaffold after step (j), wherein the support scaffold is removed from the multi-spheroid tissue.

In another aspect, a non-transitory computer-readable medium is provide, the non-transitory computer-readable medium comprising program instructions that, when executed by a processor in a computer, causes the processor to perform the method described herein for controlling a bioprinter for producing a multi-spheroid tissue.

In another aspect, a kit comprising the non-transitory computer-readable medium, described herein, and instructions for producing a multi-spheroid tissue is provided. In some embodiments, the kit further comprises a bioprinter described herein.

BRIEF DESCRIPTION OF THE DRAWINGS

FIG. 1A. Diameter measurements of MSC and HUVEC spheroids, and hiPSC-derived ventral and dorsal forebrain neural organoids at increasing days of culture. FIG. 1B. Mass measurements of spheroids and neural organoids. Each data point represents an average of five biological replicates. FIG. 1C. Vacuum pressure required to lift neural organoids of increasing diameters within a liquid medium.

FIG. 1D. Surface tension of spheroids and neural organoids. FIG. 1E. Schematic of vacuum aspiration-assisted lifting of neural organoids. FIG. 1F. Representative brightfield (BF) images of a neural organoid prior to vacuum aspiration. FIG. 1G. Representative BF images of a neural organoid post vacuum aspiration (6 mmHg). FIG. 1H. Representative BF image of a neural organoid that has undergone complete deformation (i.e., is no longer spherical) post vacuum aspiration (6 mmHg). FIG. 1I. Quantification of the extent of deformation as a function of the applied vacuum pressure. Each color represents a single neural organoid (n=3). FIG. 1J. Representative quantification of neural organoid deformation during and immediately following vacuum aspiration (6 mmHg). FIG. 1K. Long-term neural organoid deformation in response to two vacuum pressures (6 mmHg and 10 mmHg). Each set of data points connected with a line represents a single biological replicate. FIG. 1L. Schematic of magnetic lifting of neural organoids. FIG. 1M. Representative BF image of a neural organoid post magnetic lifting. Statistical analyses performed as one-way ANOVA with Tukey multiple comparisons test. Unless otherwise noted, all data points represent distinct biological replicates. Data plotted as mean±SD where $*p<0.05$, $p<0.01$, $*p<0.001$, $****p<0.0001$, and ns=not significant.

FIG. 2A. Schematic of the STAMP platform. FIG. 2B. Representative images of a neural organoid being coated in an MNP-laden CNF ink, lifted and transferred into a CNF support scaffold by a magnetic rod attached to an electromagnet-modified 3D printer, and released at a desired position within the support scaffold. FIG. 2C. Representative viscosity measurements of inks with 1 wt % MNP and various CNF wt %. FIG. 2D. Quantification of the relative degree of MNP dispersion within CNF inks of various wt % over 15 minutes (n=4). Inset: Representative image of MNP dispersion within a microcentrifuge tube. FIG. 2E. Representative image of MNP-laden CNF inks extruded over the top of neural organoids. FIG. 2F. Representative storage modulus (filled circles) and loss modulus (open circles) of 0.5 wt % CNF support scaffold exposed to cyclical periods of low (0.1%) and high (300%) strain to evaluate the ability of the material to shear thin and self-heal. FIG. 2G. Storage modulus of CNF support scaffolds of various wt % (n=4). FIG. 2H. Representative viscosity measurements of 0.5 wt % CNF support scaffolds in response to treatment with various concentrations of cellulase. FIG. 2I. Quantification of the extent of MNP coverage on the surface of a neural organoid following coating with 1 wt % MNPs in DPBS or a 1 wt % MNP-laden 0.025 wt % CNF ink. FIG. 2J. Representative BF image of a neural organoid following STAMP. Statistical analyses performed as one-way ANOVA with Tukey multiple comparisons test or two-way ANOVA with either Dunnett's multiple comparisons test or Šidák's multiple comparisons test. Unless otherwise noted, all data points represent distinct biological replicates. Data plotted as mean±SD where $*p<0.05$, $p<0.01$, $*p<0.001$, $****p<0.0001$, and ns=not significant.

FIG. 3A. Schematic of the potential automation of STAMP. Specific media formulations (depicted as red or green) can be portioned into distinct channels within a custom-built chip designed to facilitate the maintenance and differentiation of tissue-specific spheroids and organoids. Dotted lines represent the potential path an electromagnet-modified 3D printer could take to create an assembloid. FIG. 3B. Precision, in X and Y dimensions, of automated alginate microgel transfer. Each data point represents a single microgel wherein each microgel yielded data in both X and Y dimensions. FIG. 3C. Drift (i.e., the distance between where an alginate microgel was intended to be deposited and where the microgel settled) in the Z dimension as a function of microgel diameter. FIG. 3D. Positional stability (i.e., Z dimensional drift relative to the initial displacement) over time of alginate microgels over 72 hours (n=7). FIG. 3E. Representative fluorescence image of an eGFP-expressing ventral forebrain neural organoid fused to two mScarlet-expressing dorsal forebrain neural organoids. FIG. 3F. Representative fluorescence image of two eGFP-expressing ventral forebrain neural organoids, two mScarlet-expressing dorsal forebrain neural organoids, and two non-fluorescent dorsal forebrain neural organoids from distinct hiPSC lines fused in a ring. FIG. 3G. Representative fluorescence image of an eGFP-expressing ventral forebrain neural organoid fused to three mScarlet-expressing dorsal forebrain neural organoids in a multi-layered pyramid in which the ventral organoid is above the dorsal organoids. FIG. 3H. Representative immunofluorescence (IF) image of a ventral forebrain neural organoid integrated with a dorsal forebrain neural organoid. FIG. 3I. Representative IF image of a ventral forebrain neural organoid integrated with a dorsal forebrain neural organoid with regions of higher magnification to illustrate cell migration. Unless otherwise noted, all data points represent distinct biological replicates. Data plotted as mean±SD.

FIG. 4A. Representative image of well plate with hiPSC-derived neural organoids fused to patient-derived DIPG organoids. FIG. 4B. Representative BF and IF images of a three-part assembloid in which two distinct DIPG organoids, derived from either the pons, which is the tumor origination site (DIPGXIII-P), or the frontal lobe, a brain region into which the tumor metastasized (DIPGXIII-FL). FIG. 4C. Representative IF staining of the apoptosis marker cleaved caspase-3 across an array of permutations of DIPG organoids fused to neural organoids in which a subset of the assembloids were treated with 200 nM panobinostat. FIG. 4D. Quantification of the relative degree of apoptosis as determined by cleaved caspase-3 staining within DIPG organoids normalized by DAPI and relative to the untreated control organoids. FIG. 4E. Representative IF staining of H3K27M across an array of permutations of DIPG organoids fused to neural organoids in which a subset of the assembloids were treated with 200 nM panobinostat. FIG. 4F. Quantification of the relative number of H3K27M-expressing cells. H3K27M staining within DIPG organoids was normalized by DAPI and shown relative to the untreated control organoids. Statistical analyses performed as two-way ANOVA with Šidák's multiple comparisons test. Unless otherwise noted, all data points represent distinct biological replicates. Data plotted as mean±SD where *p<0.05, p<0.01, *p<0.001, ****p<0.0001, and ns=not significant.

FIG. 5A. Representative BF image of a neural organoid adjacent to the vacuum aspirator used for surface tension measurements. FIG. 5B. Representative BF images of the same neural organoid across a range of vacuum pressures.

FIG. 7A. Quantification of neural organoid deformation over time following exposure to either 6 mmHg or 10 mmHg vacuum pressure (n=5 per vacuum pressure). FIG. 7B. Representative BF images of a single neural organoid exposed to either 6 mmHg or 10 mmHg over time. FIG. 7C. Representative BF images of a single neural organoid which, when exposed to 6 mmHg, exhibited a deformation so severe that it was no longer spherical, herein referred to as 'Complete Deformation'.

FIG. 8A. Representative BF images of different z-planes of a single neural organoid coated with an MNP-laden CNF ink. FIG. 8B. Representative images of the same neural organoid being lifted and released by an iron rod affixed to an electromagnet.

FIG. 9A. Magnetic field strength over increasing voltages. FIG. 9B. Magnetic field strength at distinct voltages over increasing distances.

FIG. 10A. Representative BF images of different z-planes of a single neural organoid incubated in an orbital shaker with MNPs in DPBS. FIG. 10B. Representative images of the same neural organoid being lifted and released by an iron rod affixed to an electromagnet.

FIG. 11A. Representative BF images of a single z-plane of a neural organoid coated with MNPs. FIG. 11B. Representative Prussian blue staining of an MNP-coated neural organoid wherein blue denotes iron. FIG. 11C. Representative Prussian blue staining of a neural organoid that has never come in contact with MNPs. FIG. 11D. mRNA expression of MAPK genes previously identified to have been affected by iron oxide nanoparticles (n=4). CTRL represent non-coated organoids while MNP represent MNP-coated organoids. Statistical analyses performed separately for each marker with unpaired t tests with Welch's correction. Data plotted as mean±SD where *p<0.05, p<0.01, *p<0.001, ****p<0.0001, and ns=not significant.

FIG. 12A. Representative storage modulus (filled circles) and loss modulus (open circles) of 0.25 wt % CNF support scaffold exposed to cyclical periods of low (0.1%) and high (300%) strain to evaluate the ability of the material to shear thin and self-heal. FIG. 12B. Representative storage modulus and loss modulus of 1.0 wt % CNF support scaffold exposed to cyclical periods of low and high strain. FIG. 12C. Representative storage modulus and loss modulus of 1.5 wt % CNF support scaffold exposed to cyclical periods of low and high strain. FIG. 12D. Summary of storage modulus recovery as a percentage of the initial modulus (n=4).

FIG. 13A. Storage modulus of 0.5 wt % CNF support scaffold over time with or without daily media changes. FIG. 13B. Schematic of the use of cellulase to degrade CNF. FIG. 13C. Storage modulus of 0.5 wt % CNF exposed to various wt % of cellulase (n=3). FIG. 13D. Storage modulus of 0.5 wt % CNF exposed to 0.5 wt % cellulase over time (n=3). FIG. 13E. Representative fluorescence images of neural organoids following 0.5 wt % cellulase treatment over time with calcein-AM labeled live cells (green) and ethidium homodimer-1-labeled dead cells (red). Statistical analyses performed as one-way ANOVA with Tukey multiple comparisons test. Data plotted as mean±SD where *p<0.05, p<0.01, *p<0.001, ****p<0.0001, and ns=not significant.

FIG. 14A. Representative BF images of a neural organoid following STAMP and removal from the CNF support scaffold. The organoid was treated with 0.5 wt % cellulase over 3 days to remove residual CNF on the organoid's surface. FIG. 14B. Quantification of CNF removal with 0.5 wt % cellulase. Each set of data points connected with a line represents a single replicate.

FIG. 16A. 3D rendering with measurements of the chip designed to facilitate STAMP automation. FIG. 16B. Image of the chip after the PDMS has been cured. The reservoirs are filled with DPBS with blue food coloring to provide contrast. FIG. 16C. Image of the STAMP set-up.

FIG. 17A. Precision of automated STAMP positioning in X and Y dimensions. Data points represent the observed positions where alginate microgels were deposited in a coordinate plane wherein (0,0) represents the intended position of the microgel. FIG. 17B. Quantification of the initial Z drift. FIG. 17C. Z drift of microgels with diameters greater than 1.5 mm over time. FIG. 17D. Z drift of microgels with diameters less than 1.5 mm over time. FIG. 17E. Total XY drift of microgels over time.

DETAILED DESCRIPTION OF THE INVENTION

Figure 1A:
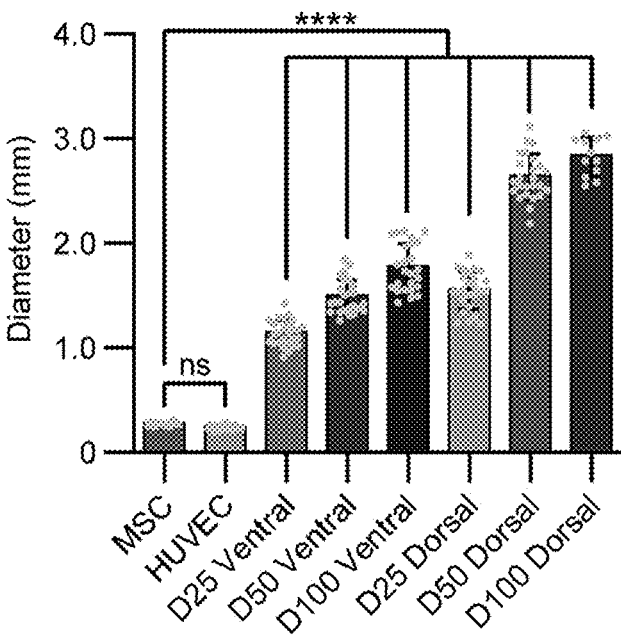
FIGS. 1A-1M. Magnetic lifting maintains the structural integrity of neural organoids.

Methods and devices are provided for fabrication of multi-spheroid tissues with precise spatial control over spheroid positioning. In particular, a 3D bioprinter is provided with dual printheads wherein one comprises a nozzle which extrudes a magnetic ink and the second has been modified to move an electromagnet to provide spatial control over construction of the multi-spheroid tissue.

Before the present methods and devices are described, it is to be understood that this invention is not limited to particular methods or compositions described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the magnetic particle" includes reference to one or more magnetic particles and equivalents thereof, such as superparamagnetic particles, magnetic beads, iron oxide particles, and the like, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "about", particularly in reference to a given quantity, is meant to encompass deviations of plus or minus five percent.

"Biocompatible" or "cytocompatible" as used herein, refers to a property of a material that allows for prolonged contact with a cell or tissue without causing toxicity or significant damage.

The term "hydrogel" refers to a substance formed when an organic polymer (natural or synthetic) is cross-linked via covalent, ionic, or hydrogen bonds to create a three-dimensional open-lattice structure which entraps water molecules to form a gel. In general, these polymers are at least partially soluble in aqueous solutions, such as water, buffered salt solutions, or aqueous alcohol solutions that have charged side groups, or a monovalent ionic salt thereof. Biocompatible hydrogel refers to a polymer that forms a gel which is not toxic to living cells, and allows sufficient diffusion of oxygen and nutrients to the entrapped cells to maintain viability.

The term "magnetic ink" refers to a liquid or gel composition suitable for bioprinting, wherein the composition comprises magnetic particles.

The term "stem cell" refers to a cell that retains the ability to renew itself through mitotic cell division and that can differentiate into a diverse range of specialized cell types. Mammalian stem cells can be divided into three broad categories: embryonic stem cells, which are derived from blastocysts, adult stem cells, which are found in adult tissues, and cord blood stem cells, which are found in the umbilical cord. In a developing embryo, stem cells can differentiate into all of the specialized embryonic tissues. In adult organisms, stem cells and progenitor cells act as a repair system for the body by replenishing specialized cells. Totipotent stem cells are produced from the fusion of an egg and sperm cell. Cells produced by the first few divisions of the fertilized egg are also totipotent. These cells can differentiate into embryonic and extraembryonic cell types. Pluripotent stem cells are the descendants of totipotent cells and can differentiate into cells derived from any of the three germ layers. Multipotent stem cells can produce only cells of a closely related family of cells (e.g., hematopoietic stem cells differentiate into red blood cells, white blood cells, platelets, etc.). Unipotent cells can produce only one cell type, but have the property of self-renewal, which distinguishes them from non-stem cells. Induced pluripotent stem cells are a type of pluripotent stem cell derived from adult cells that have been reprogrammed into an embryonic-like pluripotent state. Induced pluripotent stem cells can be derived, for example, from adult somatic cells such as peripheral blood mononuclear cells, fibroblasts, keratinocytes, epithelial cells, endothelial progenitor cells, mesenchymal stem cells, adipose derived stem cells, leukocytes, hematopoietic stem cells, bone marrow cells, or hepatocytes.

As used herein, "reprogramming factors" refers to one or more, i.e., a cocktail, of biologically active factors that act on a cell to alter transcription, thereby reprogramming a cell to multipotency or to pluripotency. Reprogramming factors may be provided individually or as a single composition, that is, as a premixed composition, of reprogramming factors to the cells, e.g., somatic cells from an individual with a family history or genetic make-up of interest, such as a patient who has a neurological disorder or a neurodegenerative disease. The factors may be provided at the same molar ratio or at different molar ratios. The factors may be provided once or multiple times in the course of culturing the cells of the subject invention. In some embodiments the reprogramming factor is a transcription factor, including without limitation, Oct3/4; Sox2; Klf4; c-Myc; Nanog; and Lin-28.

The somatic cells may include, without limitation, peripheral blood mononuclear cells, fibroblasts, keratinocytes, epithelial cells, endothelial progenitor cells, mesenchymal stem cells, adipose derived stem cells, leukocytes, hematopoietic stem cells, bone marrow cells, or hepatocytes, etc., which are contacted with reprogramming factors, as defined above, in a combination and quantity sufficient to reprogram the cell to pluripotency. Reprogramming factors may be provided to the somatic cells individually or as a single composition, that is, as a premixed composition, of reprogramming factors. In some embodiments the reprogramming factors are provided as a plurality of coding sequences on a vector.

The term "spheroid" refers to a three-dimensional (3D) cluster of cells.

The term "organoid" refers to a 3D cluster of organ-specific cells of multiple subtypes that exhibit some organ-appropriate organization and physiology. Organoids are a sub-class of spheroids.

The term "multi-spheroid tissue" refers to 3D tissues derived from the fusion of spheroids.

The term "assembloid" refers to 3D tissues derived from the fusion of tissue-specific organoids. Assembloids are a sub-class of multi-spheroid tissues.

The term "user" as used herein refers to a person that uses a bioprinter disclosed herein for performing one or more steps of the presently disclosed methods to produce a multi-spheroid tissue.

A "CRISPR system" refers collectively to transcripts and other elements involved in the expression of or directing the activity of CRISPR-associated ("Cas") genes. In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*. In general, a CRISPR system is characterized by elements that promote the formation of a CRISPR complex at the site of a target sequence.

The term "Cas9" as used herein encompasses type II clustered regularly interspaced short palindromic repeats (CRISPR) system Cas9 endonucleases from any species, and also includes biologically active fragments, variants, analogs, and derivatives thereof that retain Cas9 endonuclease activity (i.e., catalyze site-directed cleavage of DNA to generate double-strand breaks).

A Cas9 endonuclease binds to and cleaves DNA at a site comprising a sequence complementary to its bound guide RNA (gRNA). For purposes of Cas9 targeting, a gRNA may comprise a sequence "complementary" to a target sequence (e.g., major or minor allele), capable of sufficient base-pairing to form a duplex (i.e., the gRNA hybridizes with the target sequence). Additionally, the gRNA may comprise a sequence complementary to a PAM sequence, wherein the gRNA also hybridizes with the PAM sequence in a target DNA.

By "selectively binds" with reference to a guide RNA is meant that the guide RNA binds preferentially to a target sequence of interest or binds with greater affinity to the target sequence than to other genomic sequences. For example, a gRNA will bind to a substantially complementary sequence and not to unrelated sequences. A gRNA that "selectively binds" to a particular allele, such as a particular mutant allele (e.g., allele comprising a substitution, insertion, or deletion), denotes a gRNA that binds preferentially to the particular target allele, but to a lesser extent to a wild-type allele or other sequences. A gRNA that selectively binds to a particular target DNA sequence will selectively direct binding of Cas9 to a substantially complementary sequence at the target site and not to unrelated sequences.

The term "donor polynucleotide" refers to a polynucleotide that provides a sequence of an intended edit to be integrated into the genome at a target locus by homology directed repair (HDR).

A "target site" or "target sequence" is the nucleic acid sequence recognized (i.e., sufficiently complementary for hybridization) by a guide RNA (gRNA) or a homology arm of a donor polynucleotide. The target site may be allele-specific (e.g., a major or minor allele).

By "homology arm" is meant a portion of a donor polynucleotide that is responsible for targeting the donor polynucleotide to the genomic sequence to be edited in a cell. The donor polynucleotide typically comprises a 5' homology arm that hybridizes to a 5' genomic target sequence and a 3' homology arm that hybridizes to a 3' genomic target sequence flanking a nucleotide sequence comprising the intended edit to the genomic DNA. The homology arms are referred to herein as 5' and 3' (i.e., upstream and downstream) homology arms, which relates to the relative position of the homology arms to the nucleotide sequence comprising the intended edit within the donor polynucleotide. The 5' and 3' homology arms hybridize to regions within the target locus in the genomic DNA to be modified, which are referred to herein as the "5' target sequence" and "3' target sequence," respectively. The nucleotide sequence comprising the intended edit is integrated into the genomic DNA by HDR or recombineering at the genomic target locus recognized (i.e., sufficiently complementary for hybridization) by the 5' and 3' homology arms.

"Administering" a nucleic acid, such as an inhibitory or regulatory nucleic acid (e.g., microRNA, siRNA, piRNA, snRNA, antisense nucleic acid, or lncRNA), or a CRISPR system (expressing, e.g., a donor polynucleotide, guide RNA, Cas protein (e.g., Cas9, Cas12a, Cas12d, Cas13, or dCas9)) to a cell comprises transducing, transfecting, electroporating, translocating, fusing, phagocytosing, shooting or ballistic methods, etc., i.e., any means by which a nucleic acid can be transported across a cell membrane.

Fabrication of Multi-Spheroid Tissues by Magnetic Bioprinting

Methods and devices are provided for the fabrication of multi-spheroid tissues with precise spatial control over spheroid positioning. In some embodiments, the subject methods comprise: (a) providing a plurality of spheroids; (b) coating a selected spheroid of the plurality with magnetic particles; (c) turning on an electromagnet, wherein the electromagnet is connected to a rod that becomes magnetized when the electromagnet is turned on; (d) lowering the magnetized rod over the selected spheroid until the magnetized rod magnetically attaches to the magnetic particles coating the selected spheroid; (e) raising the magnetized rod, wherein the selected spheroid is lifted by the magnetized rod; (f) moving the magnetized rod carrying the selected spheroid to a position over a support scaffold; (g) lowering the magnetized rod over a selected location in the support scaffold; (h) turning off the electromagnet to demagnetize the rod, wherein the selected spheroid detaches from the demagnetized rod and is deposited at the selected location in the support scaffold; and (i) repeating (a)-(h), wherein additional spheroids of the plurality are coated with magnetic particles, moved with the magnetized rod, and deposited at selected locations in the support scaffold; and (j) culturing the plurality of spheroids within the support scaffold under conditions suitable for growth of the spheroids, wherein fusion of the plurality of spheroids results in generation of the multi-spheroid tissue. The subject methods allow a plurality of spheroids, coated with magnetic particles, to be positioned in any desired arrangement in a support scaffold. In certain embodiments, the plurality of spheroids are provided in a culture medium comprising the magnetic particles, wherein raising the magnetized rod lifts the selected spheroid out of the culture medium. In other embodiments, the magnetic particles are embedded in a hydrogel, wherein raising the magnetized rod lifts the selected spheroid out of a container containing the hydrogel.

In certain embodiments, this method is performed using a three-dimensional (3D) bioprinter adapted with a dual printhead comprising a nozzle that deposits magnetic ink for coating spheroids and a magnetized rod for lifting spheroids and moving them to a support scaffold where the multi-spheroid tissue is assembled. The dual printhead may be added to various types of bioprinters including, without limitation, an inkjet printer, a laser-assisted printer, or an extrusion printer. In some embodiments, the bioprinter includes a processor to provide programmatic control of the printing process, including, for example, controlling the position of the dual printhead, controlling the flow rate of the magnetic ink, and controlling the position of the magnetized rod.

Figure 2A:
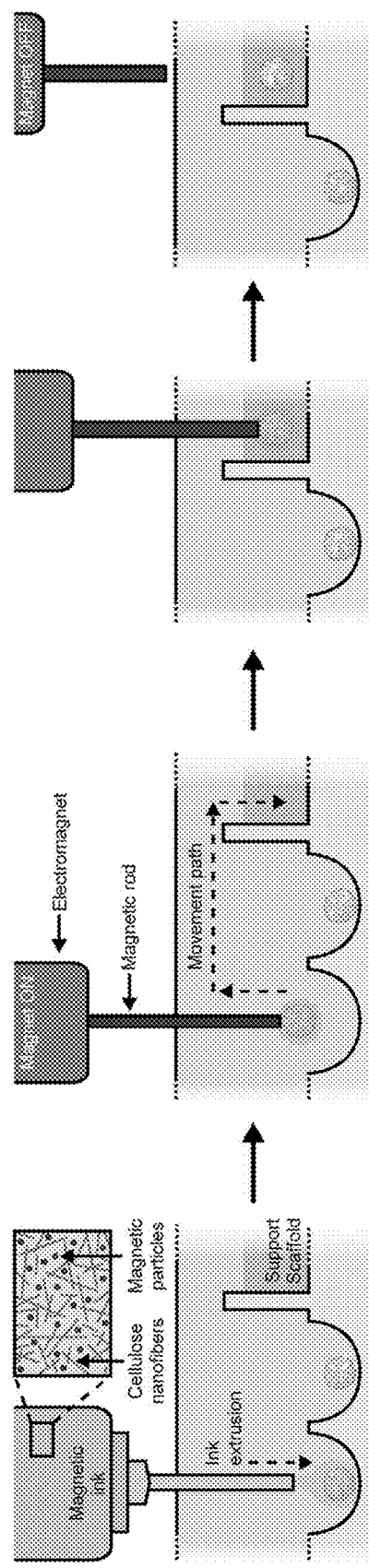
FIGS. 2A-2J. Cellulose nanofibers mediate the bioprinting of neural organoids with STAMP.

An exemplary embodiment of such a bioprinter is shown in FIG. 2A. The bioprinter comprises: a plurality of microwells, wherein the microwells can be used for generating and culturing a plurality of spheroids; a reservoir comprising a support scaffold; a dual printhead comprising a first nozzle and a second nozzle, wherein the first nozzle comprises an extrusion channel, and the second nozzle is coupled to an electromagnet, wherein the electromagnet is connected to a rod that becomes magnetized when the electromagnet is turned on and demagnetized when the electromagnet is turned off; a container containing magnetic ink comprising magnetic particles, wherein the container is connected to the extrusion channel to allow the first nozzle to deposit the magnetic ink; a processor, wherein the processor is programmed to perform steps comprising: (i) locating a microwell that contains a selected spheroid; (ii) moving the dual printhead to a position over the microwell that contains the selected spheroid; (iii) instructing the first nozzle to deposit the magnetic ink in the microwell containing the selected spheroid, wherein the selected spheroid is coated with the magnetic ink; (iv) turning on the electromagnet, wherein the rod becomes magnetized; (v) lowering the magnetized rod over the selected spheroid until the magnetized rod magnetically attaches to the magnetic particles of the magnetic ink coating the selected spheroid; (vi) raising the magnetized rod, wherein the selected spheroid is lifted out of the microwell; (vii) moving the magnetized rod carrying the selected spheroid to a selected position in the reservoir; (viii) lowering the magnetized rod over a selected location in the support scaffold; (ix) turning off the electromagnet to demagnetize the rod, wherein the selected spheroid detaches from the demagnetized rod and is deposited at the selected location in the support scaffold; and x) repeating (i)-(ix), wherein additional selected spheroids are coated with the magnetic ink, lifted from the plurality of microwells with the magnetized rod, moved to the reservoir, and detached from the demagnetized rod and deposited at selected locations in the support scaffold to provide spatial control of the fusion of the plurality of spheroids to produce the multi-spheroid tissue.

Figure 3A:
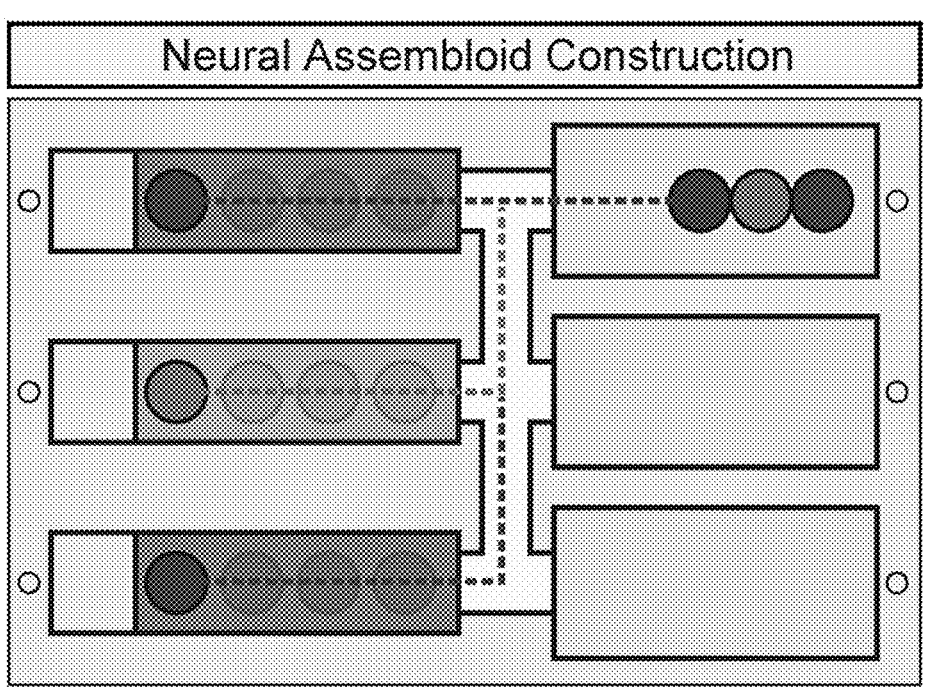
FIGS. 3A-3I. STAMP imparts spatial control over the construction of neural assembloids.
Figure 22:
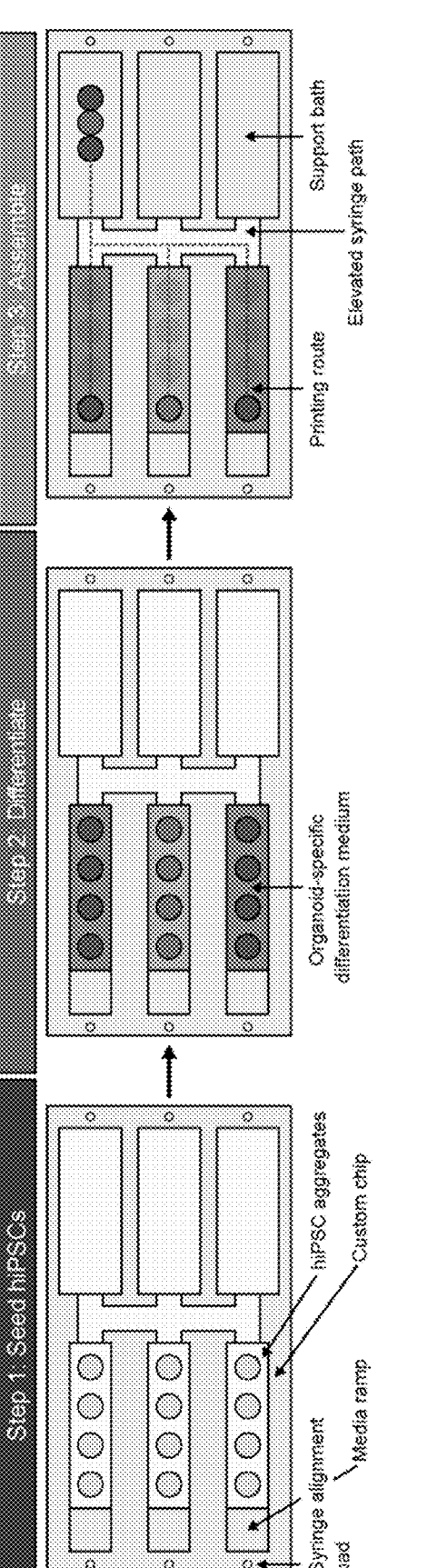
FIG. 22. Spheroids can be cultured (including differentiation or any other experimental manipulation) within a microwell chip before being assembled with the magnetic bioprinting platform described herein.

In some embodiments, the plurality of microwells and the reservoir comprising the support scaffold are arranged on a chip contained in the bioprinter. An exemplary embodiment of such a chip is shown in FIG. 3A and FIG. 22, wherein the plurality of microwells is arranged linearly in rows, where each row of microwells is fluidically connected to an inlet. For each row of microwells, the inlet further comprises a syringe alignment pad located at a the end of the row of microwells. In addition, for each row of microwells, the chip further comprises an offset platform for medium addition to the microwells, wherein the offset platform for medium addition to the microwells is located between the syringe alignment pad and the row of microwells. The chip further comprises raised connector channels located between each row of microwells and the reservoir comprising the support scaffold. In some embodiments, the chip comprises a plurality of reservoirs comprising support scaffolds, wherein for each row of microwells, the syringe alignment pad is located at one end of the row of microwells and one of the reservoirs of the plurality is located at the other end of the row of microwells, wherein each reservoir further comprises an inlet fluidically connected to the reservoir.

By "magnetic ink" is meant a liquid or gel composition suitable for printing, wherein the composition comprises magnetic particles. The magnetic particles typically comprise magnetic iron oxide, but other types of magnetic particles comprising other magnetic metals or magnetic metal oxides may also be used, including, but not limited to, magnetic particles comprising magnetic nickel or cobalt. Preferably the magnetic particles are biocompatible with the spheroids being assembled by the methods described herein. To be delivered by a bioprinter, the magnetic ink is formulated to meet the rheological requirements to be printable. By "printable" is meant, in reference to a magnetic ink, that droplets of the magnetic ink are able to be ejected from the nozzle repeatedly, preferably with uniform velocities and volumes. Key rheological parameters affecting printability are viscosity, density and surface tension (see, e.g., Derby, Annu. Rev. Mater. Sci., 40:395-414 (2010); Derby, J. Mater. Chem., 18:5717-57-21 (2008); Calvert, Chem. Mater., 13:3299-3305 (2001); Tekin et al, Soft Matter, 4:703-713 (2008); and like references. In some cases, the bioprinter may include a pneumatic regulator to control the flow of magnetic ink through a printhead nozzle.

In some embodiments, the magnetic ink comprises magnetic particles having a diameter ranging from about 1 nm to about 6 μm, about 20 nm to about 2 μm; about 30 nm to about 500 nm; about 40 nm to about 200 nm; or about 50 nm to about 100 nm, including any diameter with these ranges such as 1 nm, 2 nm, 3 nm, 4 nm, 5 nm, 6 nm, 7 nm, 8 nm, 10 nm, 15 nm, 20 nm, 25 nm, 30 nm, 35 nm, 40 nm, 45 nm 50 nm, 55 nm, 60 nm, 65 nm, 70 nm, 75 nm, 80 nm, 85 nm, 90 nm, 95 nm, 100 nm, 150 nm, 200 nm, 250 nm, 300 nm, 350 nm, 400 nm, 450 nm, 500 nm, 550 nm 600 nm, 650 nm, 700 nm, 800 nm, 850 nm, 900 nm, 1 μm, 1.5 μm, 2 μm, 2.5 μm, 3 μm, 3.5 μm, 4 μm, 4.5 μm, 5 μm, 5.5 μm, or 6 μm.

In certain embodiments, the magnetic ink comprises 0.5 wt % to 3 wt % magnetic nanoparticles, including any wt % in this range such as 0.5 wt %, 1 wt %, 1.5 wt %, 2 wt %, 2.5 wt %, or 3 wt %. In some embodiments, the magnetic ink comprises at least 1 wt % magnetic nanoparticles. In some embodiments, the magnetic ink comprises about 1 wt % magnetic nanoparticles.

The magnetic particles may be embedded in a cytocompatible hydrogel suitable for bioprinting. In some embodiments, the magnetic ink comprises magnetic particles embedded in a nanocellulose hydrogel. Nanocellulose hydrogels are well suited for 3D bioprinting due to their biocompatibility, printability, shear thinning characteristics, and their ability to promote survival of cells. In some embodiments, the magnetic ink comprises a cellulose nanofiber (CNF) hydrogel. See Example 1 for a description of a suitable CNF hydrogel for use in the magnetic ink. For additional examples of CNF hydrogels, see also, e.g., Guan et al. (2021) ACS Nano 15(5):7889-7898, Radeke et al. (2023) ACS Appl Mater Interfaces 15(2):2564-2577, Lan et al. (2021) Front Bioeng Biotechnol. 9:766399, Athukoralalage et al. (2019) Polymers (Basel) 11(5):898, Wang et al. (2020) Bioengineering (Basel) 7(2):40; herein incorporated by reference in their entireties.

In some embodiments, the hydrogel of the magnetic ink comprises 0.025 percent by weight (wt %) to 0.10 wt % CNF. In some embodiments, the hydrogel of the magnetic ink comprises about 0.025 wt % CNF.

The container containing the magnetic ink may be connected to the extrusion channel of the first nozzle with tubing that allows the magnetic ink to be expelled from the container while maintaining aseptic conditions. In some embodiments, the container holding the magnetic ink is a cartridge suitable for use with the bioprinter. In some embodiments, the cartridge is compatible with ink-jet printing of the magnetic ink. The cartridge is preferably configured to be filled with the magnetic ink aseptically and to prevent contamination. The cartridge may have a seal that maintains a sterile closed system after being filled with the magnetic ink.

In certain embodiments, the bioprinter comprises one or more additional dual printheads. A single dual print head is limited in the rate at which it can dispense magnetic ink and lift and move spheroids. To increase the rate of assembly of a multi-spheroid tissue, multiple dual printheads may be assembled in a bioprinter to dispense magnetic ink in multiple microwells and lift and move multiple magnetic ink-coated spheroids in parallel. In theory, the rate of assembly of a multi-spheroid tissue can be increased by a factor equal to the number of dual print heads included in the bioprinter. In certain embodiments, the bioprinter comprises 2 or more, 4 or more, 6 or more, 8 or more, or 10 or more dual printheads, such as 1 to 20 dual printheads, 2 to 15 dual printheads, 3 to 10 dual printheads, or 4 to 8 dual printheads, including any number of dual printheads within these ranges such as 1 dual printhead, 2 dual printheads, 3 printheads, 4 printheads, 5 printheads, 6 printheads, 7 printheads, 8 printheads, 9 printheads, 10 printheads, 11 printheads, 12 printheads, 13 printheads, 14 printheads, 15 printheads, 16 printheads, 17 printheads, 18 printheads, 19 printheads, or 20 dual printheads.

In some embodiments, the container containing the magnetic ink comprises one dispensing orifice, which is connected to a nozzle extrusion channel of a single dual printhead. In other embodiments, the container containing the magnetic ink comprises 2, 3, 4, 5, 6, 7, 8, 9, 10, 11, 12, 13, 14, 15, 20, 30, 40, 50, 60, 70, 80, 90, or 100, or more dispensing orifices, wherein each orifice is connected to a nozzle extrusion channel of a different dual printhead. In some embodiments, the bioprinter comprises multiple containers containing magnetic ink, wherein each container is connected to a nozzle extrusion channel of a different dual printhead.

In some embodiments, the dual printhead nozzle has a diameter ranging from 10 μm to 0.6 mm, 50 μm to 100 μm, 0.1 mm to 0.6 mm, or 0.2 mm to 0.4 mm, including any diameter within these ranges such as 10 μm, 15 μm, 20 μm, 25 μm, 30 μm, 35 μm, 40 μm, 45 μm, 50 μm, 55 μm, 60 μm, 65 µm, 70 µm, 75 µm, 80 µm, 85 µm, 90 µm, 95 µm, or 0.1 mm, 0.2 mm, 0.3 mm, 0.4 mm, 0.5 mm, or 0.6 mm.

In certain embodiments, the rod comprises a ferromagnetic metal or metal alloy that becomes magnetized when the electromagnet is turned on and demagnetized when the electromagnet is turned off. For example, the rod may comprise a ferromagnetic transition metal, such as iron, nickel, or cobalt, or an alloy thereof. In some embodiments, the rod comprises iron.

In certain embodiments, the rod has a diameter ranging from 1 mm to 5 mm, including any diameter within this range such as 1 mm, 1.5 mm, 2 mm, 2.5 mm, 3 mm, 3.5 mm, 4 mm, 4.5 mm, or 5 mm. In some embodiments, the rod has a diameter of about 2 mm.

In certain embodiments, the support scaffold comprises a cytocompatible hydrogel. The support scaffold preferably has rheological properties that enable the smooth movement of the spheroids and maintain their position. In some embodiments, the support scaffold is shear-thinning and self-healing. In some embodiments, the hydrogel of the support scaffold comprises 0.4 wt % to 0.6 wt % CNF. In some embodiments, the hydrogel of the support scaffold comprises about 0.5 wt % CNF.

The bioprinter may comprise one or more pumps. Exemplary pumps include, without limitation, syringe pumps, diaphragm pumps, peristaltic pumps or piston pumps, or any combination thereof. In some embodiments, the pumps are positive displacement pumps or pressure generating pumps. In some embodiments, the bioprinter further comprises a multiway selector valve interfaced with a pump.

In certain embodiments, the bioprinter further comprises a media ramp comprising one or more containers or wells comprising one or more types of media, wherein the one or more containers or wells are fluidically connected to a multiway selector valve such that a user can select a medium from the one or more types of media for distribution to one or more selected microwells. In certain embodiments, the bioprinter further comprises a container or well comprising cellulase, wherein the container or well comprising cellulase is fluidically connected to the multiway selector valve such that a user can add cellulase to one or more selected microwells.

In certain embodiments, the bioprinter further comprises a temperature controller that maintains the microwells and the reservoir at a suitable temperature for culturing the plurality of spheroids and the multi-spheroid tissue.

In certain embodiments, the bioprinter further comprises a power source, wherein the power source controls a voltage applied to the electromagnet and the strength of the magnetic force used to lift the spheroids.

The bioprinter can be used to produce a multi-spheroid tissue by a method comprising: (a) adding cells to the plurality of microwells, (b) adding spheroid-specific media to the plurality of microwells; (c) culturing the cells under suitable conditions, wherein the plurality of spheroids is generated from the cells; (d) instructing the processor to perform the steps comprising: (i) locating a microwell that contains a selected spheroid; (ii) moving the dual printhead to a position over the microwell that contains the selected spheroid; (iii) instructing the first nozzle to deposit the magnetic ink in the microwell containing the selected spheroid, wherein the selected spheroid is coated with the magnetic ink; (iv) turning on the electromagnet, wherein the rod becomes magnetized; (v) lowering the magnetized rod over the selected spheroid until the magnetized rod magnetically attaches to the magnetic particles of the magnetic ink coating the selected spheroid; (vi) raising the magnetized rod, wherein the selected spheroid is lifted out of the microwell; (vii) moving the magnetized rod carrying the selected spheroid to a selected position in the reservoir; (viii) lowering the magnetized rod over a selected location in the support scaffold; (ix) turning off the electromagnet to demagnetize the rod, wherein the selected spheroid detaches from the demagnetized rod and is deposited at the selected location in the support scaffold; and (x) repeating (i)-(ix), wherein additional selected spheroids are coated with the magnetic ink, lifted from the plurality of microwells with the magnetized rod, moved to the reservoir, and detached from the demagnetized rod and deposited at selected locations in the support scaffold; and (e) culturing the plurality of spheroids within the support scaffold under conditions suitable for growth of the spheroids, wherein fusion of the plurality of spheroids results in generation of the multi-spheroid tissue. In certain embodiments, the coated spheroids are lifted and positioned in the support scaffold sequentially. In certain embodiments, the bioprinter comprises multiple dual printheads, wherein multiple coated spheroids are lifted and positioned in the support scaffold simultaneously.

In certain embodiments, the method further comprises removing the support scaffold from the multi-spheroid tissue. For example, a support scaffold comprising a CNF hydrogel can be removed from the multi-spheroid tissue by treating the CNF hydrogel with a cellulase to degrade the CNF hydrogel while leaving the multi-spheroid tissue intact.

In certain embodiments, the method further comprises culturing the multi-spheroid tissue until the multi-spheroid tissue is mature. For example, the multi-spheroid tissue may be cultured in a suspension culture according to methods known in the art.

Systems and Computer Implemented Methods

The present disclosure provides systems and computer implemented methods which find use in practicing the subject methods. In some embodiments, the system may include: a processor programmed to control a bioprinter for producing a multi-spheroid tissue, as described herein. The processor may be programmed to perform steps of the computer implemented method comprising: (a) locating a microwell that contains a selected spheroid; (b) moving the dual printhead to a position over the microwell that contains the selected spheroid; (c) instructing the first nozzle to deposit the magnetic ink in the microwell containing the selected spheroid, wherein the selected spheroid is coated with the magnetic ink; (d) turning on the electromagnet, wherein the rod becomes magnetized; (e) lowering the magnetized rod over the selected spheroid until the magnetized rod magnetically attaches to the magnetic particles of the magnetic ink coating the selected spheroid; (f) raising the magnetized rod, wherein the selected spheroid is lifted out of the microwell; (g) moving the magnetized rod carrying the selected spheroid to a selected position in the reservoir; (h) lowering the magnetized rod over a selected location in the support scaffold; (i) turning off the electromagnet to demagnetize the rod, wherein the selected spheroid detaches from the demagnetized rod and is deposited at the selected location in the support scaffold; and (j) repeating (a)-(i), wherein additional selected spheroids are coated with the magnetic ink, lifted from the plurality of microwells with the magnetized rod, moved to the reservoir, and detached from the demagnetized rod and deposited at selected locations in the support scaffold to provide spatial control of the fusion of the plurality of spheroids to produce the multi-spheroid tissue. In some embodiments, the computer implemented method further comprises instructing the bioprinter to add cellulase to the support scaffold after step (j), wherein the support scaffold is removed from the multi-spheroid tissue.

The method can be implemented in digital electronic circuitry, or in computer software, firmware, or hardware. The disclosed and other embodiments can be implemented as one or more computer program products, i.e., one or more modules of computer program instructions encoded on a computer readable medium for execution by, or to control the operation of the bioprinter. The computer readable medium can be a machine-readable storage device, a machine-readable storage substrate, a memory device, a composition of matter effecting a machine-readable propagated signal, or any combination thereof.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

In a further aspect, the system for performing the computer implemented method, as described, may include a processor, a storage component (i.e., memory), a display component, and other components typically present in general purpose computers. In some embodiments, the processor is provided by a computer or handheld device (e.g., a cell phone or tablet). The storage component stores information accessible by the processor, including instructions that may be executed by the processor and data that may be retrieved, manipulated or stored by the processor.

The storage component includes instructions. For example, the storage component includes instructions for producing a multi-spheroid tissue, as described herein. The computer processor is coupled to the storage component and configured to execute the instructions stored in the storage component in order to locate a microwell that contains a selected spheroid coated with the magnetic ink from the plurality of microwells, ii) move the magnetic rod to lift the selected spheroid out of the microwell, wherein the magnetic rod magnetically attaches to the magnetic particles of the magnetic ink coating the spheroid, iii) move the magnetic rod carrying the selected spheroid to a selected position in the reservoir, wherein the selected spheroid is detached from the magnetic rod and deposited at a selected location within the support scaffold, and iv) repeat i)-iii), wherein additional spheroids coated with the magnetic ink are selected, located in the plurality of microwells, lifted from the plurality of microwells, moved to the reservoir, and positioned in any desired arrangement in the support scaffold to provide spatial control of the fusion of the plurality of spheroids to produce the multi-spheroid tissue, as described herein. The display component displays information regarding assembly of the multi-spheroid tissue.

The storage component may be of any type capable of storing information accessible by the processor, such as a hard-drive, memory card, ROM, RAM, DVD, CD-ROM, USB Flash drive, write-capable, and read-only memories. The processor may be any well-known processor, such as processors from Intel Corporation. Alternatively, the processor may be a dedicated controller such as an ASIC.

The instructions may be any set of instructions to be executed directly (such as machine code) or indirectly (such as scripts) by the processor. In that regard, the terms "instructions," "steps" and "programs" may be used interchangeably herein. The instructions may be stored in object code form for direct processing by the processor, or in any other computer language including scripts or collections of independent source code modules that are interpreted on demand or compiled in advance.

Data may be retrieved, stored or modified by the processor in accordance with the instructions. For instance, although the system is not limited by any particular data structure, the data may be stored in computer registers, in a relational database as a table having a plurality of different fields and records, XML documents, or flat files. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information which is used by a function to calculate the relevant data.

In certain embodiments, the processor and storage component may comprise multiple processors and storage components that may or may not be stored within the same physical housing. For example, some of the instructions and data may be stored on removable CD-ROM and others within a read-only computer chip. Some or all of the instructions and data may be stored in a location physically remote from, yet still accessible by, the processor. Similarly, the processor may comprise a collection of processors which may or may not operate in parallel. In some embodiments, a hardware accelerator is used. In some embodiments, imaging data is divided into chunks for processing by a plurality of graphics processing units (GPUs), field-programmable gate arrays (FPGAs), or tensor processing units (TPUs).

Components of systems for carrying out the presently disclosed methods are further described in the examples below.

Kits

Also provided are kits comprising a bioprinter for producing a multi-spheroid tissue, as described herein. The kit may also comprise media, buffers, magnetic nanoparticles, cells, and the like. In some embodiments, the kit comprises software comprising computer program instructions encoded on a computer readable medium for execution by, or to control the operation of the bioprinter.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

Spheroids

In certain embodiments, the spheroids comprise differentiated cells. In some embodiments, the spheroids comprise one or more types of somatic cells. The somatic cells may be human or non-human somatic cells. Somatic cells include, but are not limited to, exocrine secretory epithelial cells such as a Brunner's gland cell in the duodenum, insulated goblet cell of respiratory and digestive tracts, stomach cells such as foveolar cell (mucus secretion), a chief cell (pepsinogen secretion), parietal cell (hydrochloric acid secretion), and pancreatic acinar cell; a paneth cell of the small intestine, a type II pneumocyte of lung, a club cell of the lung; barrier cells such as a type I pneumocyte (lung), gall bladder epithelial cell, centroacinar cell (pancreas), intercalated duct cell (pancreas), and intestinal brush border cell (with microvilli); hormone-secreting cells such as an enteroendocrine cell, K cell, L cell, I cell, G cell, enterochromaffin cell, enterochromaffin-like cell, N cell, S cell, D cell, Mo cell, thyroid gland cells, thyroid epithelial cell, parafollicular cell, parathyroid gland cells, parathyroid chief cell, oxyphil cell, pancreatic islets (islets of Langerhans), alpha cell (secretes glucagon), beta cell (secretes insulin and amylin), delta cell (secretes somatostatin), epsilon cell (secretes ghrelin), pp cell (gamma cell), cells derived primarily from ectoderm such as exocrine secretory epithelial cells, salivary gland mucous cell, salivary gland serous cell, von Ebner's gland cell in tongue, mammary gland cell, lacrimal gland cell, ceruminous gland cell in ear, eccrine sweat gland dark cell, eccrine sweat gland clear cell, apocrine sweat gland cell, gland of moll cell in eyelid, sebaceous gland cell, and bowman's gland cell in nose; hormone-secreting cells such as anterior/intermediate pituitary cells, corticotropes, gonadotropes, lactotrophs, melanotropes, somatotrophs, thyrotropes, magnocellular neurosecretory cells, parvocellular neurosecretory cells, and chromaffin cells (adrenal gland); epithelial cells such as a keratinocyte, epidermal basal cell, melanocyte, trichocyte, medullary hair shaft cell, cortical hair shaft cell, cuticular hair shaft cell, Huxley's layer hair root sheath cell, Henle's layer hair root sheath cell, outer root sheath hair cell, surface epithelial cell of cornea, tongue, mouth, nasal cavity, distal anal canal, distal urethra, and distal vagina, basal cell (stem cell) of cornea, tongue, mouth, nasal cavity, distal anal canal, distal urethra, and distal vagina, intercalated duct cell (salivary glands), striated duct cell (salivary glands), lactiferous duct cell (mammary glands), ameloblast, oral cells such as an odontoblast and cementoblast; nervous system cells such as neurons, sensory transducer cells such as auditory inner hair cells of organ of *Corti*, auditory outer hair cells of organ of *Corti*, basal cells of olfactory epithelium, cold-sensitive primary sensory neurons, heat-sensitive primary sensory neurons, merkel cells of epidermis, olfactory receptor neurons, pain-sensitive primary sensory neurons, photoreceptor cells of retina in the eye such as photoreceptor rod cells, photoreceptor blue-sensitive cone cells of eye, photoreceptor green-sensitive cone cells of eye, and photoreceptor red-sensitive cone cells of eye; proprioceptive primary sensory neurons, touch-sensitive primary sensory neurons, chemoreceptor *glomus* cells of carotid body cell, outer hair cells of vestibular system of ear, inner hair cells of vestibular system of ear, taste receptor cells of taste bud, autonomic neuron cells, cholinergic neurons, adrenergic neural cells, peptidergic neural cells, sense organ and peripheral neuron supporting cells, inner pillar cells of organ of *Corti*, outer pillar cells of organ of *Corti*, inner phalangeal cells of organ of *Corti*, outer phalangeal cells of organ of *Corti*, border cells of organ of *Corti*, Hensen's cells of organ of *Corti*, vestibular apparatus supporting cells, taste bud supporting cells, olfactory epithelium supporting cells, olfactory ensheathing cells, schwann cells, satellite glial cells, enteric glial cells, central nervous system neurons and glial cells, interneurons basket cells, cartwheel cells, stellate cells, golgi cells, granule cells, lugaro cells, unipolar brush cells, martinotti cells, chandelier cells, Cajal-Retzius cells, double-bouquet cells, neuroglia form cells, retina horizontal cells, amacrine cells, starburst amacrine cells, spinal interneurons, renshaw cells, principal cells, spindle neurons, fork neurons, pyramidal cells, place cells, grid cells, speed cells, head direction cells, betz cells, stellate cells, boundary cells, bushy cells, Purkinje cells, medium spiny neurons, astrocytes, oligodendrocytes, ependymal cells, tanycytes, pituicytes, lens cells, anterior lens epithelial cell, crystallin-containing lens fiber cell; metabolism and storage cells such as adipocytes: white fat cell, brown fat cell, and liver lipocyte; secretory cells such as cells of the adrenal cortex, cells of the zona glomerulosa produce mineralocorticoids, cells of the zona *fasciculata* produce glucocorticoids, cells of the zona *reticularis* produce androgens, theca interna cell of ovarian follicle secreting estrogen, corpus *luteum* cell of ruptured ovarian follicle secreting progesterone, granulosa lutein cells, theca lutein cells, leydig cell of testes secreting testosterone, seminal vesicle cell, prostate gland cell, bulbourethral gland cell, Bartholin's gland cell, gland of littre cell, uterus endometrium cell, juxtaglomerular cell, macula *densa* cell of kidney, peripolar cell of kidney, and mesangial cell of kidney; urinary system cells such as parietal epithelial cell, podocyte, proximal tubule brush border cell, loop of henle thin segment cell, kidney distal tubule cell, kidney collecting duct cell, principal cell, intercalated cell, and transitional epithelium (lining urinary bladder); reproductive system cells such as duct cell (of seminal vesicle, prostate gland, etc.), efferent ducts cell epididymal principal cell, and epididymal basal cell; circulatory system cells, endothelial cells, extracellular matrix cells, planum semilunatum epithelial cell of vestibular system of ear, organ of *Corti* interdental epithelial cell, loose connective tissue fibroblasts, corneal fibroblasts (corneal keratocytes) tendon fibroblasts, bone marrow reticular tissue fibroblasts, other non-epithelial fibroblasts, pericyte, hepatic stellate cell (ito cell), nucleus pulposus cell of intervertebral disc, hyaline cartilage chondrocyte, fibrocartilage elastic chondrocyte, cartilage chondrocyte, osteoblast/osteocyte, osteoprogenitor cell, hyalocyte of vitreous body of eye, stellate cell of perilymphatic space of ear, and pancreatic stellate cell; contractile cells such as skeletal muscle cells, red skeletal muscle cell (slow twitch), white skeletal muscle cell (fast twitch), intermediate skeletal muscle cell, nuclear bag cell of muscle spindle, nuclear chain cell of muscle spindle, myosatellite cell (stem cell), cardiac muscle cells, cardiac muscle cell, SA node cell, Purkinje fiber cell, smooth muscle cell (various types) myoepithelial cell of iris myoepithelial cell of exocrine glands; blood and immune system cells such as an erythrocyte (red blood cell) and precursor erythroblasts megakaryocyte (platelet precursor) platelets, a monocyte, connective tissue macrophage (various types), epidermal langerhans cell osteoclast (in bone), dendritic cell (in lymphoid tissues), microglial cell (in central nervous system), neutrophil granulocyte and precursors (myeloblast, promyelocyte, myelocyte, metamyelocyte), an eosinophil granulocyte and precursors basophil granulocyte and precursors, a mast cell, helper T cell, regulatory T cell, cytotoxic T cell, natural killer T cell, B cell, plasma cell, natural killer cell, and hematopoietic stem cells; germ cells such as an oogonium/oocyte, spermatid, spermatocyte, spermatogonium cell, spermatozoon, nurse cell, granulosa cell, sertoli cell, and epithelial reticular cell; and interstitial cells such as interstitial kidney cells.

In certain embodiments, the spheroids comprise stem cells and/or progenitor cells, or are generated in part or whole using stem cells and/or progenitor cells. In some embodiments, the stem cells or progenitor cells are embryonic stem cells, embryonic germ cells, induced pluripotent stem cells, mesenchymal stem cells, bone marrow-derived mesenchymal stem cells, bone marrow-derived mesenchymal stromal cells, tissue plastic-adherent placental stem cells (PDACs), umbilical cord stem cells, amniotic fluid stem cells, amnion derived adherent cells (AMDACs), osteogenic placental adherent cells (OPACs), adipose stem cells, limbal stem cells, dental pulp stem cells, myoblasts, endothelial progenitor cells, neuronal stem cells, exfoliated teeth derived stem cells, hair follicle stem cells, dermal stem cells, parthenogenically derived stem cells, reprogrammed stem cells, amnion derived adherent cells, or side population stem cells. In certain other specific embodiments, said FPUs comprise hematopoietic stem cells or hematopoietic progenitor cells.

In some embodiments, the spheroids comprise cells derived from induced pluripotent stem cells. Induced pluripotent stem cells can be generated by reprogramming somatic cells into pluripotent stem cells followed by redifferentiation into a desired cell type. Somatic cells can be induced into forming pluripotent stem cells, for example, by treating them with reprograming factors such as Yamanaka factors, including but not limited to, OCT3, OCT4, SOX2, KLF4, c-MYC, NANOG, and LIN28 (see, e.g., Takahashi et al. (2007) Cell. 131(5):861-872; herein incorporated by reference in its entirety). The types of somatic cells that may be converted into IPSCs include, without limitation, peripheral blood mononuclear cells, fibroblasts, keratinocytes, epithelial cells, endothelial progenitor cells, mesenchymal stem cells, adipose derived stem cells, leukocytes, hematopoietic stem cells, bone marrow cells, and hepatocytes. Somatic cells are contacted with reprogramming factors in a combination and quantity sufficient to reprogram the cells to pluripotency. Reprogramming factors may be provided to the somatic cells individually or as a single composition, that is, as a premixed composition, of reprogramming factors. In some embodiments the reprogramming factors are provided as a plurality of coding sequences on a vector.

Methods for "introducing a cell reprogramming factor into somatic cells are not limited in particular, and known procedures can be selected and used as appropriate. For example, when a cell reprogramming factor as described above is introduced into somatic cells of the above-mentioned type in the form of proteins, such methods include ones using protein introducing reagents, fusion proteins with protein transfer domains (PTDs), electroporation, and microinjection. When a cell reprogramming factor as described above is introduced into somatic cells of the above-mentioned type in the form of nucleic acids encoding the cell reprogramming factor, a nucleic acid(s), such as cDNA(s), encoding the cell reprogramming factor can be inserted in an appropriate expression vector comprising a promoter that functions in somatic cells, which then can be introduced into somatic cells by procedures such as infection, lipofection, liposomes, electroporation, calcium phosphate coprecipitation, DEAE-dextran, microinjection, and electroporation. Examples of an "expression vector" include viral vectors, such as lentiviruses, retroviruses, adenoviruses, adeno-associated viruses, and herpes viruses; and expression plasmids for animal cells. For example, retroviral or Sendai virus (SeV) vectors are commonly used to introduce a nucleic acid(s) encoding a cell reprogramming factor as described above into somatic cells.

In some embodiments the IPSCs are derived from somatic cells obtained from normal individuals. In other embodiments the IPSCs are derived from somatic cells obtained from an individual comprising at least one allele encoding a mutation associated with a disease.

A sample comprising somatic cells is obtained from the subject. The somatic cells may include, without limitation, peripheral blood mononuclear cells, fibroblasts, keratinocytes, epithelial cells, endothelial progenitor cells, mesenchymal stem cells, adipose derived stem cells, leukocytes, hematopoietic stem cells, bone marrow cells, and hepatocytes, and other cell types capable of generating patient-derived IPSCs that can be differentiated into mature cells of a desired cell type, The biological sample comprising somatic cells is typically whole blood, buffy coat, peripheral blood mononucleated cells (PBMCS), skin, fat, or a biopsy, but can be any sample from bodily fluids, tissue or cells that contain suitable somatic cells. A biological sample can be obtained from a subject by conventional techniques. For example, blood can be obtained by venipuncture, and solid tissue samples can be obtained by surgical techniques according to methods well known in the art.

The IPSC-derived cells are harvested at an appropriate stage of development, which may be determined based on the expression of markers and phenotypic characteristics of the desired mature differentiated cell type. Cultures may be empirically tested by staining for the presence of markers of interest, by morphological determination, etc. The mature IPSC-derived cells may be purified prior to assembly into spheroids by positive selection for one or more markers expressed on mature cells. The cells are optionally enriched before or after the positive selection step by drug selection, panning, density gradient centrifugation, etc. In addition, a negative selection can be performed, where the selection is based on expression of one or more of the markers found on the somatic cells they are derived from (e.g., PBMCs, fibroblasts, epithelial cells, endothelial progenitor cells, leukocytes, hematopoietic stem cells, mesenchymal stem cells, bone marrow cells, hepatocytes), or neural progenitor cells, glial progenitor cells, neuroepithelial cells, and the like. Selection may utilize panning methods, magnetic particle selection, particle sorter selection, and the like. In some embodiments, the devices and methods described herein are used to assemble spheroids from one or more types of cells out of a culture containing a heterogeneous mixture of undifferentiated stem cells and differentiated and partially differentiated cells derived from stem cells.

In some embodiments, the cell is a neoplasia, tumor, or cancer cell. The cell may be derived from neoplasia, tumors, and cancers, including benign, malignant, metastatic and non-metastatic types, and including any stage (I, II, III, IV, or V) or grade (G1, G2, G3, etc.) of neoplasia, tumor, or cancer, or a neoplasia, tumor, cancer or metastasis that is progressing, worsening, stabilized or in remission. For example, the target cell may include a cell type from carcinomas, such as squamous cell carcinoma, adenocarcinoma, adenosquamous carcinoma, anaplastic carcinoma, large cell carcinoma, and small cell carcinoma. The target cell may be a cancerous cell from a cancer such as, but are not limited to, head and neck cancer, skin cancer, breast cancer, ovarian cancer, melanoma, pancreatic cancer, peripheral neuroma, glioblastoma, adrenocortical carcinoma, AIDS-related lymphoma, anal cancer, bladder cancer, meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma and other plasma cell neoplasms, mycosis fungoides and the Sezary syndrome, myelodysplastic syndromes, nasopharyngeal cancer, neuroblastoma, non-small cell lung cancer, small cell lung cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilm's tumor and other childhood kidney tumors.

Generally, cells are assembled into spheroids immediately or as soon as possible after they are obtained to avoid deterioration of the cells. It will be understood by one of ordinary skill in the art that in some cases, it is convenient to wait until multiple types of cells have been obtained prior to assembling the cells. Accordingly, in some cases, a cell of a particular cell type is stored until all appropriate cell types have been obtained. One of ordinary skill in the art will understand how to appropriately store a variety of different types of cells and any convenient method of storage may be used (e.g., refrigeration, freezing) that is appropriate for the particular cell type.

For a description of methods of generating and culturing spheroids, see, e.g., Ryu et al. (2019) Cells 8(12):1620, Gunti et al. (2021) Cancers (Basel) 13(4):874, Nath et al. (2016) Pharmacol Ther. 163:94-108, Cesarz et al. (2016) Stem Cells Int. 2016:9176357, Kasamkattil et al. (2022) Int J Mol Sci. 23(5):2530, Lin et al. (2008) Biotechnol J. 3(9-10):1172-84, Caprio et al. (2022) Acta Biomater. 24:S1742-7061 (22) 00620-1, and Shen et al. (2021) Micromachines (Basel) 12(1):96; herein incorporated by reference in their entireties.

Neural Spheroids/Organoids

Neural spheroids/organoids may include one or more types of neurons and/or glia. Neural spheroids/organoids may include any type of neuron including, without limitation, unipolar neurons, bipolar neurons, multipolar neurons, Golgi I neurons, Golgi II neurons, anaxonic neurons, pseudounipolar neurons, interneurons, motor neurons, sensory neurons, afferent neurons, efferent neurons, cholinergic neurons, GABAergic neurons, glutamatergic neurons, dopaminergic neurons, serotonergic neurons, histaminergic neurons, Purkinje cells, spiny projection neurons, Renshaw cells, and granule cells, or a combination thereof. Additionally, neural spheroids/organoids may include any type of glia including, without limitation, glia such as astrocytes, oligodendrocytes, ependymal cells, microglia, and NG2 glia, or a combination thereof.

In certain embodiments, a three-dimensional spheroid/organoid is assembled from multiple types of neurons and/or glia. For example, the spheroid/organoid may be assembled from one or more types of excitatory neurons and/or inhibitory neurons and glia found in a brain region of interest. A spheroid/organoid may include interneurons, motor neurons, sensory neurons, afferent neurons, efferent neurons. inhibitory neurons, or excitatory neurons, or a combination thereof. In some embodiments, the spheroid/organoid includes glutamatergic neurons, cholinergic neurons, GABAergic neurons, dopaminergic neurons, serotonergic neurons, or histaminergic neurons, or a combination thereof. In some embodiments a spheroid/organoid includes glia such as astrocytes, oligodendrocytes, ependymal cells, microglia, or NG2 glia, or a combination thereof.

Neural spheroids/organoids and assembloids thereof may be designed to mimic one or more brain regions of interest in the cerebrum, cerebellum, or brainstem regions of the brain. Brain regions of interest may include, without limitation, the basal ganglia, striatum, medulla, pons, midbrain, medulla oblongata, hypothalamus, thalamus, epithalamus, amygdala, superior colliculus, cerebral cortex, neocortex, allocortex, hippocampus, claustrum, olfactory bulb, frontal lobe, temporal lobe, parietal lobe, occipital lobe, caudate-putamen, external globus pallidus, internal globus pallidus, subthalamic nucleus, substantia nigra, thalamus, and motor cortex regions of the brain.

In some embodiments, neural spheroids/organoids are produced from neurons and glia derived from induced pluripotent stem cells (IPSCs). Differentiation of IPSCs into neurons (IPSC-derived neurons) and glia (IPSC-derived glia) may be promoted by using lineage-determining transcription factors and various growth factors and other differentiation agents. For example, the master neuronal transcriptional regulator neurogenin-2 (NGN2) in combination with brain-derived neurotrophic factor (BDNF) and neurotrophin-3 (NT3) promotes differentiation of iPSCs into glutamatergic cortical neurons. Expression of the transcription factors Islet-1 (ISL1) and LIM Homeobox 3 (LHX3) along with NGN2 promotes differentiation of IPSCs into motor neurons. Expression of the transcription factors achuete-scute family bHLH transcription factor 1 (ASCL1) and distal-less homeobox 2 (DLX2) induces the generation of GABAergic neurons. Growth factors such as epidermal growth factor (EGF) and basic fibroblast growth factor (FGFb) can be used to promote differentiation of IPSCs into astrocytes. Macrophage colony stimulating factor 1 (MCSF), interleukin-34 (IL-34), transforming growth factor beta 1 (TGFβ-1), CD200 and C-X3-C motif chemokine ligand 1 (CX3CL1) can be used to promote differentiation of IPSCs into microglia. Ventral midbrain astrocytes can be generated with Chir99021 and purmorphamine. Dopaminergic neurons can be generated using the proneural factor Ascl1 in combination with mesencephalic factors Lmx1a and Nurr1. Co-delivery of additional midbrain transcription factors En1, FoxA2, and Pitx3 produces dopaminergic neurons having midbrain characteristics. See, e.g., the Examples and differentiation protocols described by Reyes et al. (2008) J Neurosci. 28 (48): 12622-12631, Zhang et al. (2013) Neuron 78(5):785-98, Hester et al. (2011) Mol. Ther. 19:1905-1912, Fernandopulle et al. (2018) Curr. Protoc. Cell Biol. 79 (1): e51, Krencik et al. (2011) Nat. Protoc. 6:1710-1717, Yang et al. (2017) Nat. Methods 14:621-628, Muffat et al. (2016) Nat. Med. 22:1358-1367, Pandya et al. (2017) Nat. Neurosci. 20:753-759, Douvaras et al. (2017) Stem *Cell Reports* 8:1516-1524, Abud et al. (2017) Neuron 94, 278-293 e279, Abud et al. (2017) Neuron 94(2):278-293.e9, Krencik et al. (2011) Nat. Protoc. 6 (11): 1710-1717, Ng et al. (2021) Stem *Cell Reports* 16 (7): 1763-1776; herein incorporated by reference in their entireties. However, any suitable method of inducing differentiation of IPSCs into neurons and glia may be used.

The IPSC-derived neurons and glia are harvested at an appropriate stage of development, which may be determined based on the expression of markers and phenotypic characteristics of the desired mature differentiated cell type. Cultures may be empirically tested by staining for the presence of the markers of interest, by morphological determination, etc. for example, astrocytes can be identified by markers specific for cells of the astrocyte lineage, including, without limitation, GFAP, ALDH1L1, AQP4, and EAAT1-2. Neurons can be identified by markers, including without limitation, enolase 2/NSE, NeuN, MAP2, beta-Ill tubulin, neurofilament light, neurofilament medium, neurofilament heavy, and GAP-43. The mature IPSC-derived neurons and glia may be purified prior to assembly into organoids by positive selection for one or more markers expressed on mature neurons or glia, respectively. The cells are optionally enriched before or after the positive selection step by drug selection, panning, density gradient centrifugation, etc. In addition, a negative selection can be performed, where the selection is based on expression of one or more of the markers found on the somatic cells they are derived from (e.g., PBMCs, fibroblasts, epithelial cells, endothelial progenitor cells, leukocytes, hematopoietic stem cells, mesenchymal stem cells, bone marrow cells, hepatocytes), or neural progenitor cells, glial progenitor cells, neuroepithelial cells, and the like. Selection may utilize panning methods, magnetic particle selection, particle sorter selection, and the like.

In some embodiments, dorsal brain region specific organoids are generated by differentiating IPSCs in the presence of the dual SMAD inhibitors, LDN-193189 and SB-431542, followed by culturing in a neural medium supplemented with growth factors such as EGF, FGF-2, BDNF, and NT3. In some embodiments, ventral brain region specific organoids are generated by differentiating IPSCs following a similar protocol to that used for generation of dorsal neural organoids except with addition of inhibitor of Wnt production 2 (IWP2), and sonic hedgehog signaling agonist (SAG). See, e.g., Example 1 and Birey et al. (2017) Nature 545:54-59, Miura et al. (2022) Nature Protocols 17:15 35, and Yoon et al. (2019) Nat. Methods 16:75-78; herein incorporated by reference in their entireties.

Genome Modification to Introduce Disease-Relevant Genetic Changes

Disease-relevant mutations can be introduced into the genome of cells in spheroids using any method known in the art to produce an assembled three-dimensional spheroid disease model. In some embodiments, a CRISPR/Cas system is used to make genetic changes to a gene of interest in mature cells or stem cells or progenitor cells from which they are derived to produce a spheroid useful for disease modeling and drug screening. For example, a CRISPR/Cas system can be used to delete, inactivate, or mutate a gene, or eliminate or reduce gene expression or protein activity. Genome modification can be performed, for example, using homology directed repair (HDR) with a donor polynucleotide comprising a sequence comprising an intended genome edit flanked by a pair of homology arms responsible for targeting the donor polynucleotide to the target locus to be edited in a cell. The donor polynucleotide typically comprises a 5' homology arm that hybridizes to a 5' genomic target sequence and a 3' homology arm that hybridizes to a 3' genomic target sequence. The homology arms are referred to herein as 5' and 3' (i.e., upstream and downstream) homology arms, which relates to the relative position of the homology arms to the nucleotide sequence comprising the intended edit within the donor polynucleotide. The 5' and 3' homology arms hybridize to regions within the target locus in the genomic DNA to be modified, which are referred to herein as the "5' target sequence" and "3' target sequence," respectively.

The homology arm must be sufficiently complementary for hybridization to the target sequence to mediate homologous recombination between the donor polynucleotide and genomic DNA at the target locus. For example, a homology arm may comprise a nucleotide sequence having at least about 80-100% sequence identity to the corresponding genomic target sequence, including any percent identity within this range, such as at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity thereto, wherein the nucleotide sequence comprising the intended edit is integrated into the genomic DNA by HDR at the genomic target locus recognized (i.e., sufficiently complementary for hybridization) by the 5' and 3' homology arms.

In certain embodiments, the corresponding homologous nucleotide sequences in the genomic target sequence (i.e., the "5' target sequence" and "3' target sequence") flank a specific site for cleavage and/or a specific site for introducing the intended edit. The distance between the specific cleavage site and the homologous nucleotide sequences (e.g., each homology arm) can be several hundred nucleotides. In some embodiments, the distance between a homology arm and the cleavage site is 200 nucleotides or less (e.g., 0, 10, 20, 30, 50, 75, 100, 125, 150, 175, and 200 nucleotides). In most cases, a smaller distance may give rise to a higher gene targeting rate. In a preferred embodiment, the donor polynucleotide is substantially identical to the target genomic sequence, across its entire length except for the sequence changes to be introduced to a portion of the genome that encompasses both the specific cleavage site and the portions of the genomic target sequence to be altered.

A homology arm can be of any length, e.g., 10 nucleotides or more, 50 nucleotides or more, 100 nucleotides or more, 250 nucleotides or more, 300 nucleotides or more, 350 nucleotides or more, 400 nucleotides or more, 450 nucleotides or more, 500 nucleotides or more, 1000 nucleotides (1 kb) or more, 5000 nucleotides (5 kb) or more, 10000 nucleotides (10 kb) or more, etc. In some instances, the 5' and 3' homology arms are substantially equal in length to one another, e.g., one may be 30% shorter or less than the other homology arm, 20% shorter or less than the other homology arm, 10% shorter or less than the other homology arm, 5% shorter or less than the other homology arm, 2% shorter or less than the other homology arm, or only a few nucleotides less than the other homology arm. In other instances, the 5' and 3' homology arms are substantially different in length from one another, e.g., one may be 40% shorter or more, 50% shorter or more, sometimes 60% shorter or more, 70% shorter or more, 80% shorter or more, 90% shorter or more, or 95% shorter or more than the other homology arm.

The donor polynucleotide is used in combination with an RNA-guided nuclease, which is targeted to a particular genomic sequence (i.e., genomic target sequence to be modified) by a guide RNA (gRNA). A target-specific guide RNA comprises a nucleotide sequence that is complementary to a genomic target sequence, and thereby mediates binding of the nuclease-gRNA complex by hybridization at the target site. For example, the gRNA can be designed with a sequence complementary to a target sequence in a gene of interest. In some embodiments, the gRNA is designed with a sequence complementary to a specific mutation to target the nuclease-gRNA complex to the site of a mutation in a cell. The mutation may comprise an insertion, a deletion, or a substitution. For example, the mutation may include a single nucleotide variation, gene fusion, translocation, inversion, duplication, frameshift, missense, nonsense, or other mutation. The targeted minor allele may be a common genetic variant or a rare genetic variant. In certain embodiments, the gRNA is designed to selectively bind to a minor allele with single base-pair discrimination, for example, to allow binding of the nuclease-gRNA complex to a single nucleotide polymorphism (SNP). In particular, the gRNA may be designed to target disease-relevant mutations of interest for the purpose of genome editing to delete or deactivate the gene in a neuron or glia.

In certain embodiments, the RNA-guided nuclease used for genome modification is a CRISPR system Cas nuclease. Any RNA-guided Cas nuclease capable of catalyzing site-directed cleavage of DNA to allow integration of donor polynucleotides by the HDR mechanism can be used in genome editing, including CRISPR system type I, type II, or type III Cas nucleases. Examples of Cas proteins include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, Cas12a (Cpf1), Cas12b (C2c1), Cas12c (C2c3), Cas12d (CasY), Cas12e (CasX), CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

In certain embodiments, a type II CRISPR system Cas9 endonuclease is used. Cas9 nucleases from any species, or biologically active fragments, variants, analogs, or derivatives thereof that retain Cas9 endonuclease activity (i.e., catalyze site-directed cleavage of DNA to generate double-strand breaks) may be used to perform genome modification as described herein. The Cas9 need not be physically derived from an organism, but may be synthetically or recombinantly produced. Cas9 sequences from a number of bacterial species are well known in the art and listed in the National Center for Biotechnology Information (NCBI) database. See, for example, NCBI entries for Cas9 from: *Streptococcus pyogenes* (WP_002989955, V WP_038434062, WP_011528583); *Campylobacter jejuni* (WP_022552435, YP_002344900), *Campylobacter coli* (WP_060786116); *Campylobacter fetus* (WP_059434633); *Corynebacterium ulcerans* (NC_015683, NC_017317); *Corynebacterium diphtheria* (NC_016782, NC_016786); *Enterococcus faecalis* (WP_033919308); Spiroplasma syrphidicola (NC_021284); *Prevotella intermedia* (NC_017861); Spiroplasma *taiwanense* (NC_021846); *Streptococcus* iniae (NC_021314); Belliella *baltica* (NC_018010); Psychroflexus torquis/(NC_018721); *Streptococcus thermophilus* (YP_820832), *Streptococcus mutans* (WP_061046374, WP_024786433); *Listeria innocua* (NP_472073); *Listeria monocytogenes* (WP_061665472); *Legionella pneumophila* (WP_062726656); *Staphylococcus aureus* (WP_001573634); *Francisella tularensis* (WP_032729892, WP_014548420), *Enterococcus faecalis* (WP_033919308); *Lactobacillus rhamnosus* (WP_048482595, WP_032965177); and *Neisseria meningitidis*

(WP_061704949, YP_002342100); all of which sequences (as entered by the date of filing of this application) are herein incorporated by reference. Any of these sequences or a variant thereof comprising a sequence having at least about 70-100% sequence identity thereto, including any percent identity within this range, such as 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity thereto, can be used for genome editing, as described herein. See also Fonfara et al. (2014) Nucleic Acids Res. 42(4):2577-90; Kapitonov et al. (2015) J. Bacteriol. 198(5):797-807, Shmakov et al. (2015) Mol. Cell. 60(3):385-397, and Chylinski et al. (2014) Nucleic Acids Res. 42(10):6091-6105); for sequence comparisons and a discussion of genetic diversity and phylogenetic analysis of Cas9.

The CRISPR-Cas system naturally occurs in bacteria and archaea where it plays a role in RNA-mediated adaptive immunity against foreign DNA. The bacterial type II CRISPR system uses the endonuclease, Cas9, which forms a complex with a guide RNA (gRNA) that specifically hybridizes to a complementary genomic target sequence, where the Cas9 endonuclease catalyzes cleavage to produce a double-stranded break. Targeting of Cas9 typically further relies on the presence of a 5' protospacer-adjacent motif (PAM) in the DNA at or near the gRNA-binding site.

The genomic target site will typically comprise a nucleotide sequence that is complementary to the gRNA, and may further comprise a protospacer adjacent motif (PAM). In certain embodiments, the target site comprises 20-30 base pairs in addition to a 3 base pair PAM. Typically, the first nucleotide of a PAM can be any nucleotide, while the two other nucleotides will depend on the specific Cas9 protein that is chosen. Exemplary PAM sequences are known to those of skill in the art and include, without limitation, NNG, NGN, NAG, and NGG, wherein N represents any nucleotide. In certain embodiments, the allele targeted by a gRNA comprises a mutation that creates a PAM within the allele, wherein the PAM promotes binding of the Cas9-gRNA complex to the allele.

In certain embodiments, the gRNA is 5-50 nucleotides, 10-30 nucleotides, 15-25 nucleotides, 18-22 nucleotides, or 19-21 nucleotides in length, or any length between the stated ranges, including, for example, 10, 11, 12, 13, 14, 15, 16, 17, 18, 19, 20, 21, 22, 23, 24, 25, 26, 27, 28, 29, 30, 31, 32, 33, 34, or 35 nucleotides in length. The guide RNA may be a single guide RNA comprising crRNA and tracrRNA sequences in a single RNA molecule, or the guide RNA may comprise two RNA molecules with crRNA and tracrRNA sequences residing in separate RNA molecules.

In another embodiment, the CRISPR nuclease from *Prevotella* and *Francisella* 1 (Cpf1, also known as Cas12a) is used. Cpf1 is another class II CRISPR/Cas system RNA-guided nuclease with similarities to Cas9 and may be used analogously. Unlike Cas9, Cpf1 does not require a tracrRNA and only depends on a crRNA in its guide RNA, which provides the advantage that shorter guide RNAs can be used with Cpf1 for targeting than Cas9. Cpf1 is capable of cleaving either DNA or RNA. The PAM sites recognized by Cpf1 have the sequences 5'-YTN-3' (where "Y" is a pyrimidine and "N" is any nucleobase) or 5'-TTN-3', in contrast to the G-rich PAM site recognized by Cas9. Cpf1 cleavage of DNA produces double-stranded breaks with a sticky-ends having a 4 or 5 nucleotide overhang. For a discussion of Cpf1, see, e.g., Ledford et al. (2015) Nature. 526(7571):17-17, Zetsche et al. (2015) Cell. 163(3):759-771, Murovec et al. (2017) Plant Biotechnol. J. 15(8):917-926, Zhang et al.

(2017) Front. Plant Sci. 8:177, Fernandes et al. (2016) Postepy Biochem. 62(3):315-326; herein incorporated by reference.

Cas12b (C2c1) is another class II CRISPR/Cas system RNA-guided nuclease that may be used. C2c1, similarly to Cas9, depends on both a crRNA and tracrRNA for guidance to target sites. For a description of Cas12b, see, e.g., Shmakov et al. (2015) Mol Cell. 60(3):385-397, Zhang et al. (2017) Front Plant Sci. 8:177; herein incorporated by reference.

In yet another embodiment, an engineered RNA-guided FokI nuclease may be used. RNA-guided FokI nucleases comprise fusions of inactive Cas9 (dCas9) and the FokI endonuclease (FokI-dCas9), wherein the dCas9 portion confers guide RNA-dependent targeting on FokI. For a description of engineered RNA-guided FokI nucleases, see, e.g., Havlicek et al. (2017) Mol. Ther. 25(2):342-355, Pan et al. (2016) Sci Rep. 6:35794, Tsai et al. (2014) Nat Biotechnol. 32(6):569-576; herein incorporated by reference.

An RNA-guided nuclease can be provided in the form of a protein, such as the nuclease complexed with a gRNA, or provided by a nucleic acid encoding the RNA-guided nuclease, such as an RNA (e.g., messenger RNA) or DNA (expression vector). In some embodiments, the RNA-guided nuclease and the gRNA are both provided by vectors. Both can be expressed by a single vector or separately on different vectors. The vector(s) encoding the RNA-guided nuclease an gRNA may be included in a CRISPR expression system to target a gene of interest in neurons or glia.

Codon usage may be optimized to improve production of an RNA-guided nuclease in a particular cell or organism. For example, a nucleic acid encoding an RNA-guided nuclease or reverse transcriptase can be modified to substitute codons having a higher frequency of usage in a human cell, a non-human cell, a mammalian cell, a rodent cell, a mouse cell, a rat cell, or any other host cell of interest, as compared to the naturally occurring polynucleotide sequence. When a nucleic acid encoding the RNA-guided nuclease is introduced into cells (e.g., neurons or glia), the protein can be transiently, conditionally, or constitutively expressed in the cell.

In another embodiment, CRISPR interference (CRISPRi) is used to repress gene expression. CRISPRi is performed with a complex of a catalytically inactive Cas9 (dCas9) with a guide RNA that targets the gene of interest. An engineered nuclease-deactivated Cas9 (dCas9) is used to allow sequence-specific targeting without cleavage. Nuclease-deactivated forms of Cas9 may be engineered by mutating catalytic residues at the active site of Cas9 to destroy nuclease activity. Any such nuclease deficient Cas9 protein from any species may be used as long as the engineered dCas9 retains gRNA-mediated sequence-specific targeting. In particular, the nuclease activity of Cas9 from *Streptococcus pyogenes* can be deactivated by introducing two mutations (D10A and H841A) in the RuvC1 and HNH nuclease domains. Other engineered dCas9 proteins may be produced by similarly mutating the corresponding residues in other bacterial Cas9 isoforms. For a description of engineered nuclease-deactivated forms of Cas9, see, e.g., Qi et al. (2013) Cell 152:1173-1183, Dominguez et al. (2016) Nat. Rev. Mol. Cell. Biol. 17(1):5-15; herein incorporated by reference in their entireties.

The dCas9 protein can be designed to target a gene of interest by altering its guide RNA sequence. A target-specific single guide RNA (sgRNA) comprises a nucleotide sequence that is complementary to a target site, and thereby mediates binding of the dCas9-sgRNA complex by hybridization at the target site. CRISPRi can be used to sterically repress transcription by blocking either transcriptional initiation or elongation by designing a sgRNA with a sequence complementary to a promoter or exonic sequence. The sgRNA may be complementary to the non-template strand or the template strand, but preferably is complementary to the non-template strand to more strongly repress transcription.

The target site will typically comprise a nucleotide sequence that is complementary to the sgRNA, and may further comprise a protospacer adjacent motif (PAM). In certain embodiments, the target site comprises 20-30 base pairs in addition to a 3 base pair PAM. Typically, the first nucleotide of a PAM can be any nucleotide, while the two other nucleotides will depend on the specific Cas9 protein that is chosen. Exemplary PAM sequences are known to those of skill in the art and include, without limitation, NNG, NGN, NAG, and NGG, wherein N represents any nucleotide.

In certain embodiments, the sgRNA comprises 5-50 nucleotides, 10-30 nucleotides, 15-25 nucleotides, 18-22 nucleotides, 19-21 nucleotides, and any length between the stated ranges, including, for example, 10, 11, 12, 13, 14, 15, 16, 17, 18, 19, 20, 21, 22, 23, 24, 25, 26, 27, 28, 29, or 30 nucleotides.

The sgRNAs are readily synthesized by standard techniques, e.g., solid phase synthesis via phosphoramidite chemistry, as disclosed in U.S. Pat. Nos. 4,458,066 and 4,415,732, incorporated herein by reference; Beaucage et al., *Tetrahedron* (1992) 48:2223-2311; and Applied Biosystems User Bulletin No. 13 (1 Apr. 1987). Other chemical synthesis methods include, for example, the phosphotriester method described by Narang et al., *Meth. Enzymol.* (1979) 68:90 and the phosphodiester method disclosed by Brown et al., *Meth. Enzymol.* (1979) 68:109.

In some embodiments, the dCas9 is fused to a transcriptional repressor domain capable of further repressing transcription of the gene of interest, e.g., by inducing heterochromatinization. For example, a Krüppel associated box (KRAB) can be fused to dCas9 to repress transcription of a target gene in human cells (see, e.g., Gilbert et al. (2013) Cell. 154(2):442-45, O'Geen et al. (2017) Nucleic Acids Res. 45 (17): 9901-9916; herein incorporated by reference).

Alternatively, dCas9 can be used to introduce epigenetic changes that reduce expression of a gene of interest by fusion of dCas9 to an epigenetic modifier such as a chromatin-modifying epigenetic enzyme. The promoter for the gene of interest can be silenced, for example, by methylation or acetylation (e.g., histone H3 lysine 9 [H3K9] methylation, histone H3 lysine 27 [H3K27] methylation, and/or DNA methylation). For example, fusion of dCas9 to a DNA methyltransferase such as DNA methyltransferase 3 alpha (DNMT3A) or a chimeric Dnmt3a/Dnmt3L methyltransferase (DNMT3A3L) allows targeted DNA methylation. Fusion of dCas9 to histone demethylase LSD1 allows targeted histone demethylation (see, e.g., Liu et al. (2016) Cell 167(1):233-247, Lo et al. (2017) F1000Res. 6. pii: F1000 Faculty Rev-747, and Stepper et al. (2017) Nucleic Acids Res. 45(4):1703-1713; herein incorporated by reference).

In yet other embodiments, an RNA-targeting CRISPR-Cas13 system is used to perform RNA interference to reduce expression of a gene of interest. Members of the Cas13 family are RNA-guided RNases containing two HEPN domains having RNase activity. In particular, Cas13a (C2c2), Cas13b (C2c6), and Cas13d can be used for RNA knockdown. Cas13 proteins can be made to target and cleave transcribed RNA using a gRNA with complementarity to the target transcript sequence. The gRNA is typically about 64 nucleotides in length with a short hairpin crRNA and a 28-30 nucleotide spacer that is complementary to the target site on the RNA transcript. Cas13 recognition and cleavage of a target transcript results in degradation of the transcript as well as nonspecific degradation of any nearby transcripts. See, e.g., Abudayyeh et al. (2017) Nature 550:280-284, Hameed et al. (2019) Microb. Pathog. 133:103551, Wang et al. (2019) Biotechnol Adv. 37(5):708-729, Aman et al. (2018) Viruses 10 (12). pii: E732, and Zhang et al. (2018) Cell 175(1):212-223; herein incorporated by reference.

Screening Assays

Multi-spheroid tissues, produced by the methods described herein, can be subjected to a plurality of candidate agents or other therapeutic intervention. Candidate agents include, without limitation, small molecules, i.e., drugs, genetic constructs that increase or decrease expression of an RNA of interest, CRISPR systems, optogenetic perturbation, electrical changes, and the like. Methods are also provided for determining the activity of a candidate agent on a disease-relevant cell, the method comprising contacting one or more cells of the spheroid comprising at least one allele encoding a mutation associated with a disease associated or cellular dysfunction with the candidate agent; and determining the effect of the agent on morphologic, genetic or functional parameters. In screening assays multi-spheroid tissues in culture may be tested with one or a panel of cellular environments, where the cellular environment includes one or more of: electrical stimulation including alterations in ionicity, stimulation with a candidate agent of interest, contact with other cells, contact with infectious agents, e.g. bacterial, viral, fungal, or parasitic infectious agents, and the like, and where cells may vary in genotype, in prior exposure to an environment of interest, in the dose of agent that is provided, etc. Usually at least one control is included, for example, a negative control and a positive control. Culture of multi-spheroid tissues is typically performed in a sterile environment, for example, at 37° C. in an incubator containing a humidified 92-95% air/5-8% $CO_2$ atmosphere. Cell culture may be carried out in nutrient mixtures containing undefined biological fluids such as fetal calf serum, or media which is fully defined and serum free. The effect of the altering of the environment is assessed by monitoring multiple output parameters, including morphological, functional and genetic changes.

For screening of neural assembloids, examples of analytic methods include, without limitation, assessing the synaptic integration of migrated neurons by using array tomography to detect pre- and post-synaptic proteins. To further examine synaptic puncta 'synaptograms' consisting of a series of high-resolution sections through a single synapse may be obtained. Electrophysiology measurements including voltage clamp recordings of synaptic responses can be performed on slices of the spheroids/organoids.

Live imaging of cells, including during cell migration, may be performed and cells modified to express a detectable marker. Calcium sensitive dyes can be used, e.g., Fura-2 calcium imaging; Fluo-4 calcium imaging, GCaMP6 calcium imaging, voltage imaging using voltage indicators such as voltage-sensitive dyes (e.g., di-4-ANEPPS, di-8-ANEPPS, and RH237) and/or genetically-encoded voltage indicators (e.g., ASAP1, Archer) can be used on an intact multi-spheroid tissue or spheroids/organoids or on cells isolated therefrom.

Methods of analysis at the single cell level are also of interest, e.g., as described above: live imaging (including confocal or light-sheet microscopy), single cell gene expression or single cell RNA sequencing, calcium imaging, immunocytochemistry, patch-clamping, flow cytometry and the like. Various parameters can be measured to determine the effect of a drug or treatment on a multi-spheroid tissue, or spheroids or cells derived therefrom.

Parameters include quantifiable components of cells, particularly components that can be accurately measured, desirably in a high throughput system. A parameter can also be any cell component or cell product including cell surface determinant, receptor, protein or conformational or post-translational modification thereof, lipid, carbohydrate, organic or inorganic molecule, nucleic acid, e.g., mRNA, DNA, etc. or a portion derived from such a cell component or combinations thereof. Although most parameters will provide a quantitative readout, in some instances a semi-quantitative or qualitative result will be acceptable. Read-outs may include a single determined value, or may include mean, median value or the variance, etc. Variability is expected and a range of values for each of the set of test parameters will be obtained using standard statistical methods with a common statistical method used to provide single values.

Parameters of interest include detection of cytoplasmic, cell surface or secreted biomolecules, frequently biopolymers, e.g., polypeptides, polysaccharides, polynucleotides, lipids, etc. Cell surface and secreted molecules are a preferred parameter type as these mediate cell communication and cell effector responses and can be more readily assayed. In one embodiment, parameters include specific epitopes. Epitopes are frequently identified using specific monoclonal antibodies or receptor probes. In some cases, the molecular entities comprising the epitope are from two or more substances and comprise a defined structure; examples include combinatorically determined epitopes associated with heterodimeric integrins. A parameter may be detection of a specifically modified protein or oligosaccharide. A parameter may be defined by a specific monoclonal antibody or a ligand or receptor binding determinant.

Candidate agents of interest are biologically active agents that encompass numerous chemical classes, primarily organic molecules, which may include organometallic molecules, inorganic molecules, genetic sequences, etc. In particular, candidate drugs, select therapeutic antibodies and protein-based therapeutics with preferred biological response functions can be evaluated. Candidate agents comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, anti-inflammatory agents, neurotransmitters, hormones or hormone antagonists, ion channel modifiers, and neuroactive agents. Exemplary pharmaceutical agents include those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Cardiovascular Drugs; Vitamins, Dermatology; and Toxicology, all incorporated herein by reference.

Test compounds may include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g., ground water, sea water, mining waste, etc.; biological samples, e.g., lysates prepared from crops, tissue samples, etc.; manufacturing samples, e.g., time course during preparation of pharmaceuticals; as well as libraries of compounds prepared for analysis; and the like. Samples of interest include compounds being assessed for potential therapeutic value, i.e., drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g., under nitrogen, frozen, or a combination thereof. The volume of sample used is sufficient to allow for measurable detection, usually from about 0.1 to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As used herein, the term "genetic agent" refers to polynucleotides and analogs thereof, which agents are tested in the screening assays by addition of the genetic agent to a cell. The introduction of the genetic agent results in an alteration of the total genetic composition of the cell. Genetic agents such as DNA can result in an experimentally introduced change in the genome of a cell, generally through the integration of the sequence into a chromosome, for example using CRISPR mediated genomic engineering (see for example Shmakov et al. (2017) Nature Reviews Microbiology 15:169). Genetic changes can also be transient, where the exogenous sequence is not integrated but is maintained as an episomal agents. Genetic agents, such as antisense oligonucleotides, can also affect the expression of proteins without changing the cell's genotype, by interfering with the transcription or translation of mRNA. The effect of a genetic agent is to increase or decrease expression of one or more gene products in the cell.

Introduction of an expression vector encoding a polypeptide can be used to express the encoded product in cells lacking the sequence, or to over-express the product. Various promoters can be used that are constitutive or subject to external regulation, where in the latter situation, one can turn on or off the transcription of a gene. These coding sequences may include full-length cDNA or genomic clones, fragments derived therefrom, or chimeras that combine a naturally occurring sequence with functional or structural domains of other coding sequences. Alternatively, the introduced sequence may encode an anti-sense sequence; be an anti-sense oligonucleotide; RNAi, encode a dominant negative mutation, or dominant or constitutively active mutations of native sequences; altered regulatory sequences, etc.

Antisense and RNAi oligonucleotides can be chemically synthesized by methods known in the art. Preferred oligonucleotides are chemically modified from the native phosphodiester structure, in order to increase their intracellular stability and binding affinity. A number of such modifications have been described in the literature, which alter the chemistry of the backbone, sugars or heterocyclic bases. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity, e.g., morpholino oligonucleotide analogs.

Agents are screened for biological activity by adding the agent to at least one multi-spheroid tissue and usually a plurality of multi-spheroid tissues, in one or in a plurality of environmental conditions, e.g., following stimulation with an agonist, following electric or mechanical stimulation, etc. The change in parameter readout in response to the agent is measured, desirably normalized, and the resulting screening results may then be evaluated by comparison to reference screening results, e.g., with cells having other mutations of interest, normal astrocytes, astrocytes derived from other family members, and the like. The reference screening results may include readouts in the presence and absence of different environmental changes, screening results obtained with other agents, which may or may not include known drugs, etc.

The agents are conveniently added in solution, or readily soluble form, to the medium used in culturing a multi-spheroid tissue. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the multi-spheroid tissue, followed by the second. In a single solution method, a bolus of the test compound is added to the volume of medium surrounding the multi-spheroid tissue. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus, preferred formulations consist essentially of a biologically active compound and a physiologically acceptable carrier, e.g., water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e., at zero concentration or below the level of detection of the agent or at or below the concentration of agent that does not give a detectable change in the phenotype.

Various methods can be utilized for quantifying the presence of selected parameters, in addition to the functional parameters described above. For measuring the amount of a molecule that is present, a convenient method is to label a molecule with a detectable moiety, which may be fluorescent, luminescent, radioactive, enzymatically active, etc., particularly a molecule specific for binding to the parameter with high affinity fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to fluoresce, e.g., by expressing them as green fluorescent protein chimeras inside cells (for a review see Jones et al. (1999) Trends Biotechnol. 17(12):477-81). Thus, antibodies can be genetically modified to provide a fluorescent dye as part of their structure Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. These techniques utilize specific antibodies as reporter molecules, which are particularly useful due to their high degree of specificity for attaching to a single molecular target. U.S. Pat. No. 4,568,649 describes ligand detection systems, which employ scintillation counting. These techniques are particularly useful for protein or modified protein parameters or epitopes, or carbohydrate determinants. Cell readouts for proteins and other cell determinants can be obtained using fluorescent or otherwise tagged reporter molecules. Cell based ELISA or related non-enzymatic or fluorescence-based methods enable measurement of cell surface parameters and secreted parameters. Capture ELISA and related non-enzymatic methods usually employ two specific antibodies or reporter molecules and are useful for measuring parameters in solution. Flow cytometry methods are useful for measuring cell surface and intracellular parameters, as well as shape change and granularity and for analyses of beads used as antibody- or probe-linked reagents. Readouts from such assays may be the mean fluorescence associated with individual fluorescent antibody-detected cell surface molecules or cytokines, or the average fluorescence intensity, the median fluorescence intensity, the variance in fluorescence intensity, or some relationship among these.

Both single cell multiparameter and multicell multiparameter multiplex assays, where input cell types are identified and parameters are read by quantitative imaging and fluorescence and confocal microscopy are used in the art, see Confocal Microscopy Methods and Protocols (Methods in Molecular Biology Vol. 122.) Paddock, Ed., Humana Press, 1998. These methods are described in U.S. Pat. No. 5,989,833 issued Nov. 23, 1999.

Quantitative readouts of parameters may include baseline measurements in the absence of agents or a pre-defined genetic control condition and test measurements in the presence of a single or multiple agents or a genetic test condition. Furthermore, quantitative readouts of parameters may include long-term recordings and may therefore be used as a function of time (change of parameter value). Readouts may be acquired either spontaneously or in response to or presence of stimulation or perturbation of the multi-spheroid tissue. The quantitative readouts of parameters may further include a single determined value, the mean or median values of parallel, subsequent or replicate measurements, the variance of the measurements, various normalizations, the cross-correlation between parallel measurements, etc. and every statistic used to a calculate a meaningful and informative factor.

In some embodiments, the assays described herein are used to evaluate changes in function of a multi-spheroid tissue in response to optogenetic perturbation. In certain embodiments, optogenetics is used to induce cell-specific perturbations in the multi-spheroid tissue. For example, optogenetics can be used to excite or inhibit one or more selected neurons of interest using light. For a description of optogenetics techniques, see, e.g., Abe et al., 2012; Desai et al., 2011; Duffy et al., 2015; Gerits et al., 2012; Kahn et al., 2013; Lee et al., 2010; Liu et al., 2015; Ohayon et al., 2013; Weitz et al., 2015; Weitz and Lee, 2013; herein incorporated by reference.

The results of an assay can be entered into a data processor to provide a dataset. Algorithms are used for the comparison and analysis of data obtained under different conditions. The effect of factors and agents is read out by determining changes in multiple parameters. The data will include the results from assay combinations with the agent(s), and may also include one or more of the control state, the simulated state, and the results from other assay combinations using other agents or performed under other conditions. For rapid and easy comparisons, the results may be presented visually in a graph, and can include numbers, graphs, color representations, etc.

The dataset is prepared from values obtained by measuring parameters in the presence and absence of different cells, e.g., genetically modified cells, cells cultured in the presence of specific factors or agents that affect neuronal function, as well as comparing the presence of the agent of interest and at least one other state, usually the control state, which may include the state without the agent or with a different agent. The results may be normalized against a standard, usually a "control value or state," to provide a normalized data set. Values obtained from test conditions can be normalized by subtracting the unstimulated control values from the test values, and dividing the corrected test value by the corrected stimulated control value. Other methods of normalization can also be used; and the logarithm or other derivative of measured values or ratio of test to stimulated or other control values may be used. Data is normalized to control data on the same multi-spheroid tissue under control conditions, but a dataset may comprise normalized data from one, two or multiple multi-spheroid tissues and assay conditions.

The dataset can comprise values of the levels of sets of parameters obtained under different assay combinations. Compilations are developed that provide the values for a sufficient number of alternative assay combinations to allow comparison of values.

A database can be compiled from sets of experiments, for example, a database can contain data obtained from a panel of assay combinations, with multiple different environmental changes, where each change can be a series of related compounds, or compounds representing different classes of molecules.

Mathematical systems can be used to compare datasets, and to provide quantitative measures of similarities and differences between them. For example, the datasets can be analyzed by pattern recognition algorithms or clustering methods (e.g., hierarchical or k-means clustering, etc.) that use statistical analysis (correlation coefficients, etc.) to quantify relatedness. These methods can be modified (by weighting, employing classification strategies, etc.) to optimize the ability of a dataset to discriminate different functional effects. For example, individual parameters can be given more or less weight when analyzing the dataset, in order to enhance the discriminatory ability of the analysis. The effect of altering the weights assigned each parameter is assessed, and an iterative process is used to optimize pathway or cellular function discrimination.

The comparison of a dataset obtained from a test compound, and a reference dataset(s) is accomplished by the use of suitable deduction protocols, AI systems, statistical comparisons, etc. Preferably, the dataset is compared with a database of reference data. Similarity to reference data involving known pathway stimuli or inhibitors can provide an initial indication of the cellular pathways targeted or altered by the test stimulus or agent.

A reference database can be compiled. These databases may include reference data from panels that include known agents or combinations of agents that target specific pathways, as well as references from the analysis of cells treated under environmental conditions in which single or multiple environmental conditions or parameters are removed or specifically altered. Reference data may also be generated from panels containing cells with genetic constructs that selectively target or modulate specific cellular pathways. In this way, a database is developed that can reveal the contributions of individual pathways to a complex response.

The effectiveness of pattern search algorithms in classification can involve the optimization of the number of parameters and assay combinations. The disclosed techniques for selection of parameters provide for computational requirements resulting in physiologically relevant outputs. Moreover, these techniques for pre-filtering data sets (or potential data sets) using cell activity and disease-relevant biological information improve the likelihood that the outputs returned from database searches will be relevant to predicting agent mechanisms and in vivo agent effects.

For the development of an expert system for selection and classification of biologically active drug compounds or other interventions, the following procedures are employed. For every reference and test pattern, typically a data matrix is generated, where each point of the data matrix corresponds to a readout from a parameter, where data for each parameter may come from replicate determinations, e.g., multiple individual spheroids or multi-spheroid tissues of the same type. As previously described, a data point may be quantitative, semi-quantitative, or qualitative, depending on the nature of the parameter.

The readout may be a mean, average, median or the variance or other statistically or mathematically derived value associated with the measurement. The parameter readout information may be further refined by direct comparison with the corresponding reference readout. The absolute values obtained for each parameter under identical conditions will display a variability that is inherent in live biological systems and also reflects individual cellular variability as well as the variability inherent between individuals.

Classification rules are constructed from sets of training data (i.e., data matrices) obtained from multiple repeated experiments. Classification rules are selected as correctly identifying repeated reference patterns and successfully distinguishing distinct reference patterns. Classification rule-learning algorithms may include decision tree methods, statistical methods, naive Bayesian algorithms, and the like.

A knowledge database will be of sufficient complexity to permit novel test data to be effectively identified and classified. Several approaches for generating a sufficiently encompassing set of classification patterns, and sufficiently powerful mathematical/statistical methods for discriminating between them can accomplish this.

The data from spheroids treated with specific drugs known to interact with particular targets or pathways provide a more detailed set of classification readouts. Data generated from cells that are genetically modified using over-expression techniques and anti-sense techniques, permit testing the influence of individual genes on the phenotype.

A preferred knowledge database contains reference data for the spheroids/organoids, environments and parameters. For complex environments, data reflecting small variations in the environment may also be included in the knowledge database, e.g., environments where one or more factors or cell types of interest are excluded or included or quantitatively altered in, for example, concentration or time of exposure, etc.

Of particular interest for neuronal screening are parameters related to the electrical properties of the cells and therefore directly informative about neuronal function and activity in neural spheroids. Methods to measure neuronal activity may sense the occurrence of action potentials (spikes). The characteristics of the occurrence of a single spike or multiple spikes, either in timely clustered groups (bursts) or distributed over longer time (spike train), of a single neuron or a group of neurons indicate neuronal activation patterns and thus reflect functional neuronal properties, which can be described my multiple parameters. Such parameters can be used to quantify and describe changes in neuronal activity.

Neuronal activity parameters include, without limitation, total number of spikes (per recording period); mean firing rate (of spikes); inter-spike interval (distance between sequential spikes); total number of bursts (per recording period); burst frequency; number of spikes per burst; burst duration (in milliseconds); inter-burst interval (distance between sequential bursts); burst percentage (the portion of spikes occurring within a burst); total number of network bursts (spontaneous synchronized network activity); network burst frequency; number of spikes per network burst; network burst duration; inter-network-burst interval; inter-spike interval within network bursts; network burst percentage (the portion of bursts occurring within a network burst); salutatory migration, etc.

Quantitative readouts of neuronal activity parameters may include baseline measurements in the absence of agents or a pre-defined genetic control condition and test measurements in the presence of a single or multiple agents or a genetic test condition. Furthermore, quantitative readouts of neuronal activity parameters may include long-term recordings and may therefore be used as a function of time (change of parameter value). Readouts may be acquired either spontaneously or in response to or presence of stimulation or perturbation of the complete neuronal network or selected components of the network. The quantitative readouts of neuronal activity parameters may further include a single determined value, the mean or median values of parallel, subsequent or replicate measurements, the variance of the measurements, various normalizations, the cross-correlation between parallel measurements, etc. and every statistic used to a calculate a meaningful and informative factor.

Comprehensive measurements of neuronal activity using electrical or optical recordings of the parameters described herein may include spontaneous activity and activity in response to targeted electrical or optical stimulation of all neuronal cells or a subpopulation of neuronal cells within the organoid. Furthermore, spontaneous or induced neuronal activity can be measured in the self-assembled functional environment and circuitry of the neural culture or under conditions of selective perturbation or excitation of specific subpopulations of neuronal cells as discussed above.

In the provided assays, comprehensive measurements of neuronal activity can be conducted at different time points during neuronal maturation and usually include a baseline measurement directly before contacting the culture with the agents of interest and a subsequent measurement under agent exposure. Moreover, long-term effects of agents on neural maturation and development can be assessed by contacting an immature neural culture at an early time point with agents of interest and acquiring measurements of the same cultures after further maturation at a later time point compared to control cultures without prior agent exposure.

In some embodiments, standard recordings of neuronal activity of mature neural cultures are conducted after about 2 weeks, after about 3 weeks, after about 4 weeks, after about 6 weeks, after about 8 weeks following assembly of the organoid. Recordings of neuronal activity may encompass the measurement of additive, synergistic or opposing effects of agents that are successively applied to the cultures, therefore the duration recording periods can be adjusted according to the specific requirements of the assay. In some embodiments the measurement of neuronal activity is performed for a predetermined concentration of an agent of interest, whereas in other embodiments measurements of neuronal activity can be applied for a range of concentrations of an agent of interest.

In some embodiments, the assays described herein are used to evaluate changes in organoid function in response to optogenetic perturbation of neural activity. In certain embodiments, optogenetics is used to induce cell-specific perturbations in a multi-spheroid tissue or assembloid. For example, optogenetics can be used to excite or inhibit one or more selected neurons of interest using light. For a description of optogenetics techniques, see, e.g., Abe et al., 2012; Desai et al., 2011; Duffy et al., 2015; Gerits et al., 2012; Kahn et al., 2013; Lee et al., 2010; Liu et al., 2015; Ohayon et al., 2013; Weitz et al., 2015; Weitz and Lee, 2013; herein incorporated by reference.

In some embodiments the provided assays are used to assess maturation of the neural culture or single components including glutamatergic neurons, GABAergic interneurons, astrocytes, oligodendrocytes, microglia etc. Maturation of neuronal cells can be measured based on morphology by optically assessing parameters such as dendritic arborization, axon elongation, total area of neuronal cell bodies, number of primary processes per neuron, total length of processes per neuron, number of branching points per primary process as well as density and size of synaptic puncta stained by synaptic markers such as synapsin-1, synaptophysin, bassoon, PSD95, and Homer. Moreover, general neuronal maturation and differentiation can be assessed by measuring expression of marker proteins such as MAP2, TUJ-1, NeuN, Tau, PSA-NCAM, and SYN-1 alone or in combination using FACS analysis, immunoblotting, or fluorescence microscopy imaging, patch clamping. Maturation and differentiation of neuronal subtypes can further be tested by measuring expression of specific proteins. For excitatory neuronal cells this includes staining for e.g., VGLUT1/2, GRIA1/2/3/4, GRIN1, GRIN2A/B, GPHN etc. For inhibitory neuronal cells this includes staining for e.g., GABRA2, GABRB1, VGAT, and GAD67.

Patient-Derived Glioma Assembloid Produced by Magnetic Bioprinting

In some embodiments, a patient-derived glioma assembloid disease model is provided. Magnetic bioprinting as described herein can be used to control the spatial dynamics of glioma infiltration into a neural assembloid. In some embodiments, assembloids comprising hiPSC-derived regionalized neural organoids and patient-derived diffuse intrinsic pontine glioma (DIPG) organoids are provided. Magnetic bioprinting is used for localization and subsequent fusion of neural organoids with DIPG organoids. In one embodiment, an assembloid comprising a pontine DIPG organoid, a dorsal forebrain neural organoid, and a frontal lobe DIPG organoid, produced by the methods of magnetic bioprinting, described herein, is provided. In another embodiment, an assembloid comprising dorsal or ventral forebrain organoids and a frontal lobe DIPG organoid, produced by the methods of magnetic bioprinting, described herein, is provided. Such assembloid disease models can be used for modeling tumor infiltration and screening for therapeutics to treat DIPG.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-84 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A bioprinter for producing a multi-spheroid tissue, the bioprinter comprising:
   a plurality of microwells, wherein the microwells can be used for generating and culturing a plurality of spheroids;
   a reservoir comprising a support scaffold;
   a dual printhead comprising a first nozzle and a second nozzle, wherein the first nozzle comprises an extrusion channel, and the second nozzle is coupled to an electromagnet, wherein the electromagnet is connected to a rod that becomes magnetized when the electromagnet is turned on and demagnetized when the electromagnet is turned off;
   a container containing magnetic ink comprising magnetic particles, wherein the container is connected to the extrusion channel to allow the first nozzle to deposit the magnetic ink;
   a processor, wherein the processor is programmed to perform steps comprising:
   (i) locating a microwell that contains a selected spheroid;
   (ii) moving the dual printhead to a position over the microwell that contains the selected spheroid;

(iii) instructing the first nozzle to deposit the magnetic ink in the microwell containing the selected spheroid, wherein the selected spheroid is coated with the magnetic ink;

(iv) turning on the electromagnet, wherein the rod becomes magnetized;

(v) lowering the magnetized rod over the selected spheroid until the magnetized rod magnetically attaches to the magnetic particles of the magnetic ink coating the selected spheroid;

(vi) raising the magnetized rod, wherein the selected spheroid is lifted out of the microwell;

(vii) moving the magnetized rod carrying the selected spheroid to a selected position in the reservoir;

(viii) lowering the magnetized rod over a selected location in the support scaffold;

(ix) turning off the electromagnet to demagnetize the rod, wherein the selected spheroid detaches from the demagnetized rod and is deposited at the selected location in the support scaffold; and (x) repeating (i)-(ix), wherein additional selected spheroids are coated with the magnetic ink, lifted from the plurality of microwells with the magnetized rod, moved to the reservoir, and detached from the demagnetized rod and deposited at selected locations in the support scaffold to provide spatial control of the fusion of the plurality of spheroids to produce the multi-spheroid tissue.

2. The bioprinter of aspect 1, wherein the rod comprises a ferromagnetic metal.

3. The bioprinter of aspect 2, wherein the ferromagnetic metal is iron.

4. The bioprinter of aspect 1, wherein the rod has a diameter ranging from 1 mm to 5 mm.

5. The bioprinter of aspect 4, wherein the rod has a diameter of about 2 mm.

6. The bioprinter of aspect 1, wherein the magnetic ink comprises iron oxide magnetic particles.

7. The bioprinter of aspect 1, wherein the magnetic ink comprises magnetic particles embedded in a cytocompatible hydrogel.

8. The bioprinter of aspect 7, wherein the hydrogel of the magnetic ink comprises a cellulose nanofiber (CNF).

9. The bioprinter of aspect 8, wherein the hydrogel of the magnetic ink comprises 0.025 percent by weight (wt %) to 0.10 wt % CNF.

10. The bioprinter of aspect 9, wherein the hydrogel of the magnetic ink comprises about 0.025 wt % CNF.

11. The bioprinter of aspect 1, wherein the magnetic particles are magnetic nanoparticles.

12. The bioprinter of aspect 1, wherein the magnetic ink comprises 0.5 wt % to 3 wt % magnetic nanoparticles.

13. The bioprinter of aspect 12, wherein the magnetic ink comprises at least 1 wt % magnetic nanoparticles.

14. The bioprinter of aspect 1, wherein the support scaffold comprises a cytocompatible hydrogel.

15. The bioprinter of aspect 14, wherein the hydrogel of the support scaffold comprises 0.4 wt % to 0.6 wt % CNF.

16. The bioprinter of aspect 15, wherein the hydrogel of the support scaffold comprises about 0.5 wt % CNF.

17. The bioprinter of aspect 1, wherein the processor is further programmed to instruct the bioprinter to add cellulase to the support scaffold after step (x), wherein the support scaffold is removed from the multi-spheroid tissue.

18. The bioprinter of aspect 1, wherein voltage of the electromagnet and distance of the magnetic rod from the selected spheroid can be adjusted to control magnetic field strength surrounding the selected spheroid.

19. The bioprinter of aspect 1, further comprising a pump.

20. The bioprinter of aspect 19, wherein the pump is a syringe pump, a diaphragm pump, a peristaltic pump, or a piston pump.

21. The bioprinter of aspect 19, further comprising a multiway selector valve interfaced with the pump.

22. The bioprinter of aspect 21, further comprising a media ramp comprising one or more containers or wells comprising one or more types of media, wherein the one or more containers or wells are fluidically connected to the multiway selector valve such that a user can select a medium from the one or more types of media for distribution to one or more selected microwells.

23. The bioprinter of aspect 22, further comprising a container or well comprising cellulase, wherein the container or well comprising cellulase is fluidically connected to the multiway selector valve such that a user can add cellulase to one or more selected microwells.

24. The bioprinter of aspect 1, further comprising a chip, wherein the plurality of microwells and the reservoir comprising the support scaffold are contained on the chip.

25. The bioprinter of aspect 24, wherein the chip further comprises a raised connector channel between the microwells and the reservoir comprising the support scaffold.

26. The bioprinter of aspect 24 wherein the chip comprises polydimethylsiloxane (PDMS).

27. The bioprinter of aspect 24, wherein the plurality of microwells is arranged linearly in rows, where each row of microwells is fluidically connected to an inlet.

28. The bioprinter of aspect 24, wherein for each row of microwells, the inlet further comprises a syringe alignment pad, wherein the syringe alignment pad is aligned with one end of the row of microwells.

29. The bioprinter of aspect 24, wherein for each row of microwells, the chip further comprises an offset platform for medium addition to the microwells, wherein the offset platform for medium addition to the microwells is located between the syringe alignment pad and the row of microwells.

30. The bioprinter of aspect 1, further comprising a temperature controller that maintains the microwells and the reservoir at a suitable temperature for culturing the plurality of spheroids and the multi-spheroid tissue.

31. The bioprinter of aspect 1, further comprising a power source, wherein the power source controls a voltage applied to the electromagnet and the strength of the magnetic force used to lift the spheroids.

32. The bioprinter of aspect 1, further comprising an inlet fluidically connected to the reservoir comprising the support scaffold.

33. The bioprinter of aspect 1, wherein the plurality of spheroids is a plurality of organoids.

34. The bioprinter of aspect 1, wherein the multi-spheroid tissue is an assembloid.

35. The bioprinter of aspect 1, wherein the bioprinter comprises multiple dual printheads.

36. A method of using the bioprinter of aspect 1 to produce a multi-spheroid tissue, the method comprising:

(a) adding cells to the plurality of microwells, (b) adding spheroid-specific media to the plurality of microwells;

(c) culturing the cells under suitable conditions, wherein the plurality of spheroids is generated from the cells;

(d) instructing the processor to perform the steps comprising:

(i) locating a microwell that contains a selected spheroid;

(ii) moving the dual printhead to a position over the microwell that contains the selected spheroid;

(iii) instructing the first nozzle to deposit the magnetic ink in the microwell containing the selected spheroid, wherein the selected spheroid is coated with the magnetic ink;

(iv) turning on the electromagnet, wherein the rod becomes magnetized;

(v) lowering the magnetized rod over the selected spheroid until the magnetized rod magnetically attaches to the magnetic particles of the magnetic ink coating the selected spheroid;

(vi) raising the magnetized rod, wherein the selected spheroid is lifted out of the microwell;

(vii) moving the magnetized rod carrying the selected spheroid to a selected position in the reservoir;

(viii) lowering the magnetized rod over a selected location in the support scaffold;

(ix) turning off the electromagnet to demagnetize the rod, wherein the selected spheroid detaches from the demagnetized rod and is deposited at the selected location in the support scaffold; and (x) repeating (i)-(ix), wherein additional selected spheroids are coated with the magnetic ink, lifted from the plurality of microwells with the magnetized rod, moved to the reservoir, and detached from the demagnetized rod and deposited at selected locations in the support scaffold; and (e) culturing the plurality of spheroids within the support scaffold under conditions suitable for growth of the spheroids, wherein fusion of the plurality of spheroids results in generation of the multi-spheroid tissue.

37. The method of aspect 36, further comprising removing the support scaffold from the multi-spheroid tissue by treating the CNF hydrogel with a cellulase to degrade the CNF hydrogel while leaving the multi-spheroid tissue intact.

38. The method of aspect 36, further comprising adjusting voltage of the electromagnet and distance of the magnetic rod from the selected spheroid to control magnetic field strength surrounding the selected spheroid.

39. The method of aspect 38, wherein the voltage of the electromagnet is about 15 volts.

40. The method of aspect 36, further comprising culturing the multi-spheroid tissue in a suspension culture.

41. The method of aspect 36, further comprising culturing the multi-spheroid tissue until the multi-spheroid tissue is mature.

42. The method of aspect 36, wherein the coated spheroids are lifted and positioned in the support scaffold sequentially.

43. The method of aspect 36, wherein the bioprinter comprises multiple dual printheads, and wherein multiple coated spheroids are lifted and positioned in the support scaffold simultaneously.

44. The method of aspect 36, wherein the plurality of spheroids is derived from induced pluripotent stem cells (IPSCs) or somatic cells.

45. The method of aspect 36, wherein the plurality of spheroids is derived from human or non-human IPSCs or somatic cells.

46. The method of aspect 36, wherein the plurality of spheroids is derived from cells obtained from a human or non-human donor.

47 The method of aspect 46, wherein the donor-derived cells are tumor cells or diseased cells.

48. The method of aspect 36, wherein the plurality of spheroids comprises IPSC-derived neurons, IPSC-derived glia, or IPSC-derived muscle cells, or any combination thereof.

49. The method of aspect 48, wherein the IPSC-derived neurons are interneurons, motor neurons, sensory neurons, afferent neurons, efferent neurons, inhibitory neurons, or excitatory neurons, or any combination thereof.

50. The method of aspect 48, wherein the IPSC-derived neurons are glutamatergic neurons, cholinergic neurons, GABAergic neurons, dopaminergic neurons, serotonergic neurons, or histaminergic neurons, or any combination thereof.

51. The method of aspect 48, wherein the IPSC-derived glia are astrocytes, oligodendrocytes, ependymal cells, microglia, NG2 glia, or any combination thereof.

52. The method of aspect 48, wherein the IPSC-derived muscle cells are skeletal muscle cells, smooth muscle cells, or cardiac muscle cells.

53. The method of aspect 44, wherein the cells comprise at least one genetic mutation associated with a developmental or degenerative disorder.

54. The method of aspect 44, further comprising genetically modifying the cells to introduce at least one genetic mutation associated with a developmental or degenerative disorder into their genome.

55. The method of aspect 36, wherein the plurality of spheroids comprises IPSC-derived gastric cells or IPSC-derived intestinal cells, or any combination thereof.

56. The method of aspect 55, wherein the IPSC-derived gastric cells or the IPSC-derived intestinal, or any combination thereof comprise at least one genetic mutation associated with a gastrointestinal tract disorder.

57. The method of aspect 55, further comprising genetically modifying the IPSCs or the IPSC-derived gastric cells or the IPSC-derived intestinal, or any combination thereof to introduce at least one genetic mutation associated with a gastrointestinal tract disorder.

58. The method of aspect 44, wherein the plurality of spheroids comprises IPSC-derived cells of any lineage.

59. The method of 36, further comprising: collecting somatic cells from a patient having at least one genetic mutation associated with a developmental or degenerative disorder; generating the IPSCs from the somatic cells; and generating the plurality of spheroids from the IPSCs.

60. The method of aspect 36, wherein the plurality of spheroids mimics one or more brain regions of interest.

61. The method of aspect 60, wherein the one or more brain regions of interest are selected from the basal ganglia, striatum, medulla, pons, forebrain, midbrain, hindbrain, medulla oblongata, hypothalamus, thalamus, epithalamus, amygdala, superior colliculus, cerebral cortex, neocortex, allocortex, hippocampus, claustrum, olfactory bulb, frontal lobe, temporal lobe, parietal lobe, occipital lobe, caudate-putamen, external globus pallidus, internal globus pallidus, subthalamic nucleus, substantia nigra, thalamus, and motor cortex regions of the brain.

62. A multi-spheroid tissue produced by the method of aspect 36.

63. A method of screening a candidate agent, the method comprising: contacting the multi-spheroid tissue of aspect 62 with the candidate agent, and determining the effects of the agent on morphologic, genetic, or functional parameters.

64. The method of aspect 63, wherein determining the effect of the agent comprises performing immunohistochemistry, gene expression profiling, confocal microscopy, atomic force microscopy, super-resolution microscopy, light-sheet microscopy, two-photon microscopy, fluorescence microscopy, calcium imaging, electrophysiology measurements, patch clamping, migration assays, axonal growth and pathfinding assays, or phagocytosis assays.

65. The method of aspect 62, wherein the multi-spheroid tissue comprises IPSC-derived cells, somatic cells, or donor derived cells, or any combination thereof.

66. The method of aspect 65, wherein the multi-spheroid tissue comprises IPSC-derived neurons, IPSC-derived glia, or IPSC-derived muscle cells, or any combination thereof.

67. The method of aspect 66, further comprising using optogenetics to excite or inhibit one or more selected IPSC-derived neurons of interest using light.

68. The method of aspect 62, wherein the multi-spheroid tissue comprises a retinal spheroid, a thalamic spheroid, and a forebrain spheroid.

69. The method of aspect 68, wherein the thalamic spheroid is fused to the retinal spheroid and the forebrain spheroid.

70. The method of aspect 62, wherein the multi-spheroid tissue comprises a gastric spheroid and an intestinal spheroid.

71. The method of aspect 70, wherein the gastric spheroid is fused to the intestinal spheroid.

72. The method of aspect 62, wherein the multi-spheroid tissue comprises neural organoids, mesenchymal stromal cell (MSC) spheroids, or human umbilical vein endothelial cell (HUVEC) spheroids.

73. The method of aspect 62, wherein the multi-spheroid tissue comprises a dorsal forebrain neural organoid, a ventral forebrain neural organoid, or a combination thereof.

74. The method of aspect 73, wherein the multi-spheroid tissue further comprises a frontal lobe diffuse intrinsic pontine glioma (DIPG) organoid, a pons DIPG organoid, or a combination thereof.

75. A computer implemented method for controlling a bioprinter for producing a multi-spheroid tissue, the computer performing steps comprising:

(a) locating a microwell that contains a selected spheroid;

(b) moving the dual printhead to a position over the microwell that contains the selected spheroid;

(c) instructing the first nozzle to deposit the magnetic ink in the microwell containing the selected spheroid, wherein the selected spheroid is coated with the magnetic ink;

(d) turning on the electromagnet, wherein the rod becomes magnetized;

(e) lowering the magnetized rod over the selected spheroid until the magnetized rod magnetically attaches to the magnetic particles of the magnetic ink coating the selected spheroid;

(f) raising the magnetized rod, wherein the selected spheroid is lifted out of the microwell;

(g) moving the magnetized rod carrying the selected spheroid to a selected position in the reservoir;

(h) lowering the magnetized rod over a selected location in the support scaffold;

(i) turning off the electromagnet to demagnetize the rod, wherein the selected spheroid detaches from the demagnetized rod and is deposited at the selected location in the support scaffold; and (j) repeating (a)-(i), wherein additional selected spheroids are coated with the magnetic ink, lifted from the plurality of microwells with the magnetized rod, moved to the reservoir, and detached from the demagnetized rod and deposited at selected locations in the support scaffold to provide spatial control of the fusion of the plurality of spheroids to produce the multi-spheroid tissue.

76. The computer implemented method of aspect 75, further comprising instructing the bioprinter to add cellulase to the support scaffold after step (j), wherein the support scaffold is removed from the multi-spheroid tissue.

77. A non-transitory computer-readable medium comprising program instructions that, when executed by a processor in a computer, causes the processor to perform the method of aspect 76.

78. A kit comprising the non-transitory computer-readable medium of aspect 77 and instructions for producing a multi-spheroid tissue.

79. The kit of aspect 78, further comprising a bioprinter for producing a multi-spheroid tissue, the bioprinter comprising:

a plurality of microwells, wherein the microwells can be used for generating and culturing a plurality of spheroids;

a reservoir comprising a support scaffold;

a dual printhead comprising a first nozzle and a second nozzle, wherein the first nozzle comprises an extrusion channel, and the second nozzle is coupled to an electromagnet, wherein the electromagnet is connected to a rod that becomes magnetized when the electromagnet is turned on and demagnetized when the electromagnet is turned off; and a container containing magnetic ink comprising magnetic particles, wherein the container is connected to the extrusion channel to allow the first nozzle to deposit the magnetic ink.

80. A method of producing a multi-spheroid tissue, the method comprising:

(a) providing a plurality of spheroids;

(b) coating a selected spheroid of the plurality with magnetic particles;

(c) turning on an electromagnet, wherein the electromagnet is connected to a rod that becomes magnetized when the electromagnet is turned on;

(d) lowering the magnetized rod over the selected spheroid until the magnetized rod magnetically attaches to the magnetic particles coating the selected spheroid;

(e) raising the magnetized rod, wherein the selected spheroid is lifted by the magnetized rod;

(f) moving the magnetized rod carrying the selected spheroid to a position over a support scaffold;

(g) lowering the magnetized rod over a selected location in the support scaffold;

(h) turning off the electromagnet to demagnetize the rod, wherein the selected spheroid detaches from the demagnetized rod and is deposited at the selected location in the support scaffold; and (i) repeating (a)-(h), wherein additional spheroids of the plurality are coated with magnetic particles, moved with the magnetized rod, and deposited at selected locations in the support scaffold; and (j) culturing the plurality of spheroids within the support scaffold under conditions suitable for growth of the spheroids, wherein fusion of the plurality of spheroids results in generation of the multi-spheroid tissue.

81. The method of aspect 80, wherein the plurality of spheroids are provided in a culture medium comprising the magnetic particles, wherein said raising the magnetized rod lifts the selected spheroid out of the culture medium.

82. The method of aspect 80, wherein the hydrogel comprises a cellulose nanofiber (CNF).

83. The method of aspect 82, wherein the hydrogel comprises 0.025 percent by weight (wt %) to 0.10 wt % CNF.

84. The method of aspect 83, wherein the hydrogel comprises about 0.025 wt % CNF.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

Example 1

Spatially Controlled Fabrication of Multi-Spheroid Tissues using Magnetic Bioprinting

INTRODUCTION

To facilitate the construction of neural assembloids in 3D with fine spatial control over OBB fusion, we developed a novel approach we term Spheroid Transfer Assisted by Magnetic Printing (STAMP). STAMP employs a magnetic nanoparticle (MNP)-laden cellulose nanofiber (CNF) hydrogel, a CNF support scaffold enclosed within a custom-designed printed reservoir, and a magnetized 3D printer to control the spatial arrangement of the OBBs. Once fused, the resultant assembloid can be released from the support with bioorthogonal, on-demand degradation of the CNF scaffold. The spatially patterned assembloid can then be matured over time to facilitate investigations into neurodevelopmental phenomena or subjected to promising therapeutic compounds for target validation.

2. Results

2.1 Physical Characterization of hiPSC-Derived Neural Organoids

Figure 1B:
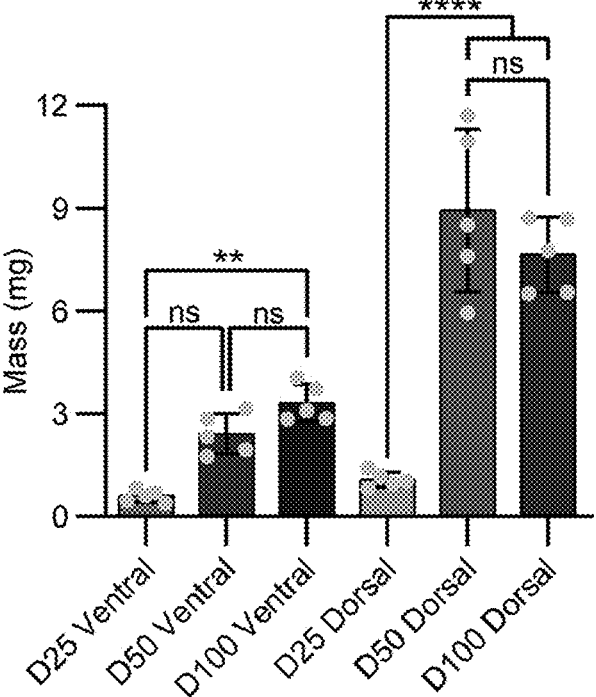
Figure 1C:
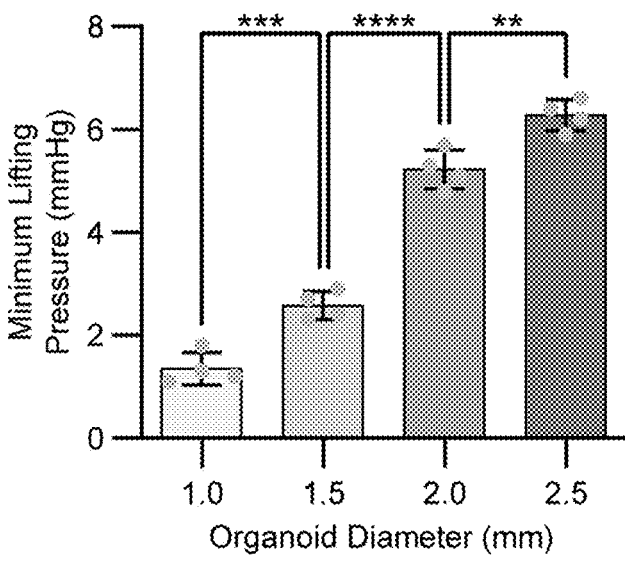

Previous demonstrations of aspiration-assisted bioprinting (AAB) reported a linear relationship between the diameter of OBBs and their required lifting pressure[13]. To date, most demonstrations of AAB include mesenchymal stromal cell (MSC) spheroids as the OBBs[13-16] (Table 1). As such, we began our characterization of the physical properties of OBBs by comparing human forebrain neural organoids to MSC spheroids. We utilized established differentiation methods to generate regionalized human induced pluripotent stem cell (hiPSC)-derived dorsal (cortical) and ventral (subpallium) forebrain organoids[2]. Compared to MSC spheroids (270.5±15.2 μm, mean±SD) and human umbilical vein endothelial cell (HUVEC) spheroids (240.8±21.8 μm), hiPSC-derived forebrain neural organoids are significantly larger in diameter at day 25 (ventral: 1143±121.2, dorsal: 1551±179.9 μm, p<0.0001). While MSC and HUVEC spheroids showed negligible change in diameter over time, neural organoids continued to increase in size both at day 50 (ventral: 1492±161.4 μm, dorsal: 2635±216.1 μm) and day 100 (ventral: 1770±226.7 μm, dorsal: 2830±182.2 μm) (FIG. 1A). As the diameter of these neural organoids increased, so too did their mass (FIG. 1B). Consistent with previous reports[13], these increases in size led to concomitant increases in the minimum pressure required to lift the submerged tissue using AAB from 1.4±0.3 mmHg to 6.3±0.3 mmHg (FIG. 1C).

Figure 1D:
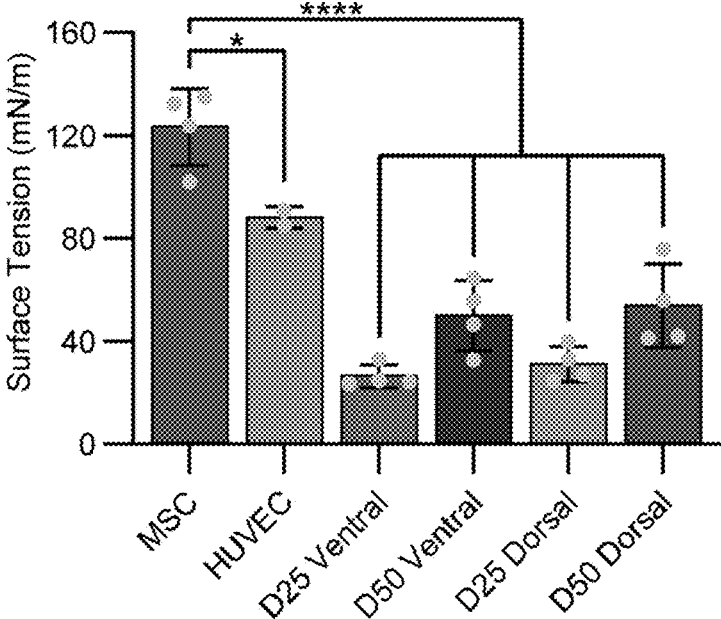
Figure 1E:
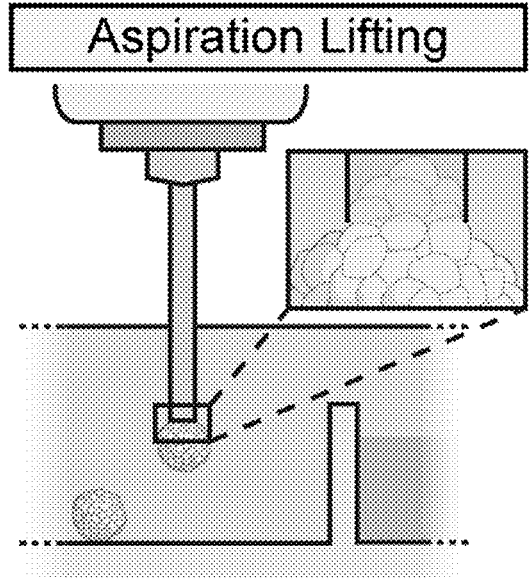
Figure 5A:
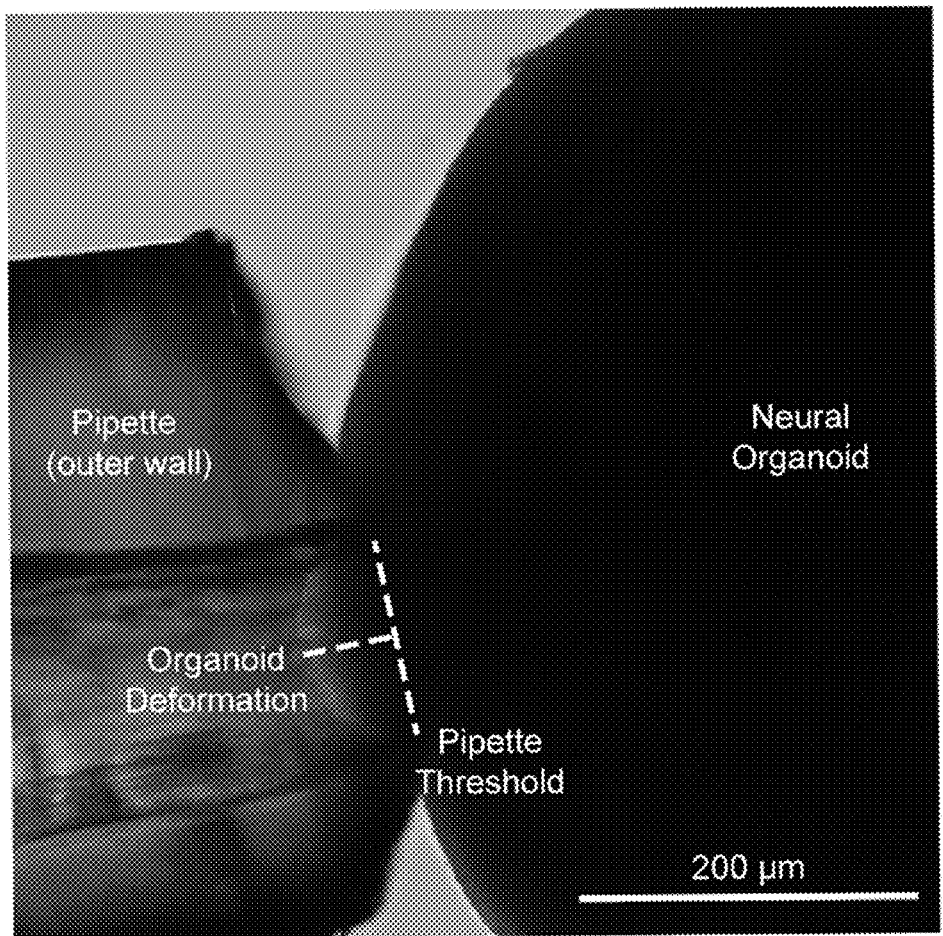
FIGS. 5A-5B. Neural organoid surface tension measurements.
Figure 5B:
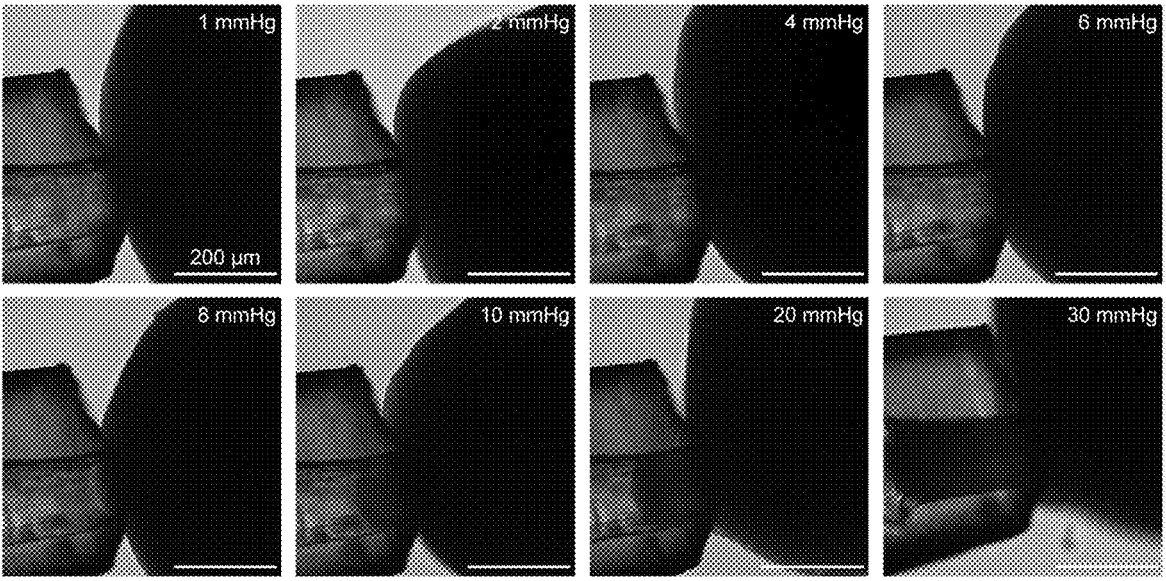

The structural integrity of OBBs lifted with AAB is dependent upon the degree to which the tissue is resistant to deformation by aspiration force. This resistance can be quantified as the surface tension of an OBB, as measured with micropipette aspiration[13] (FIGS. 5A, 5B). Although neural organoids require higher lifting pressures than MSC spheroids, they have significantly lower surface tension (p<0.0001) (FIG. 1D). Taken together, these observations imply that neural organoids may experience marked structural deformation when manipulated by the AAB procedure (FIG. 1E).

2.2 Neural Organoid Deformation Following AAB and STAMP

Figure 1F:
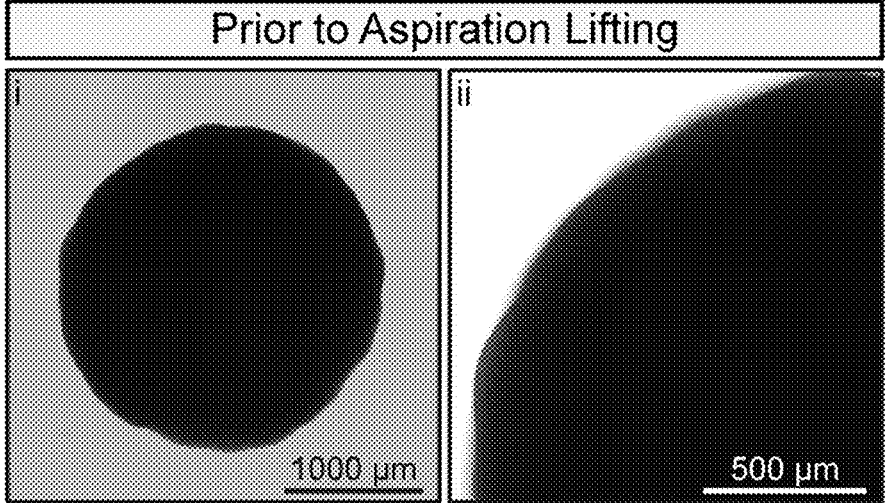
Figure 1G:
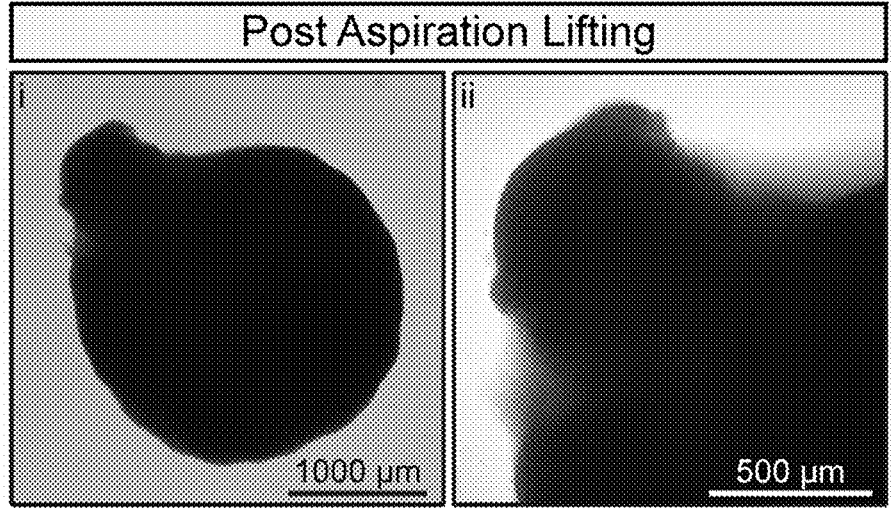
Figure 1H:
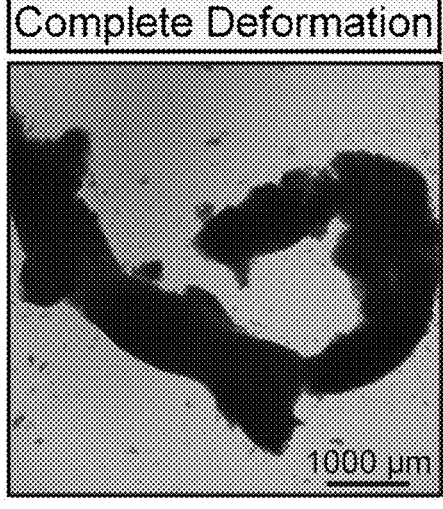
Figure 1I:
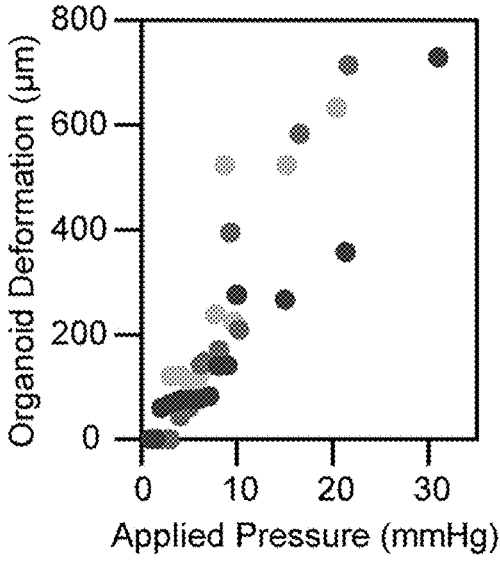
Figure 1J:
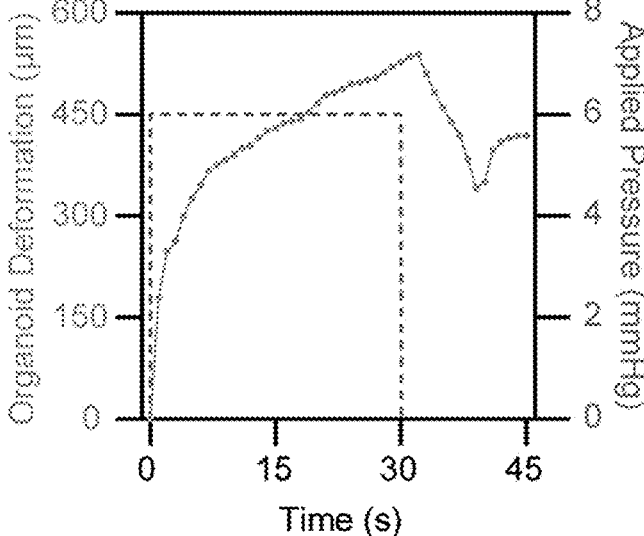
Figure 1K:
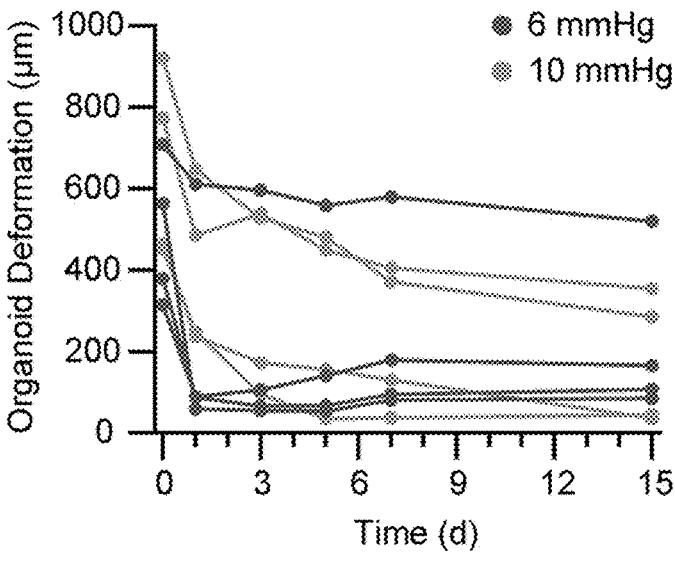
Figure 6:
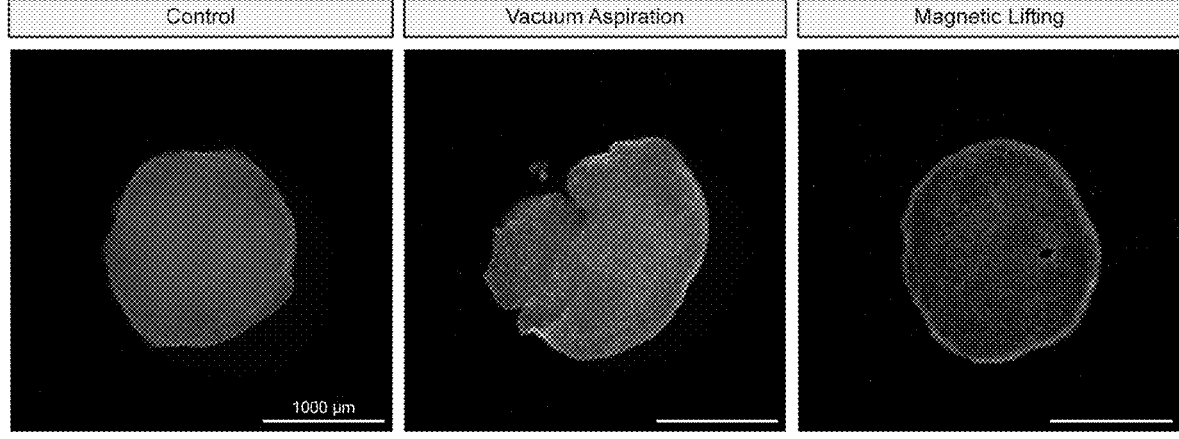
FIG. 6. Neural organoid viability following vacuum aspiration and magnetic lifting. Representative fluorescence images of neural organoids with and without aspiration-assisted lifting and magnetic lifting with calcein-AM labeled live cells (green) and ethidium homodimer-1 labeled dead cells (red). The control organoid was not lifted. The dark dots visible on the neural organoid exposed to magnetic lifting are MNPs on the organoid surface.
Figure 7A:
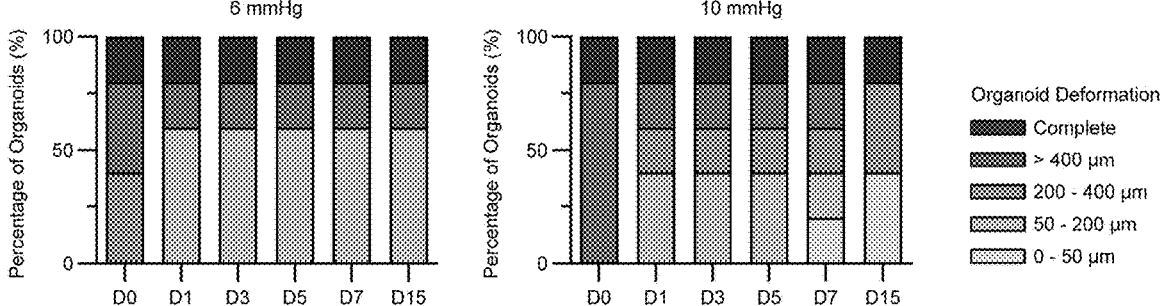
FIGS. 7A-7C. Aspiration-mediated deformation over time.
Figure 7B:
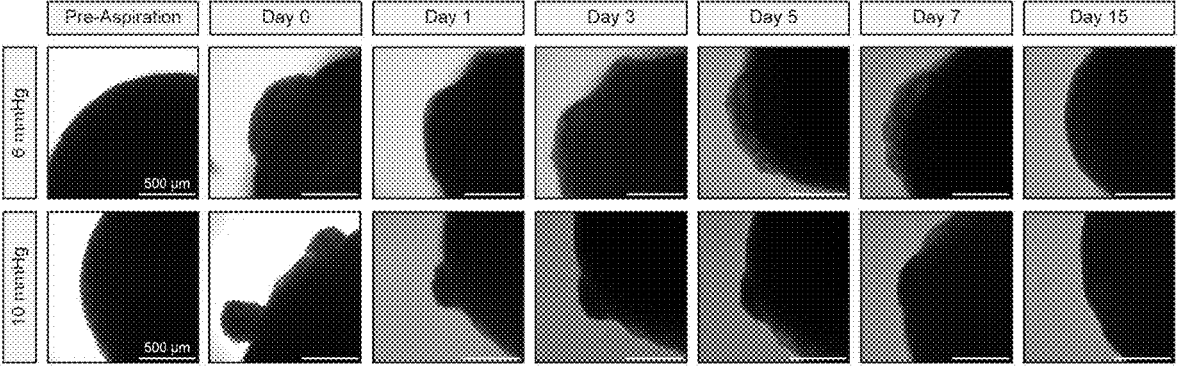
Figure 7C:
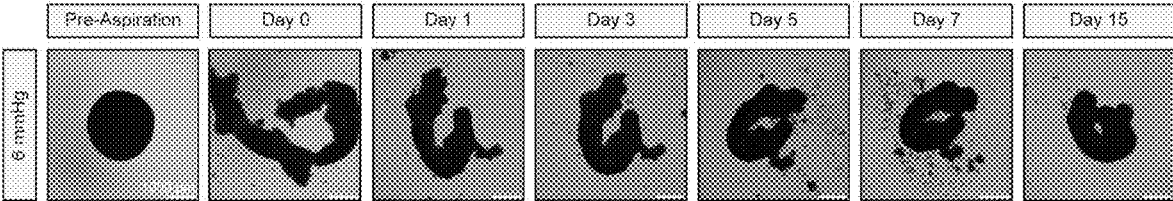

To evaluate potential deformation during aspiration, we exposed neural organoids to their minimum lifting pressure. Following aspiration, the surface of the neural organoids exhibited substantial local distension (FIGS. 1F, 1G, 1H). This deformation increased as a function of the applied pressure across multiple replicates (FIG. 11). Once the aspiration force was released, neural organoids continued to briefly distend before retracting; interestingly, even at the minimum lifting pressure, this retraction was incomplete, and irreversible plastic deformation was observed (FIG. 1J). While neural organoid viability does not seem to vary (FIG. 6), these plastic deformations were substantial at both 6 mmHg (491.9±178.4 µm) and 10 mmHg (652.2±232.3 µm) (FIG. 1K). After 15 days, 75% of organoids still exhibited protrusions greater than 50 µm (FIGS. 7A, 7B). Moreover, 20% of organoids underwent severe distension that distorted their spherical shape following release of the aspiration force (FIGS. 7A, 7C). Given the imperative of a conserved cytoarchitecture within the neural organoid[17,18], this degree of distension would be prohibitive to studies of neural development or disease.

Figure 1L:
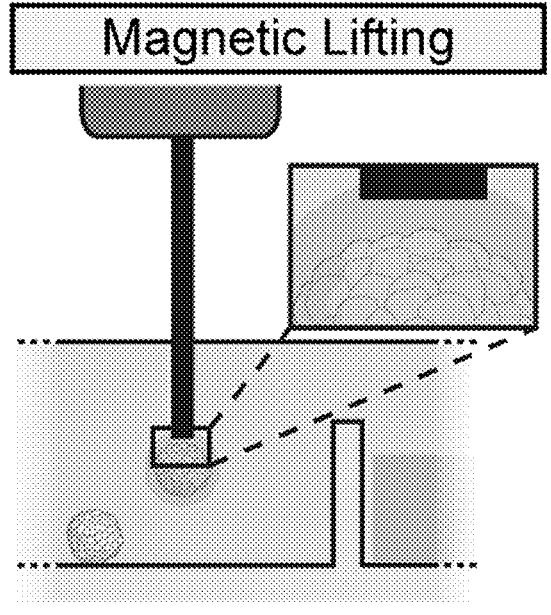
Figure 1M:
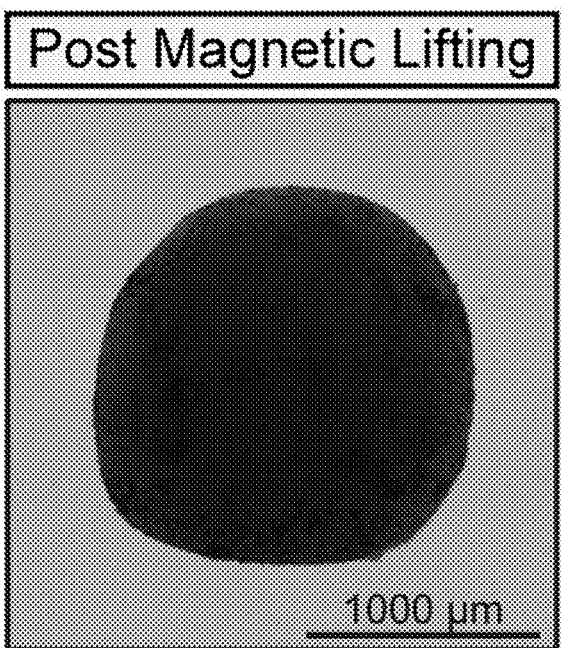

The STAMP platform relies upon the magnetic actuation of MNPs, which are embedded within a CNF ink biomaterial that encases the OBB. An iron rod affixed to an electromagnet mounted on a modified 3D printer is used to control the lifting, positioning, and deposition of the MNP-coated OBB. As such, with STAMP, the OBB is lifted in response to a force that is distributed across the entire OBB surface, unlike aspiration, which concentrates force and results in deformation during the lifting process (FIGS. 1E, 1L). As a result, structural deformation with STAMP is not observed (FIG. 1M).

Figure 2B:
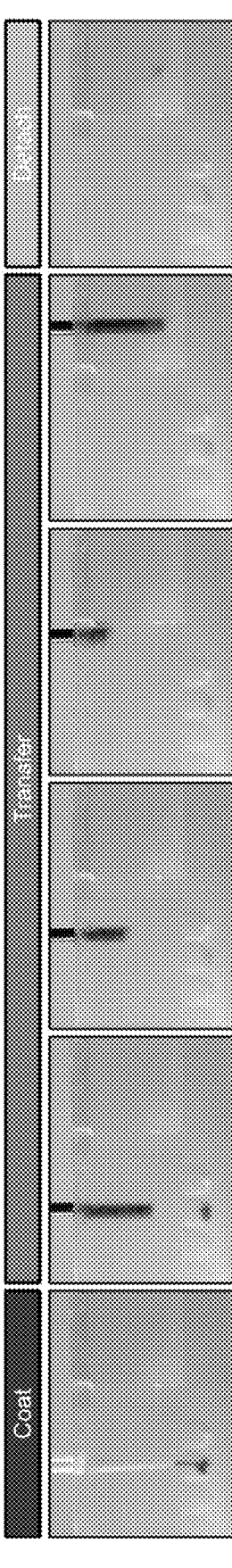

2.3 STAMP Facilitates the Controlled Lifting, Transfer, and Deposition of Neural Organoids in 3D The STAMP platform consists of the following series of repeatable, automatable steps: (i) coat organoids with the iron-oxide MNP embedded CNF ink, (ii) lift the coated organoid with an iron rod attached to an electromagnet-modified 3D printer, (iii) position the lifted organoid in 3D within a CNF support scaffold, and (iv) turn off the electromagnet and remove the iron rod (FIGS. 2A, 2B).

Figure 8A:
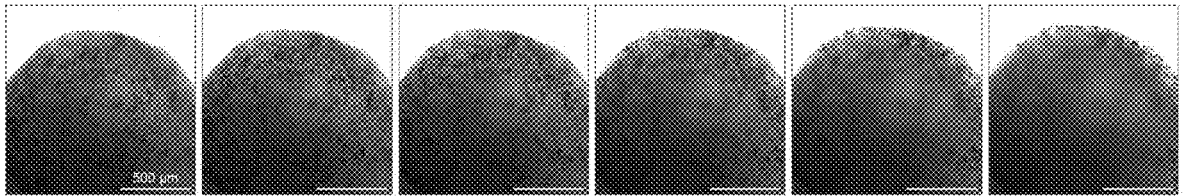
FIGS. 8A-8B. CNF MNPs coat neural organoids sufficiently for lifting.
Figure 8B:
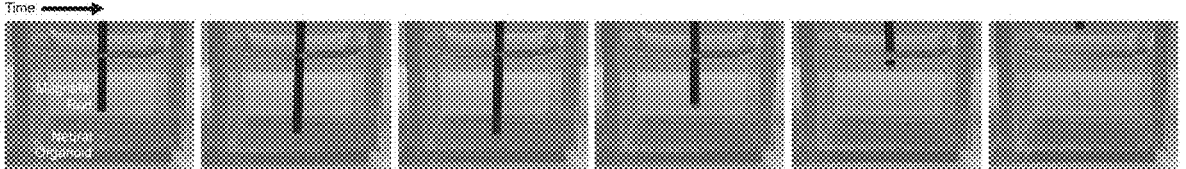
Figure 9A:
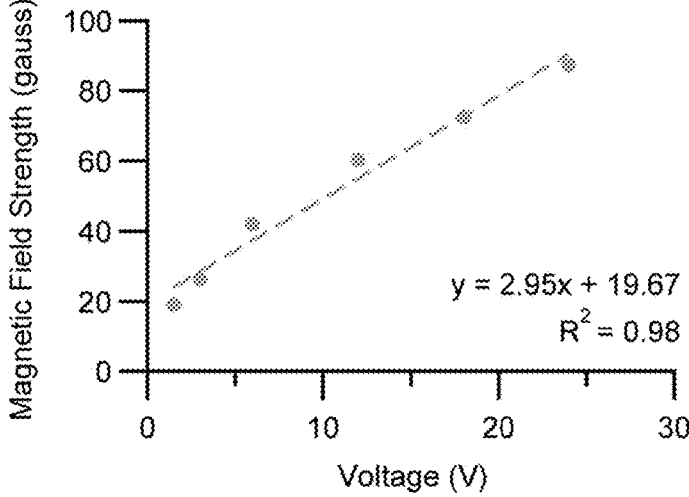
FIGS. 9A-9B. Quantification of magnetic field strength.
Figure 9B:
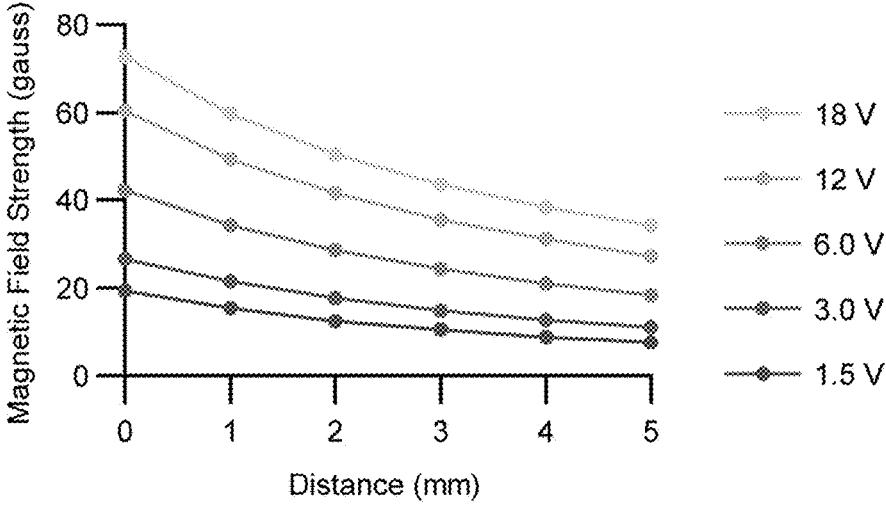
Figure 10A:
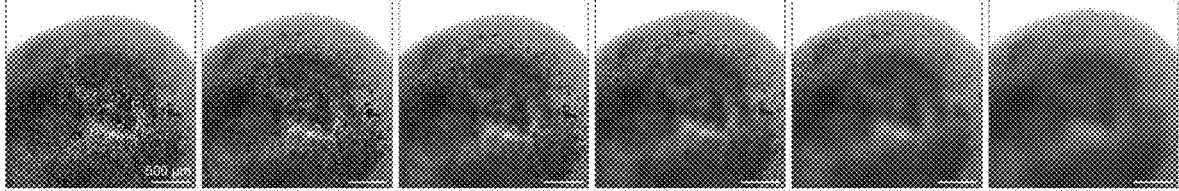
FIGS. 10A-10B. Orbital shakers coat neural organoids sufficiently for lifting.
Figure 10B:
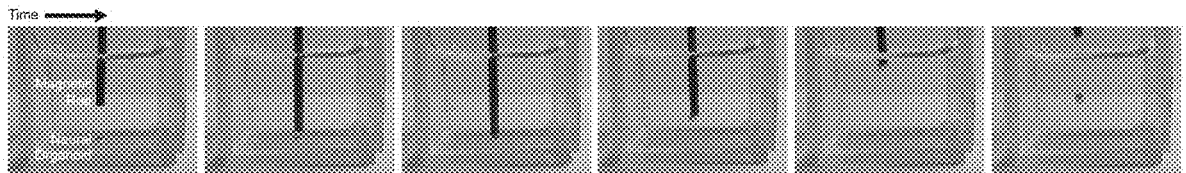

The organoid coating process is achieved by first mixing MNPs into a CNF hydrogel and then dispensing volumes of the mixture atop each individual OBB. Both commercially available MNPs and iron-oxide nanoparticles synthesized in-house through co-precipitation in a basic solution (Table 2) were successfully utilized for OBB coating. After 30 minutes of coating, the MNPs are evenly distributed across the surface of the organoid (FIG. 8A). To lift the coated organoid, a conventional 3D printer is modified such that an affixed electromagnet can be switched on and off with the same G-code that is used to direct the movement of the print head. An iron rod (with a diameter of 2 mm) is then bound to the electromagnet. Once the rod is bound, it is positioned above, and subsequently lowered toward, the coated organoid. As a function of the magnetic field strength, which is tuned by modulating the voltage of the electromagnet and the distance of the magnetic rod (FIG. 9), the MNPs within the CNF ink are pulled towards the rod, resulting in lifting of the OBB (FIG. 8B). As an alternative OBB coating approach that would be amenable to cultures grown within bioreactors, MNPs can be added directly to the medium of a suspension culture and agitated with an orbital shaker (FIG. 10). Once the organoid is affixed to the end of the magnetized rod, it can be transported from the liquid medium into the CNF support scaffold. Importantly, the final position of the organoid can be addressed in X, Y, and Z dimensions. Once the desired position is achieved, the electromagnet is turned off, and the iron rod is removed.

2.4 Characterization of the CNF Ink and Embedded MNPs

Figure 2C:
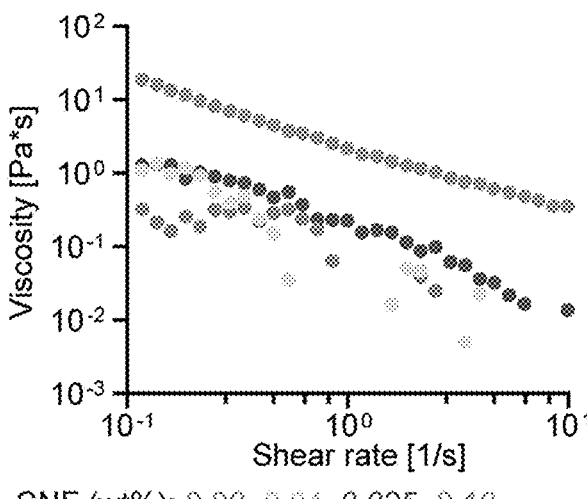
Figure 2D:
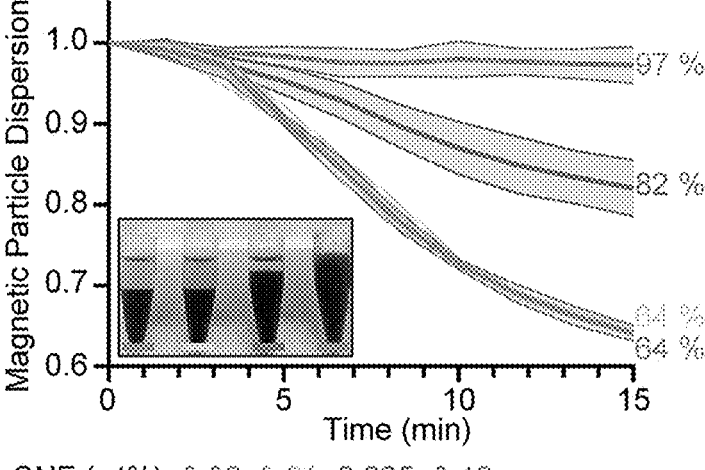
Figure 2E:
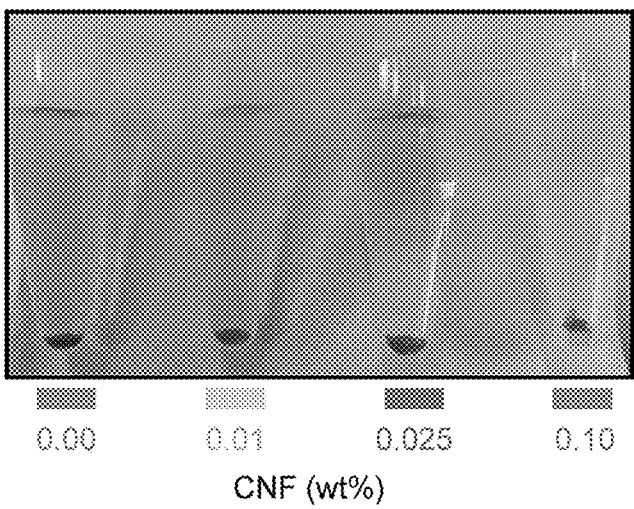
Figure 11A:
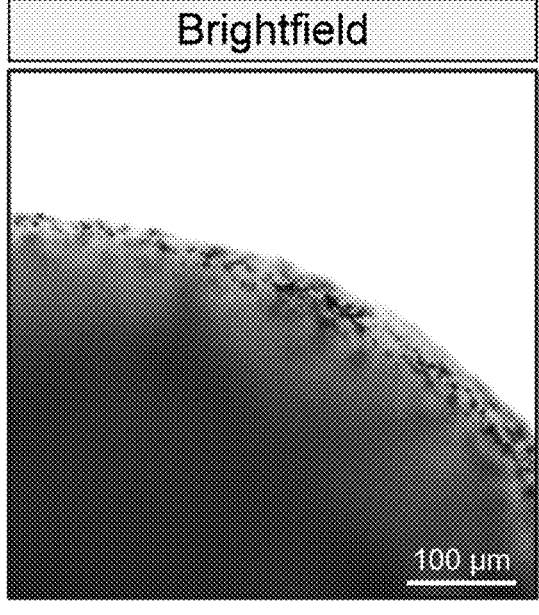
FIGS. 11A-11D. The effect of MNPs on neural organoids is limited.
Figure 11B:
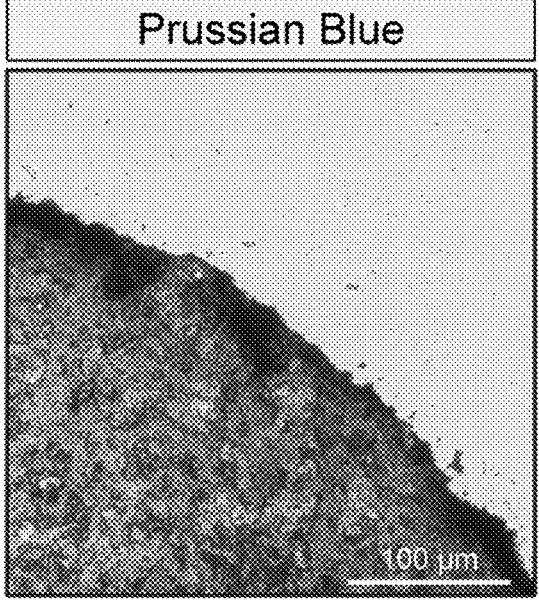
Figure 11C:
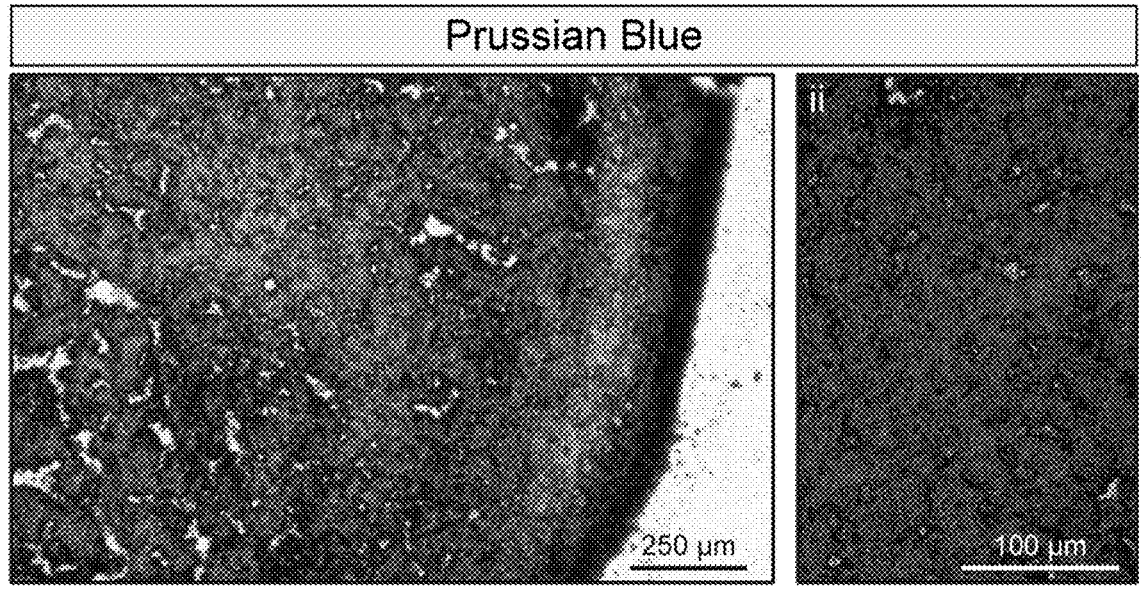
Figure 11D:
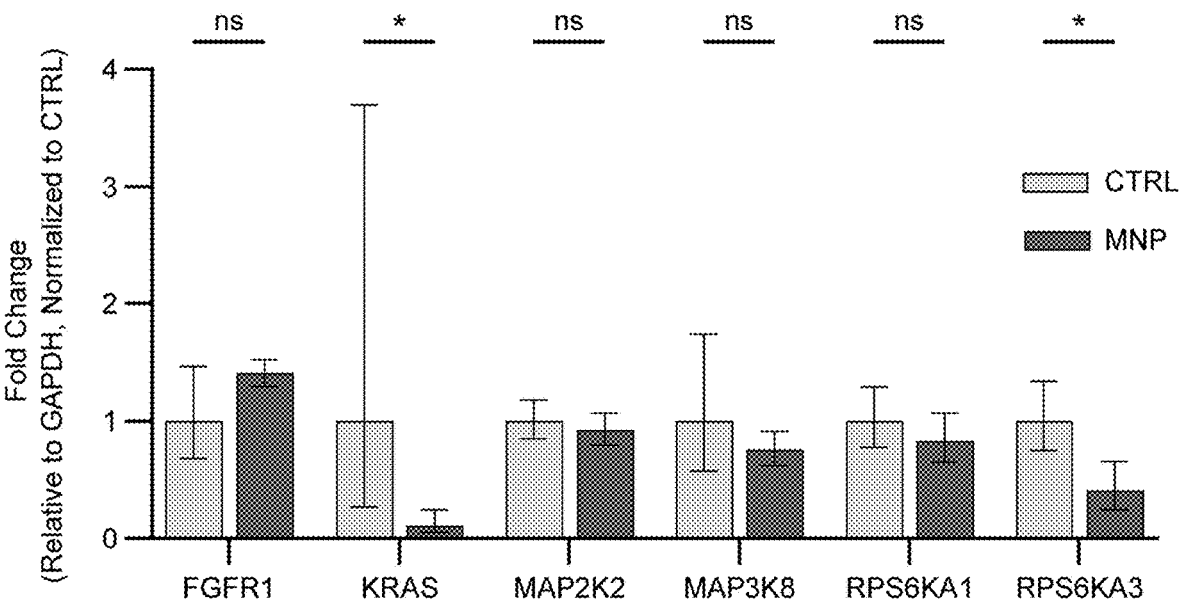

To support magnetic bioprinting, a potential cytocompatible ink material should: (i) undergo viscous thinning under an applied shear to allow for continuous dispensing of an MNP-laden ink through a syringe (ii) have a zero-shear viscosity that prevents MNP sedimentation over time scales relevant to coating multiple OBBs, (iii) encase the organoid fully once dispensed, and (iv) limit the degree of direct MNP contact with the organoid surface. A 0.025 percent by weight (wt %) solution of CNF exhibited a shear-thinning viscosity and significantly reduced MNP settling compared to 0.00 and 0.01 wt % CNF solutions (0.00 wt %: 64.1±0.9% dispersed, 0.01 wt %: 64.4±0.6% dispersed, 0.025 wt %: 82.0±3.5% dispersed over 15 minutes, p<0.0001) (FIGS. 2C, 2D). While the 0.10 wt % CNF ink solution resulted in significantly less MNP settling (97.3±2.3% dispersed, p<0.0001), it did not adequately encase the organoid due to its higher viscosity and, therefore, was less well suited to reproducible organoid lifting (FIG. 2E). Following 30 minutes of incubation, the 0.025 wt % CNF ink uniformly coated the organoid with MNP (FIGS. 8A, 11A). Qualitative evaluation of potential MNP uptake using Prussian blue staining of OBB cross-sectional slices demonstrated that the MNPs were primarily located at the periphery of the organoid without resulting in extensive intracellular localization of the iron particles (FIG. 11B). While iron was detected throughout the coated organoid, a similar distribution was observed in control neural organoids that had never been exposed to MNPs (FIG. 11C). Although iron oxide nanoparticles were previously shown to affect the MAPK signaling pathway in bone-derived MSCs[19], MAPK signaling in hiPSC-derived dorsal forebrain organoids was not affected by MNP surface coverage with STAMP (FIG. 11D).

2.5 Characterization of the CNF Support Scaffold and Organoid Release

In biofabrication, support scaffolds temporarily maintain the spatial positioning of cells within 3D space. To achieve this, support scaffolds must: (i) be shear-thinning so that the material yields as a deposition tool moves through the scaffold, and (ii) be self-healing after the deposition tool has passed to provide physical confinement to the OBB[14,20]. To create an optimal support scaffold, we sought to identify a material that was cytocompatible, bioinert to mammalian cells, and amenable to on-demand solubilization to release the encapsulated cellular structure after fabrication.

Figure 2F:
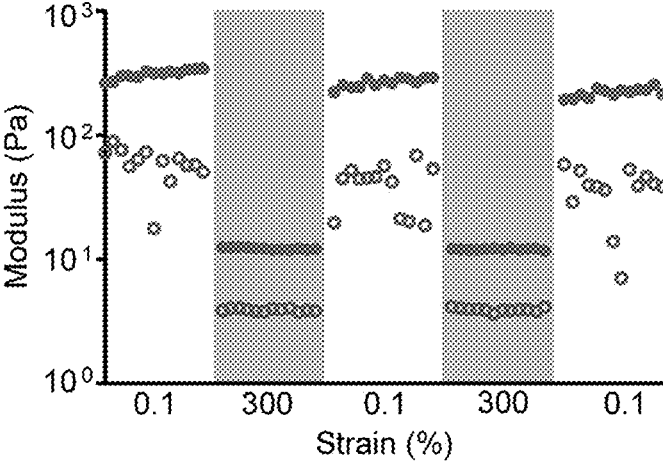
Figure 2G:
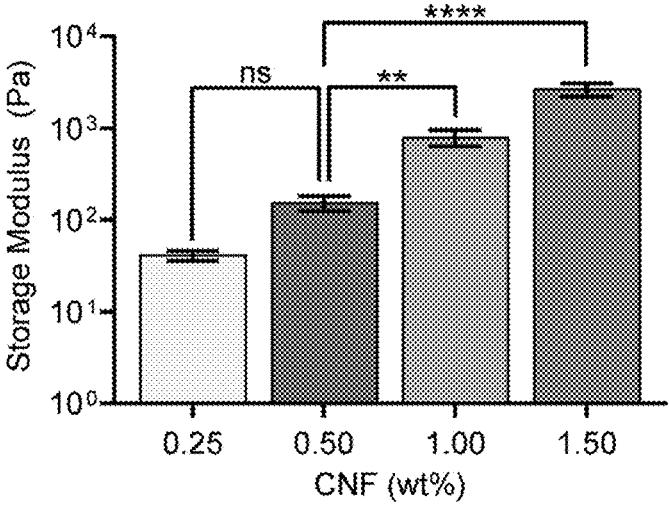
Figure 12A:
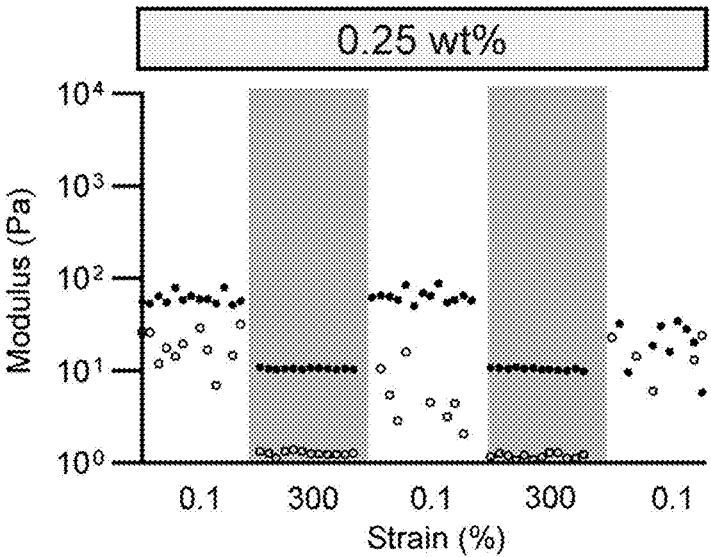
FIGS. 12A-12D. Modulus recovery following high strain for CNF support scaffolds.
Figure 12B:
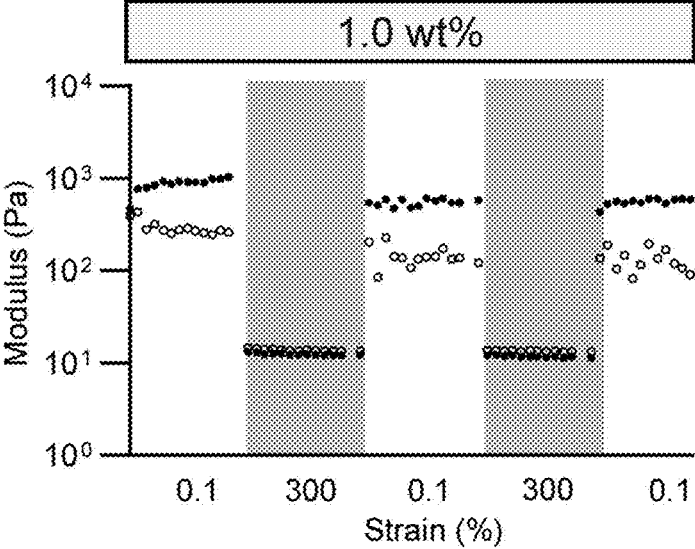
Figures 12C, 12D:
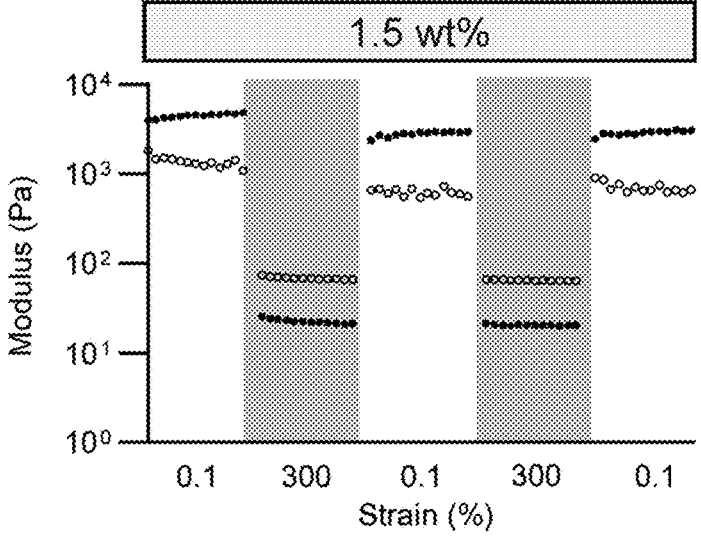

We evaluated the viscoelastic properties of a range of CNF solutions for use as a support scaffold. A concentration of 0.50 wt % CNF exhibited shear-thinning and self-healing properties without the need for additional chemical modifications or formulation additives (FIG. 2F). Moreover, the 0.50 wt % CNF demonstrated a greater recovery of modulus after high strain compared to 0.25 wt %, 1.0 wt %, or 1.5 wt % CNF (FIGS. 2F, FIG. 12). The reported stiffness of neural tissue varies as a function of sample age, brain region, and testing method, yet most studies report shear moduli ranging from several hundred to a few thousand Pa[21-23]. The wt % of CNF can be tuned to reproducibly vary the stiffness of support, and the 0.5 wt % CNF had a plateau storage modulus (G') of approximately 150 Pa (FIG. 2G).

Figure 2H:
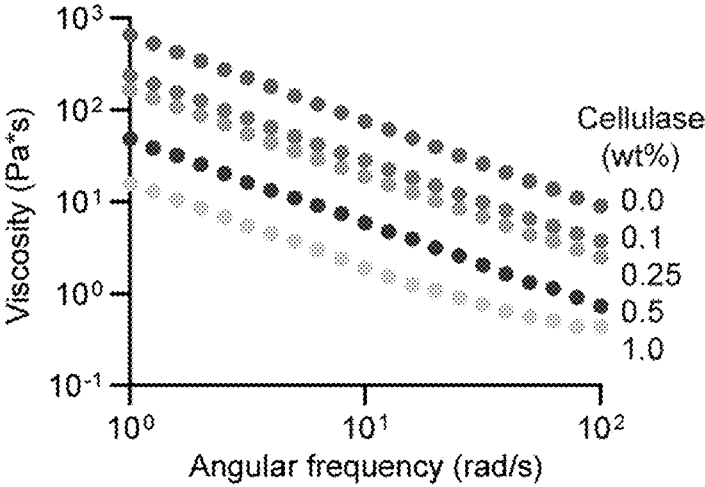
Figure 13A:
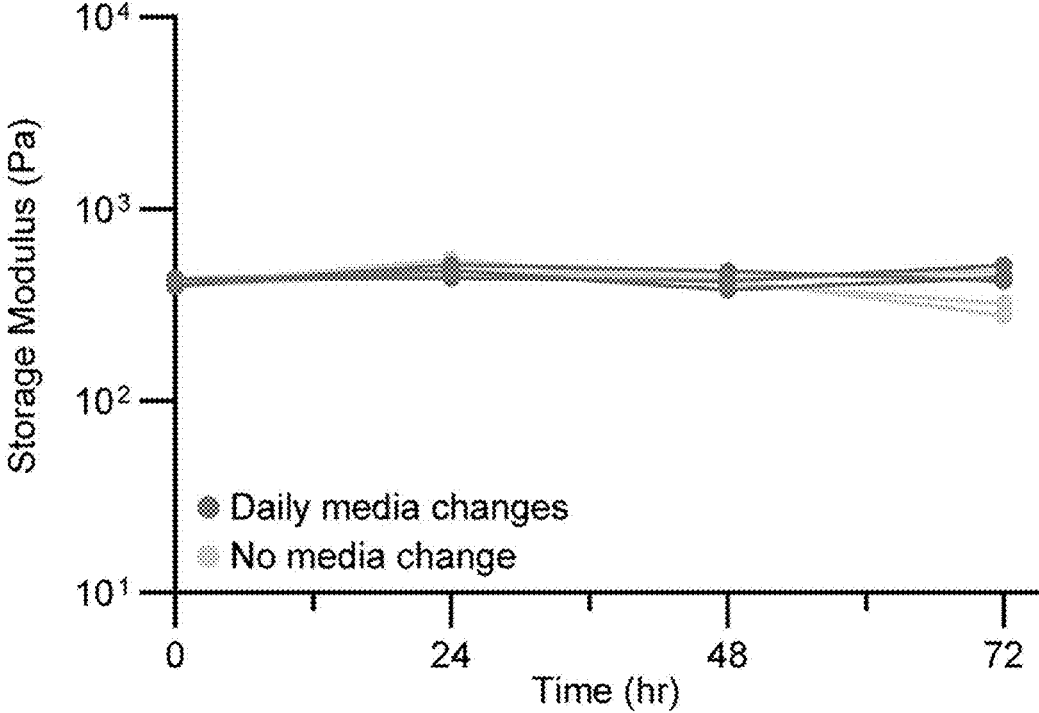
FIGS. 13A-13E. Cellulase degrades CNF in a bioorthogonal manner.
Figure 13B:
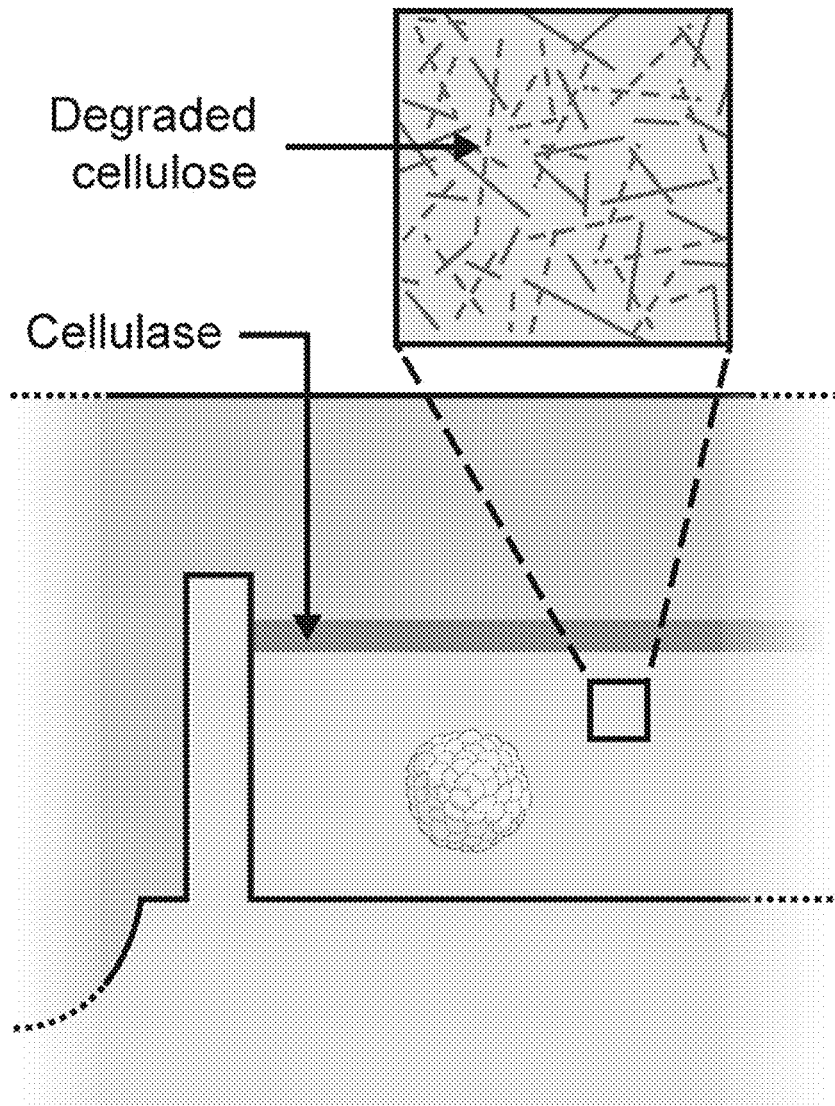
Figure 13C:
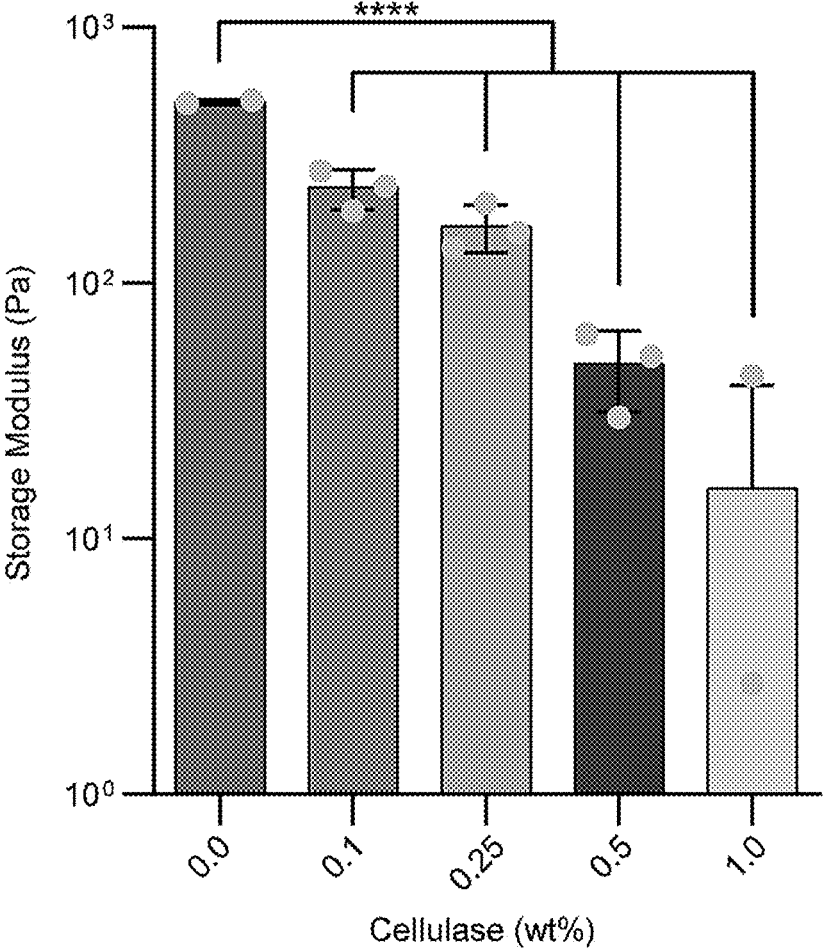
Figure 13D:
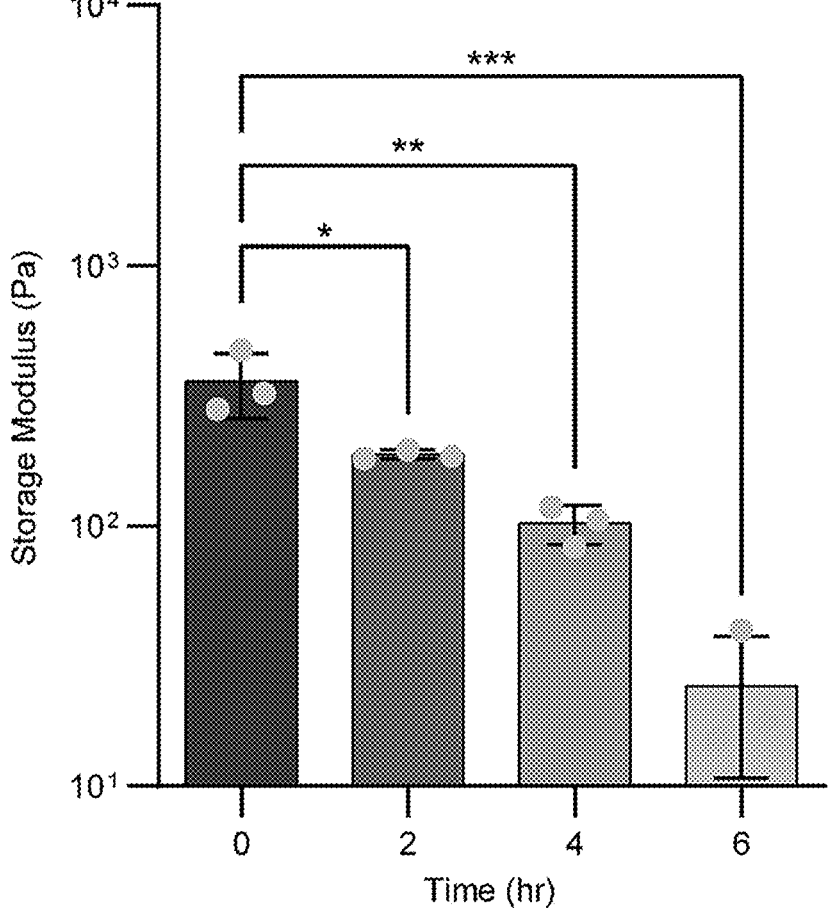
Figure 13E:
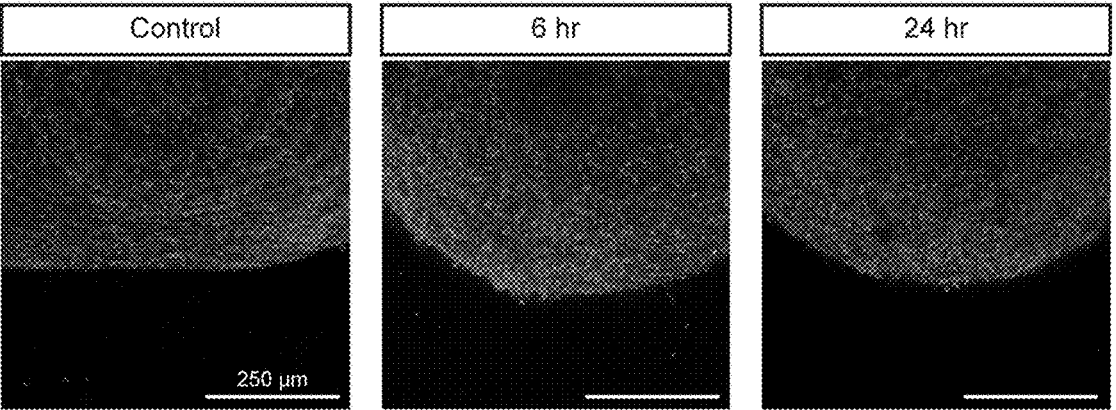
Figure 14A:
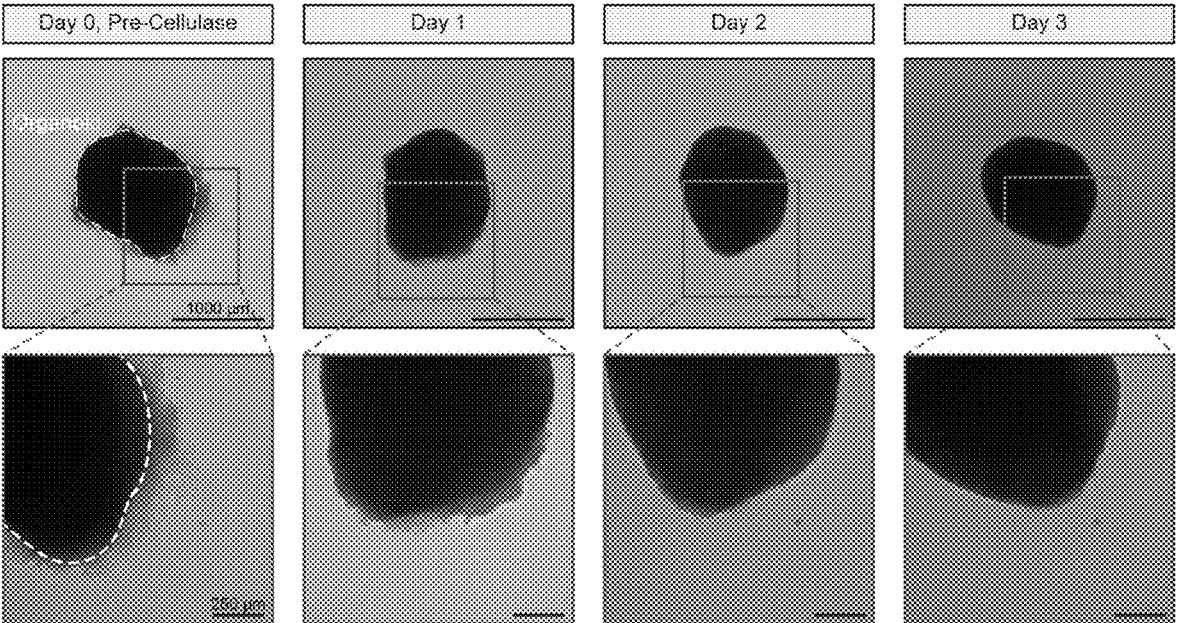
FIGS. 14A-14B. Cellulase-mediated removal of residual CNF.
Figure 14B:
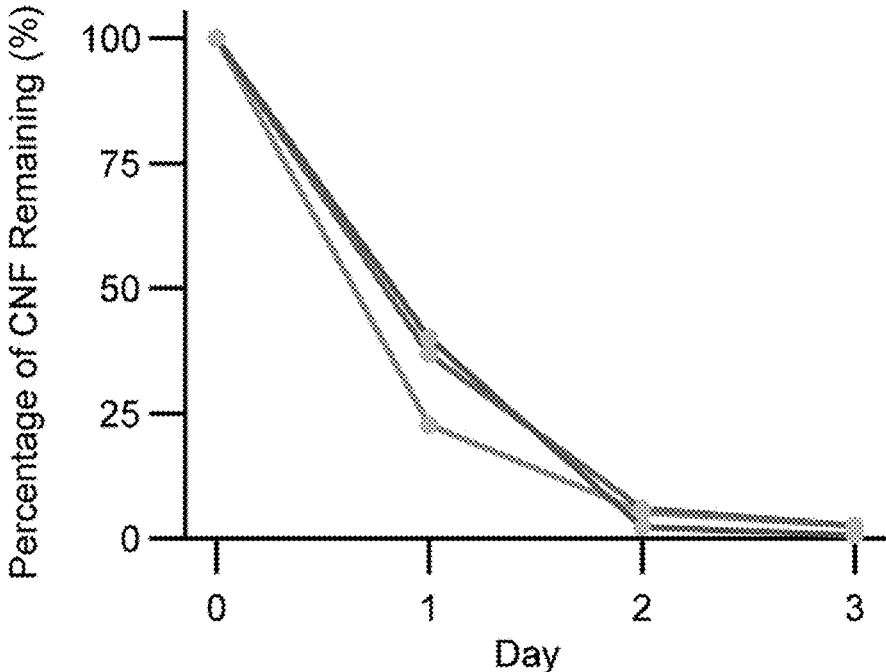

After being positioned, the fusion of constituent OBBs into a single assembloid can require multiple days during which the support scaffold should remain intact. The 0.5 wt % CNF support scaffold displayed a consistent range of storage moduli over 72 hours, both with and without daily media changes (FIG. 13A). Furthermore, the 0.5 wt % CNF support scaffold allowed for consistent media diffusion (Table 3). After OBB fusion, the resultant assembloid can be removed from the scaffold for downstream applications. Although recent efforts have begun to introduce polymers into the medium of regionalized neural organoids[24], to date, most studies have cultured organoids in suspension without the addition of exogenous biomaterials[18]. CNF, as a cellulose derivative, is amenable to cellulase-mediated degradation (FIG. 13B). Treating the CNF support with a range of cellulase concentrations resulted in stepwise decreases in both viscosity and storage modulus over time (FIG. 2H, FIG. 13C, 13D). Importantly, as cellulase activity is bioorthogonal to mammalian cultures, the addition of cellulase does not affect organoid viability (FIG. 13E). Once released from the CNF support bath with 0.5 wt % cellulase, neural organoids may remain sparsely coated in residual CNF; however, the addition of 0.5 wt % cellulase removes over 98% of the material over 72 hours (FIG. 14).

Figure 15:
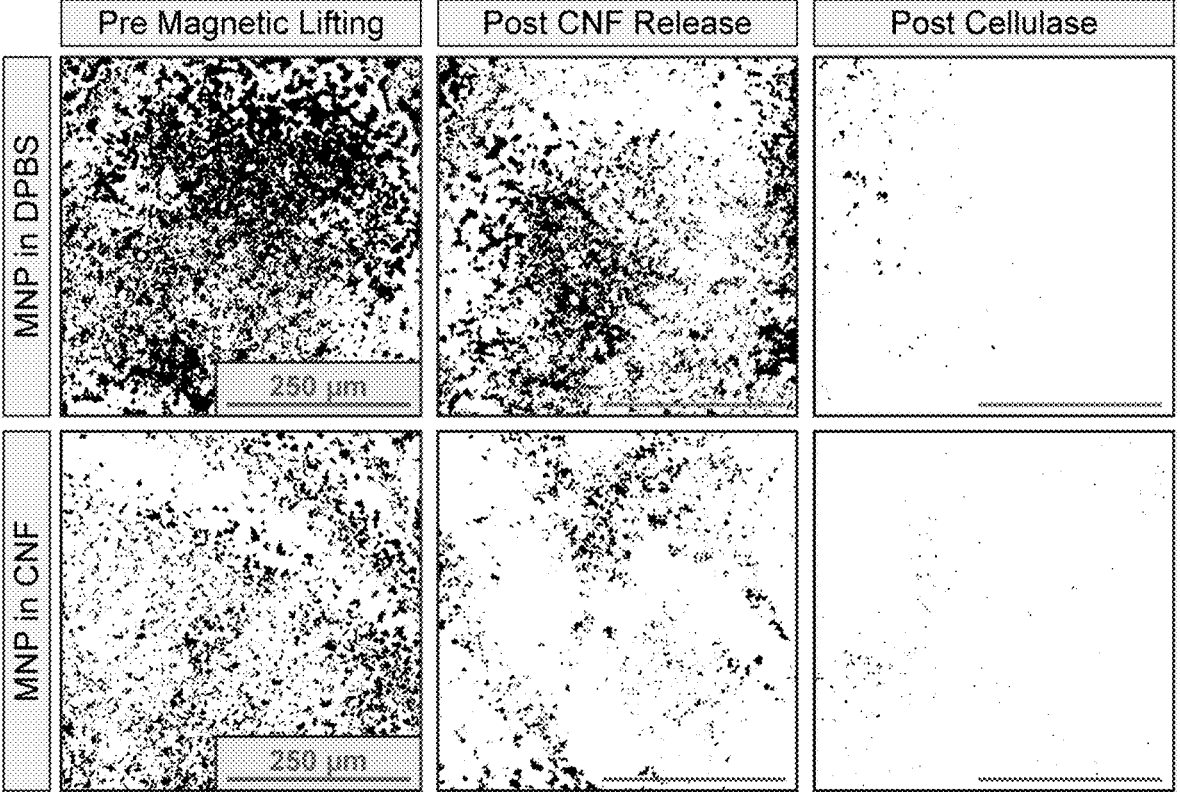
FIG. 15. MNP surface coverage throughout STAMP. Representative maximum projection, false colored BF images of neural organoid surfaces following STAMP wherein one organoid was coated with MNPs suspended in DPBS and the other with an MNP-laden 0.025 wt % CNF ink. In both cases, the initial concentration of MNPs in the coatings were 1 wt %.

Following the entire coating, lifting, transportation, deposition, and removal process, the majority of MNPs located on the surface of the neural organoids were no longer present (FIG. 15).

Figure 2I:
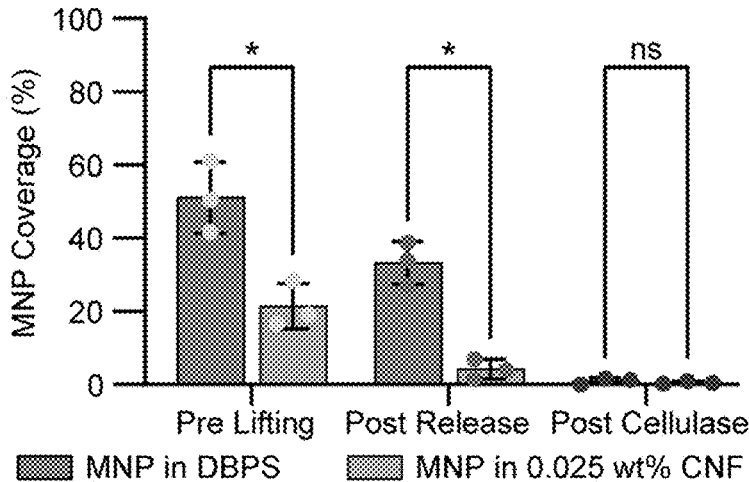
Figure 2J:
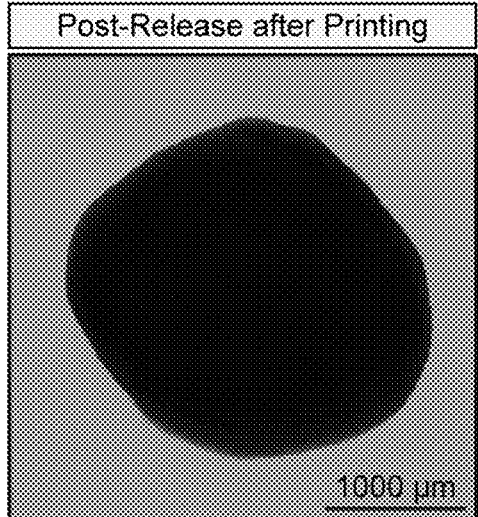

Moreover, by initially coating an organoid with an MNP-laden CNF bioink, as opposed to MNPs in solution, the degree of MNP attachment to the organoid surface significantly decreased (prior to lifting: p<0.05 between MNP and MNP in CNF, post release from CNF: p<0.05 between MNP and MNP in CNF, post cellulase treatment: p=0.851) (FIG. 2I). Finally, following STAMP, the neural organoids appear devoid of the gross deformations observed with AAB (FIG. 2J).

2.6 Utilizing STAMP to Construct Dorsal-Ventral Forebrain Assembloids

The construction of multi-region neural assembloids that begin to recapitulate the circuitry of the developing brain was first demonstrated in a collection of studies in 2017[2-4]. Since then, increasingly complex assembloids have revealed compelling, heretofore unobserved, disease-relevant phenotypes in vitro[5]. To demonstrate the unique capabilities of the STAMP platform, we sought to create dorsal-ventral forebrain assembloids with precise, reproducible control over the 3D positioning of the constituent OBBs.

Figure 16A:
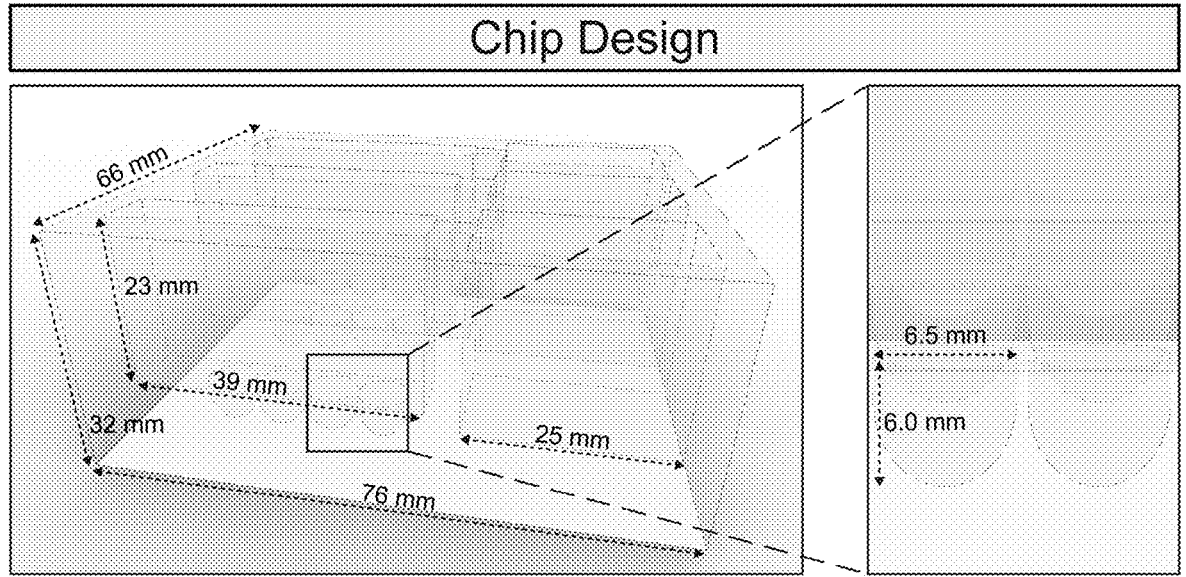
FIGS. 16A-16C. STAMP chip design and fabrication.
Figure 16B:
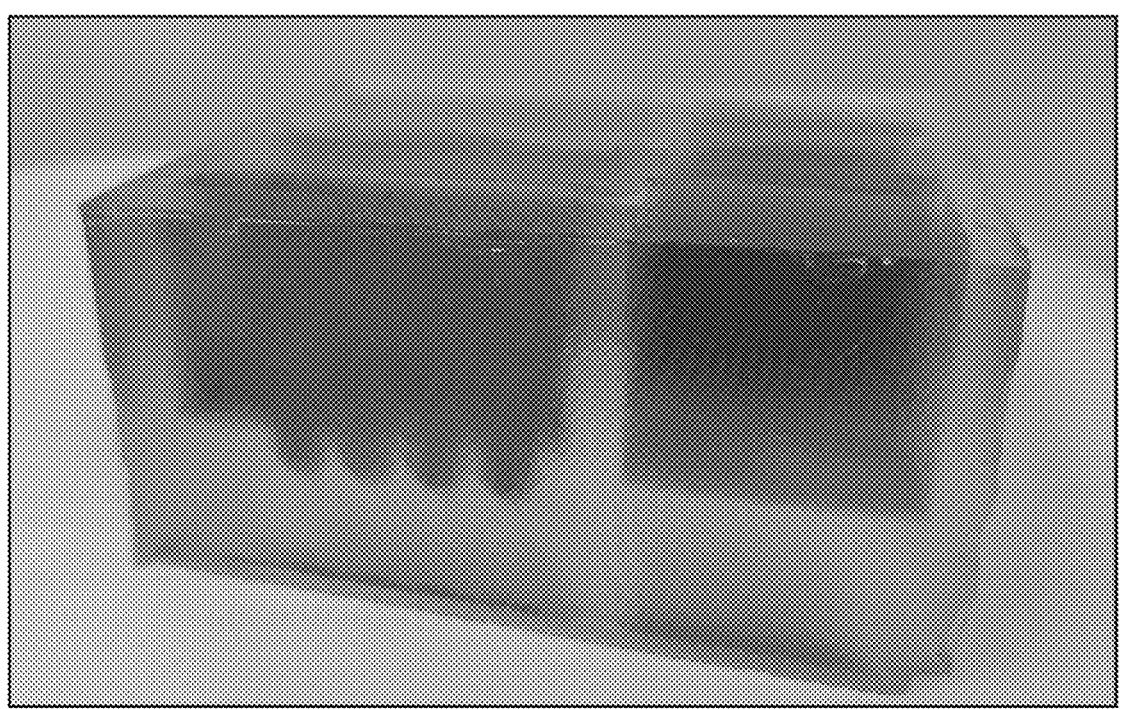
Figure 16C:
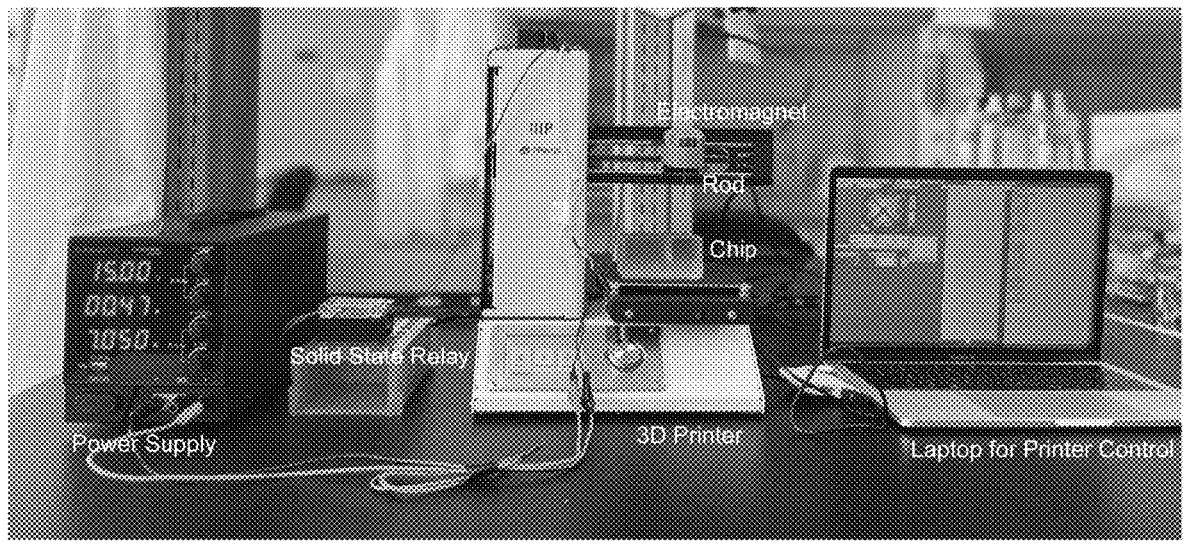

Each stage of OBB lifting, transportation, and deposition with STAMP can be performed manually or through automation. To facilitate automation, we created a custom PDMS chip with uniformly spaced wells and a support scaffold reservoir (FIGS. 16A, 16B). The chip includes several design elements, namely an offset platform for repeated medium addition, a series of elongated U-bottom wells, and a raised connector channel; collectively, these elements facilitate organoid maintenance prior to fusion, allow homogeneous MNP ink distribution during the coating phase, and maintain the OBB within a fully submerged medium, respectively. As the chip itself is fabricated from a 3D printed mold, it can be scaled in size to accommodate a wide assortment of assembloid sizes and shapes. The automation of the STAMP assembly process can be controlled by G-code, a widely used computer numerical control programming language, which reproducibly locates the organoids in the chip, lifts and deposits them within the support bath, and releases them at a user-specified location. G-code scripts are passed from a laptop (or microSD card) to a 3D printer that has been modified such that the conventional fan controls now trigger a solid-state relay to activate the electromagnet (FIG. 16C). When taken together, these components of the STAMP platform facilitate the reproducible, automatable construction of assembloids (FIG. 3A).

Figure 3B:
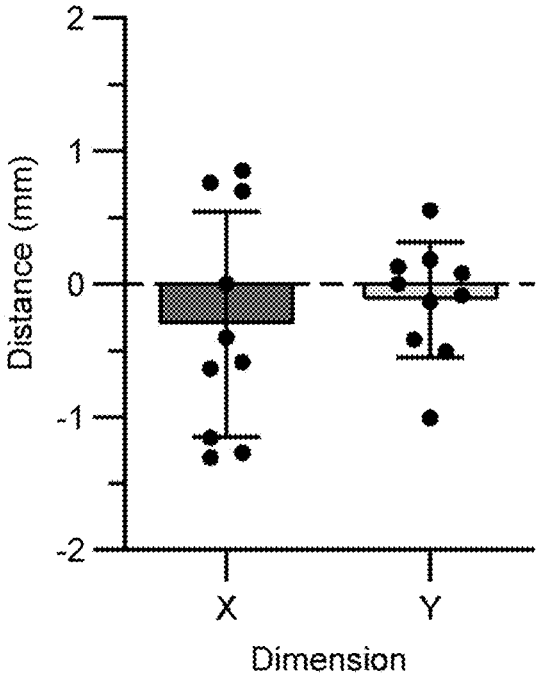
Figure 3C:
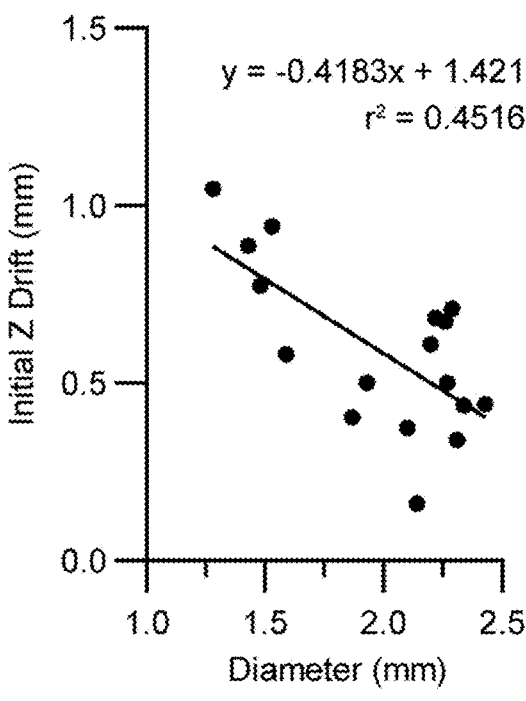
Figure 3D:
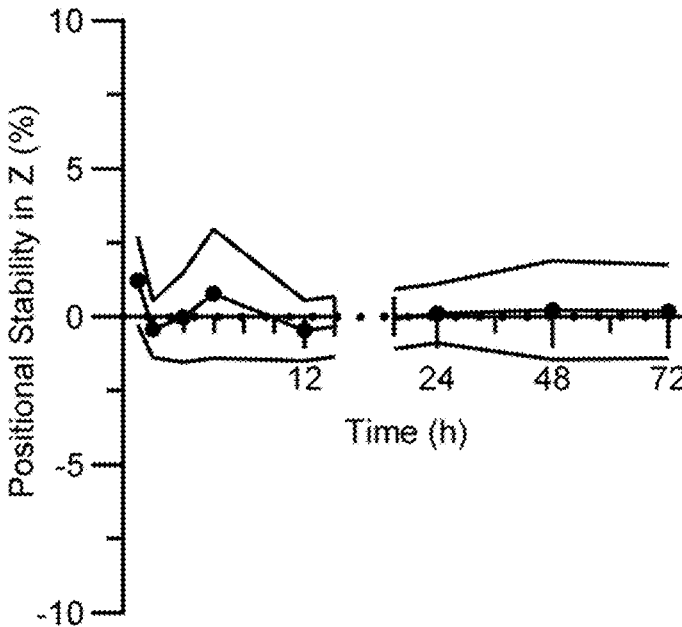
Figure 17A:
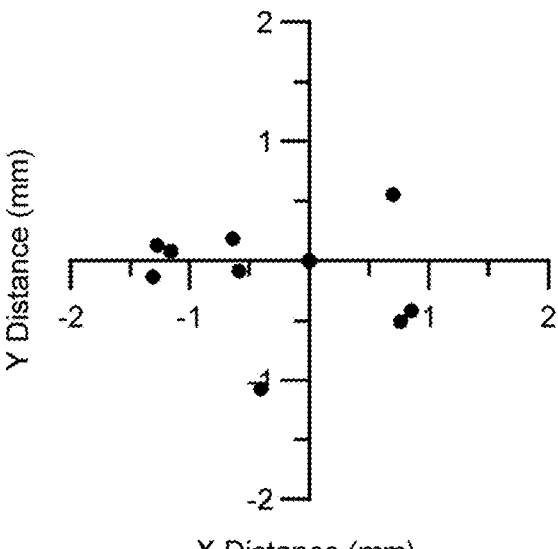
FIGS. 17A-17E. XYZ localization with STAMP.
Figure 17B:
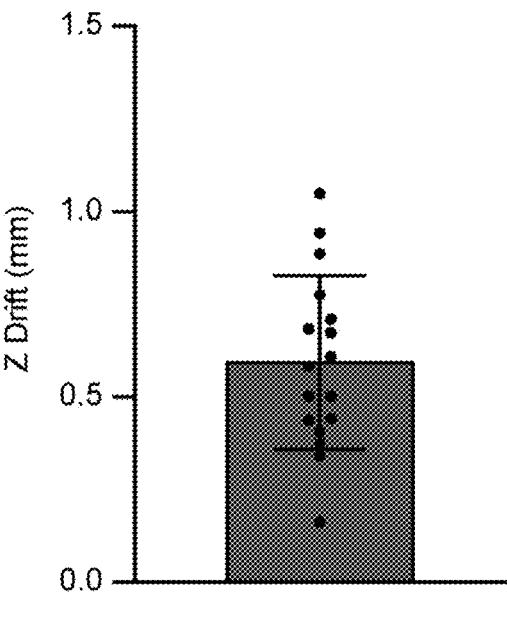
Figure 17C:
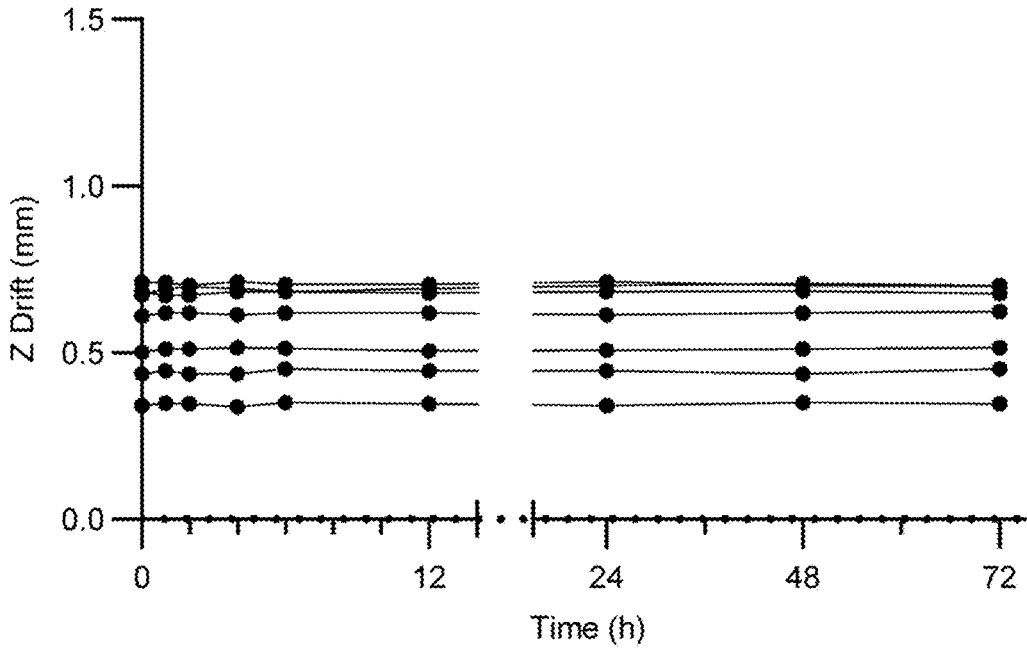
Figure 17D:
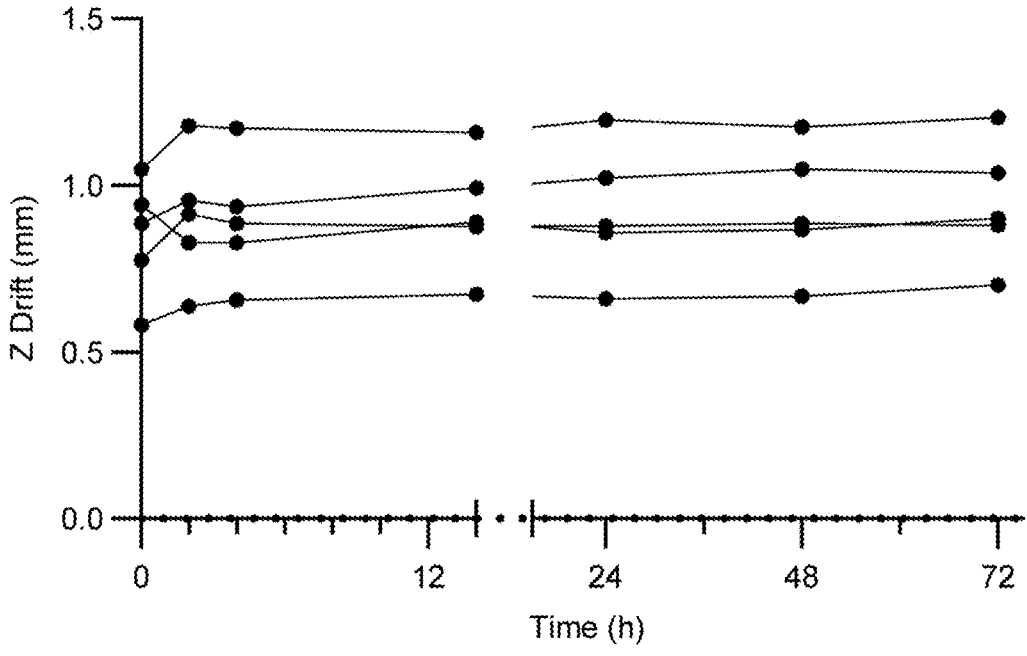
Figure 17E:
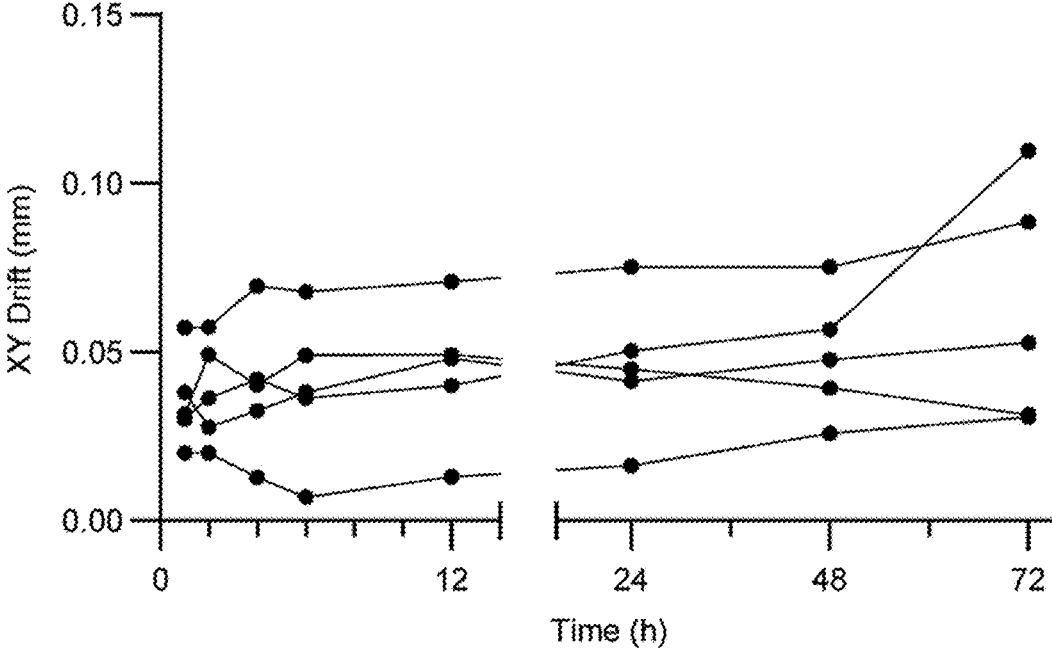

Spatial control over the position of constitutive OBBs is contingent on the precision, in all three dimensions, of both the initial placement and long-term movement of a given OBB. Using a spherical alginate microgel as a non-living, static model, we evaluated the initial drift of deposited spheres with similar diameters to neural organoids. Magnetic bioprinting was subject to initial drifts of −0.31±0.85 mm, −0.12±0.43 mm, and 0.59±0.23 mm in X-, Y-, and Z-directions, respectively (FIGS. 3B, FIG. 17A, 17B). Interestingly, as the diameter of the microgel increased from 1.3 to 2.5 mm, the initial Z drift decreased, suggesting that neural organoids, which tend to exhibit diameters approaching and exceeding 2 mm, may undergo decreased drift as they grow (FIG. 3C). After deposition, the OBBs must remain immobilized within the support scaffold to permit fusion into a cohesive structure. For neural organoids, fusion is consistently observed over the course of 72 hours. During this time, the positional movement in along the Z-direction was less than 5% FIG. 3D) and was consistent across replicates (FIGS. 17C, 17D). Additionally, the total XY drift over 72 hours was minimal (0.044±0.0.021 mm) (FIG. 17E).

Figure 3E:
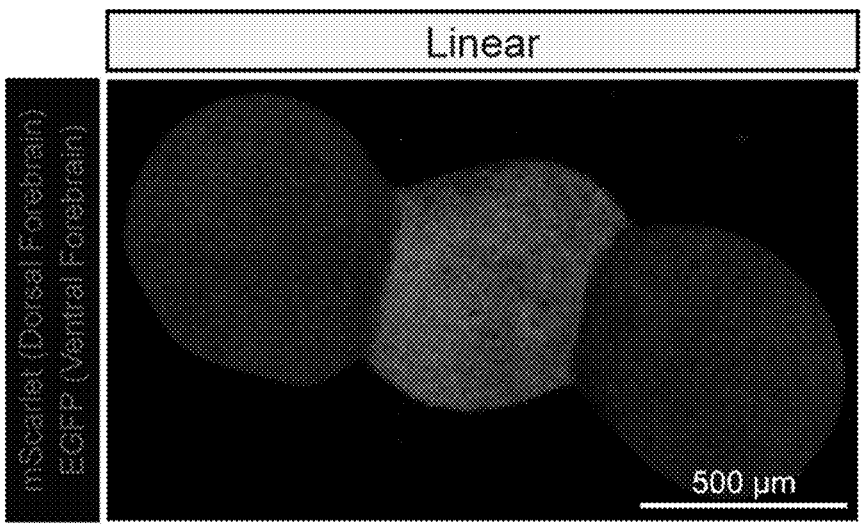
Figure 3F:
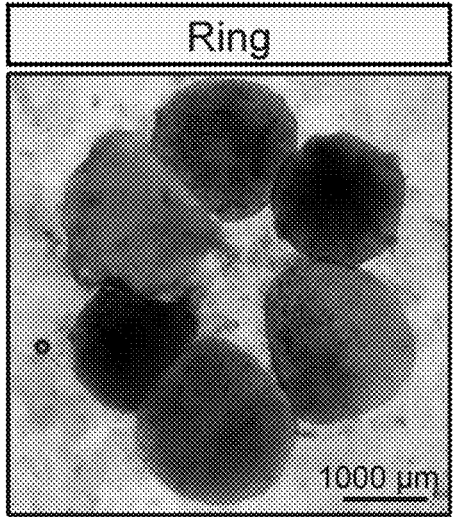
Figure 3G:
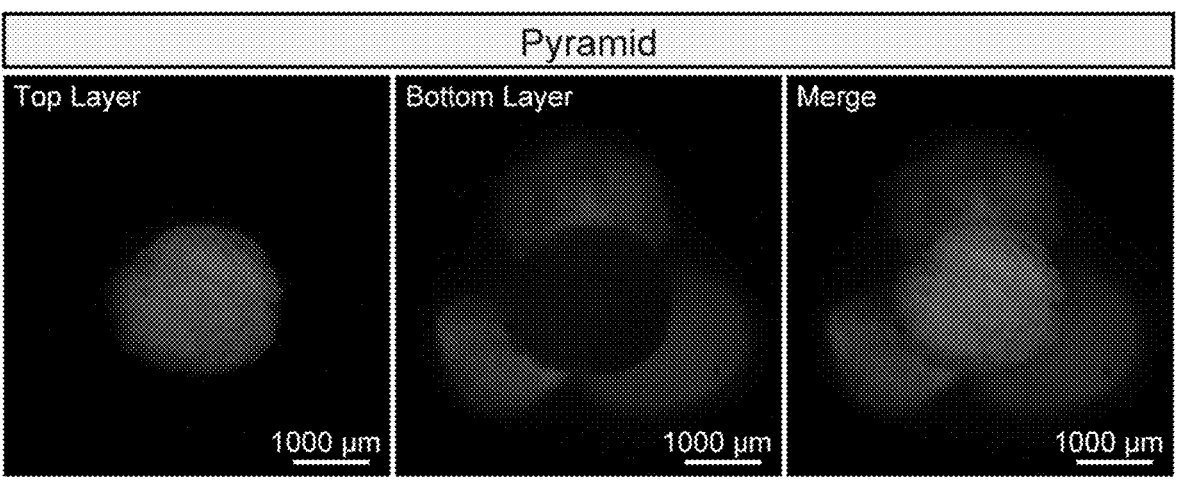

To demonstrate the multi-dimensional spatial control achieved by the STAMP platform, we manually constructed human dorsal-ventral forebrain assembloids from hiPSC lines that constitutively expressed either mScarlet or eGFP. Fusion was successful across a range of shapes that could not be easily fabricated using current approaches. For example, linear three-part assembloids were constructed with a pre-determined OBB sequence, and six individual neural organoids, derived from three hiPSC lines and differentiated into two domains of the forebrain, were arranged and fused to form a ring-like structure (FIGS. 3E, 3F). Due to the positional stability of the OBBs within the support scaffold, biofabrication of multi-layered structures such as pyramids was also possible (FIG. 3G).

Figure 3H:
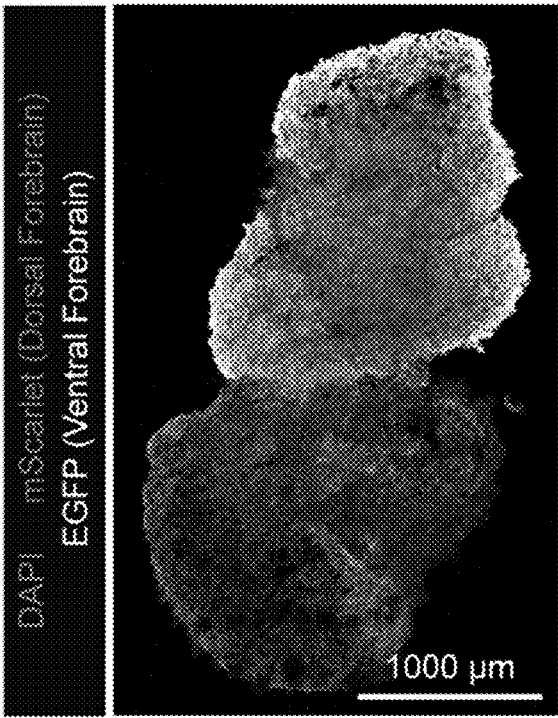
Figure 3I:
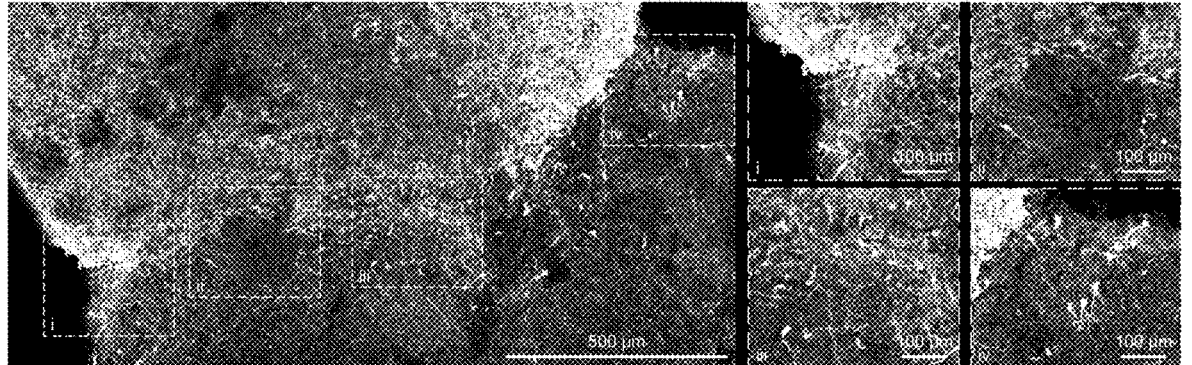

The cerebral cortex can be conceived of as a collection of circuits composed of excitatory glutamatergic neurons derived from the dorsal forebrain and inhibitory GABAergic interneurons derived from the ventral forebrain. The migration of these interneurons into the human cortex occurs throughout fetal and postnatal development and has been implicated in the etiology of various neuropsychiatric disorders[25]. Previous studies have leveraged human iPSC-derived dorsal-ventral assembloids to characterize the impact of genetic mutations associated with autism spectrum disorder on the saltatory migration of interneurons[2]. Here, we observed the robust integration of iPSC-derived ventral forebrain organoids to dorsal forebrain organoids following their controlled spatial positioning within, and subsequent release from, a CNF support scaffold by magnetic bioprinting (FIG. 3H). Over the course of two weeks post-release from the CNF support scaffold, we observed extensive migration of GABAergic interneurons from the ventral region into the dorsal forebrain region of the assembloids (FIG. 3I). These migratory cells exhibited highly branched projections that spanned across a Z-depth as wide as 25 μm. In conclusion, regionalized hiPSC-derived neural organoids can be controllably positioned in 3D and exhibit cellular migration indicative of functional integration. Taken together, these observations lay the foundation for the use of STAMP as a platform for constructing complex neural circuits in vitro.

2.7 Bioprinting Patient-Derived Glioma Assembloids to Study Tumor Progression and Drug Response Organoid-based cancer models have emerged as a promising platform for maintaining inter- and intratumoral heterogeneity, enabling ex vivo investigation of patient-specific tumor progression[26,27]. The emergence, expansion, and treatment of cancer is influenced both by cell-cell interactions and the tumor microenvironment. To date, two approaches have been developed for recapitulating the tumor-host cellular microenvironment in vitro: (i) by leveraging genetic engineering strategies to induce oncogenic mutations, and (ii) by co-culturing tumor cells with organoid models of the tissue of origin or the tissue of metastasis. While these approaches permit temporal control over the interactions between tumor and host tissue, the STAMP platform would be particularly-well suited for controlling the spatial dynamics of infiltration and, as such, could serve as a complementary approach for building translational ex vivo models of cancer.

Diffuse intrinsic pontine glioma (DIPG) is a universally fatal pediatric cancer that arises in the ventral pons[28,29] and exhibits key molecular and genomic differences compared to adult high-grade gliomas[30-32]. Standardized protocols[33] have facilitated the use of patient-derived models that have helped identify promising therapeutic agents[34-36], yet additional experimental models, namely those which recapitulate the interactions between DIPG and the human tumor microenvironment, would be valuable. To demonstrate the potential for STAMP to facilitate studies characterizing the interactions between glioma and human neural tissue ex vivo, we created assembloids consisting of hiPSC-derived regionalized neural organoids and patient-derived DIPG organoids with distinct metastatic profiles.

Figure 4A:
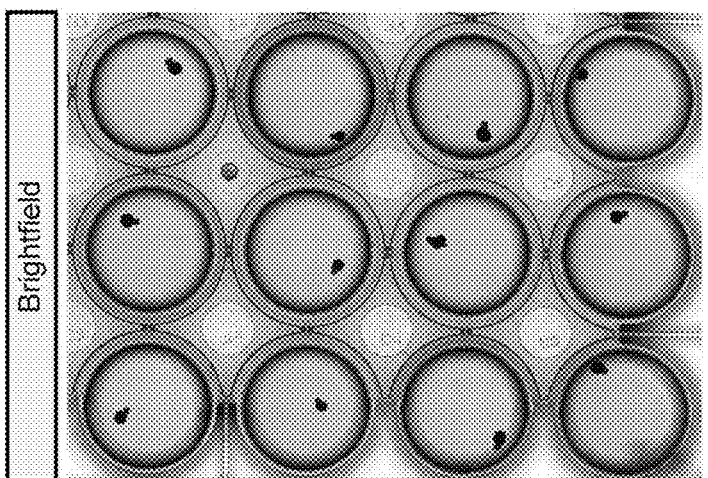
FIGS. 4A-4F. Glioma assembloids predict tumor progression specific drug response.
Figure 4B:
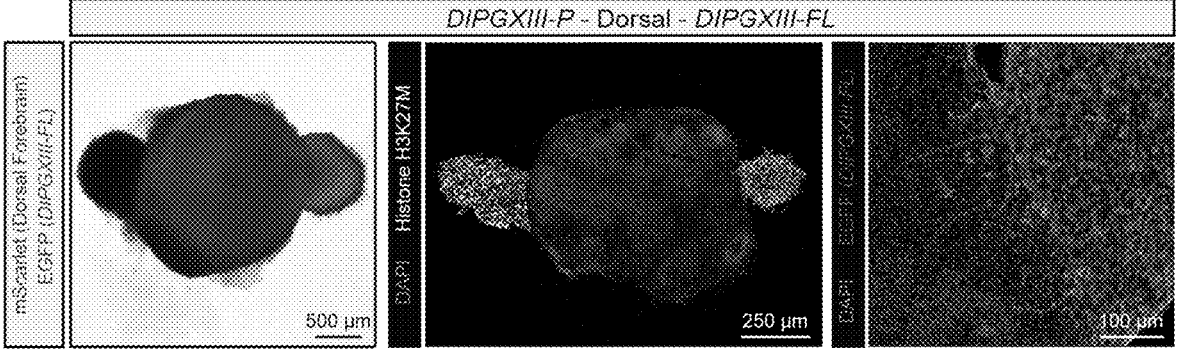
Figure 18:
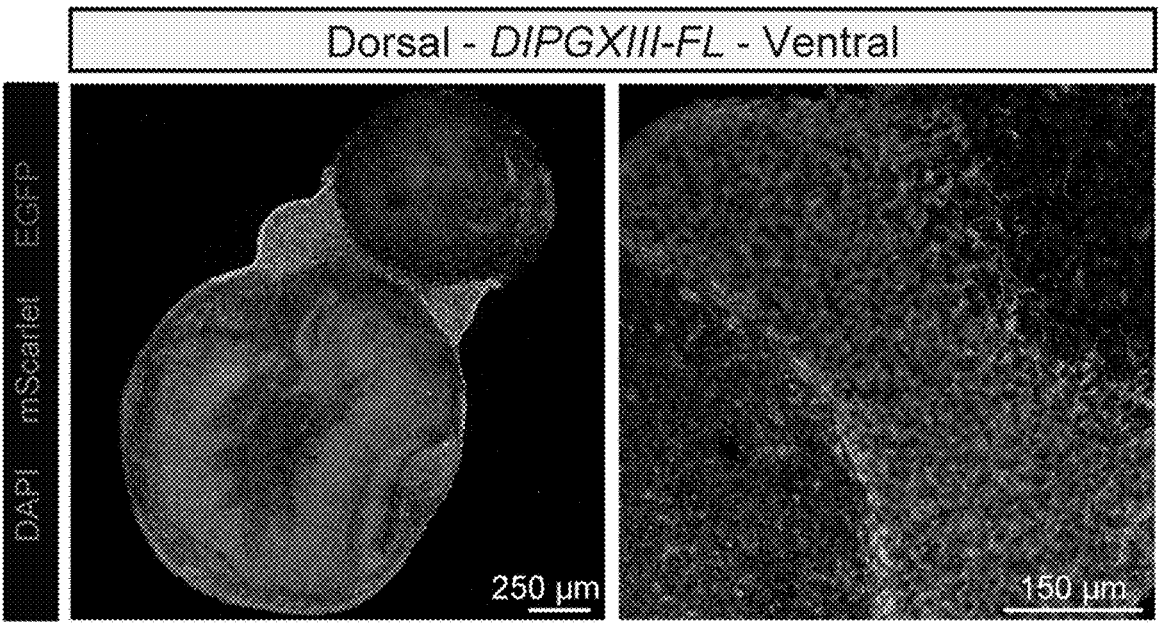
FIG. 18. Three-part fusion of two regionalized neural organoids and a DIPG organoid. Representative IF images of an mScarlet-expressing dorsal forebrain neural organoid fused to an eGFP-expressing frontal lobe DIPG metastasis fused to a non-fluorescent ventral forebrain neural organoid.
Figure 19:
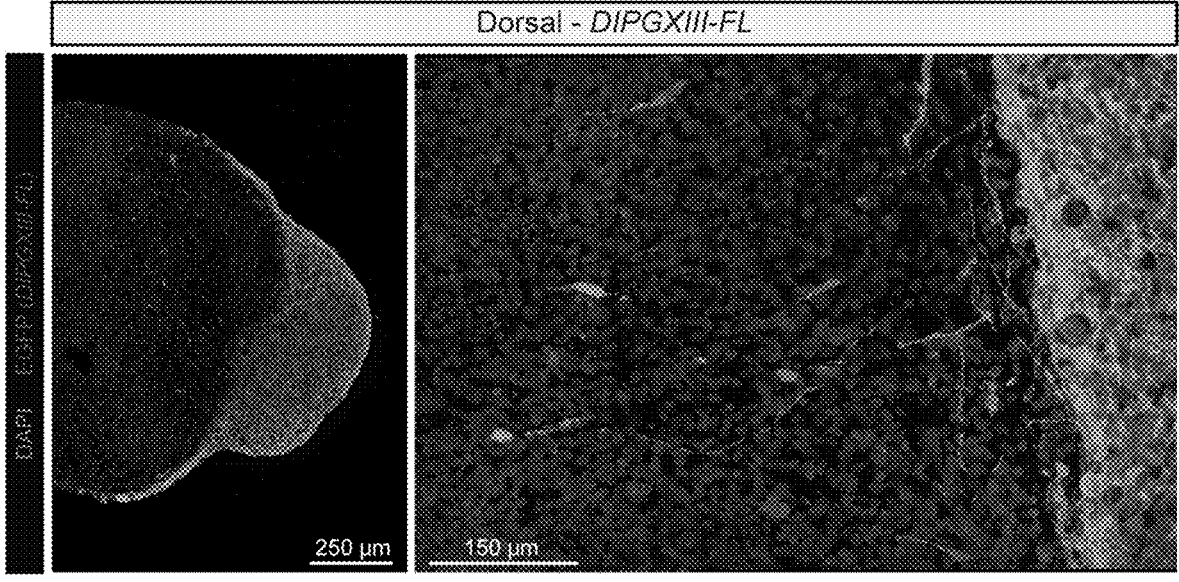
FIG. 19. Infiltration of a DIPG organoid into a neural organoid. Representative IF images of an eGFP-expressing frontal lobe DIPG metastasis fused to a non-fluorescent dorsal forebrain neural organoid.

The magnetic bioprinting-enabled localization and subsequent fusion of neural organoids with DIPG organoids was reproducible and scalable (FIG. 4A). As with the multi-region assembloids constructed with STAMP, neuro-DIPG assembloids remained intact after cellulase-mediated release from the CNF support bath. Importantly, the spatial control imparted by the STAMP platform allowed for the creation of assembloids wherein forebrain organoids were integrated with DIPG organoids derived from two distinct brain regions of a single patient: 1) the tumor origination site, the pons (DIPGXIII-P), and 2) a distant brain region, the frontal lobe (DIPGXIII-FL), into which the tumor metastasized[37]. As a proof of principle demonstration, we created an assembloid consisting of the pontine DIPG organoid, a dorsal forebrain neural organoid, and a frontal lobe DIPG organoid (FIG. 4B). The substitution to methionine in histone H3 at lysine 27 (H3K27M), a hallmark of diffuse midline pediatric gliomas[38,39], was predominantly observed within the tumor organoid, and robust infiltration of GFP-expressing DIPG projections was observed at the tissue interface one-week post-fusion. Similar three-part assembloids were created by integrating dorsal and ventral forebrain organoids with a frontal lobe DIPG organoid (FIG. 18). These three-part assembloids have the potential to serve as unique tools for investigating tumor infiltration and drug response across a range of therapeutically relevant variables including tumor metastatic state and brain region. Tumor infiltration, in both two-part and three-part assembloids, was characterized by the migration of H3K27M-expressing DIPG nuclei into the periphery of the neural organoid and the extension of GFP-expressing projections deeper into the neural organoid (FIG. 19). As previous studies of DIPG metastasis have relied upon either patient-derived orthotopic xenografts or genetically engineered mouse models[40,41], these assembloids represent the first ex vivo, entirely human models of DIPG infiltration into neural tissue.

Figure 20:
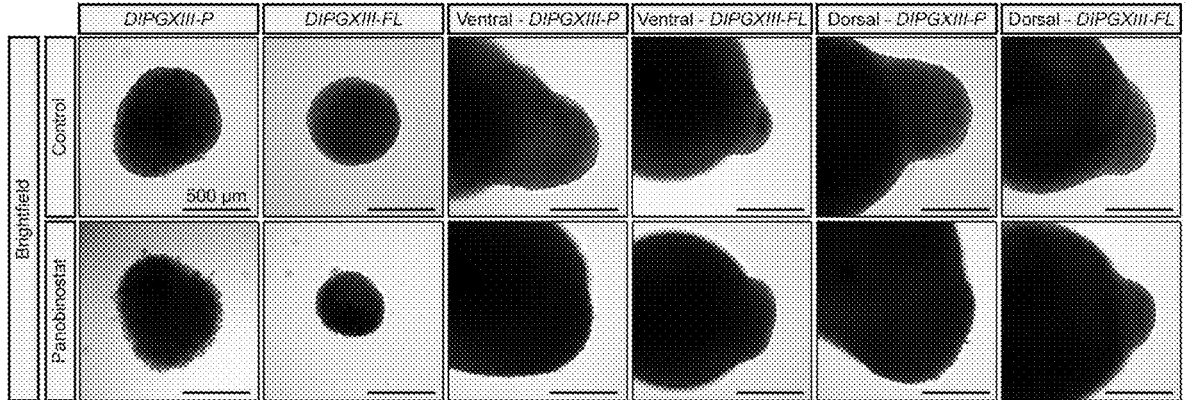
FIG. 20. DIPG organoids fused to an array of neural organoids. Representative BF images of DIPG organoids, from the pons and frontal lobe, fused to ventral and dorsal neural organoids with and without 200 nM panobinostat.

To illustrate the utility of the STAMP platform in translational studies, we created an array of neuro-DIPG assembloids. These assembloids included multiple permutations of DIPG progression (i.e., originating pons and metastatic frontal lobe) and multiple neural organoid types (i.e., dorsal and ventral forebrain). Subsequently, we treated the assembloids with panobinostat, a multiple histone deacetylase (HDAC) inhibitor that has recently been identified as a potential therapeutic for DIPG[34,36] and is currently in several clinical trials (NCT02717455, NCT04341311, NCT04804709, NCT05009992) (FIG. 20).

Figure 4C:
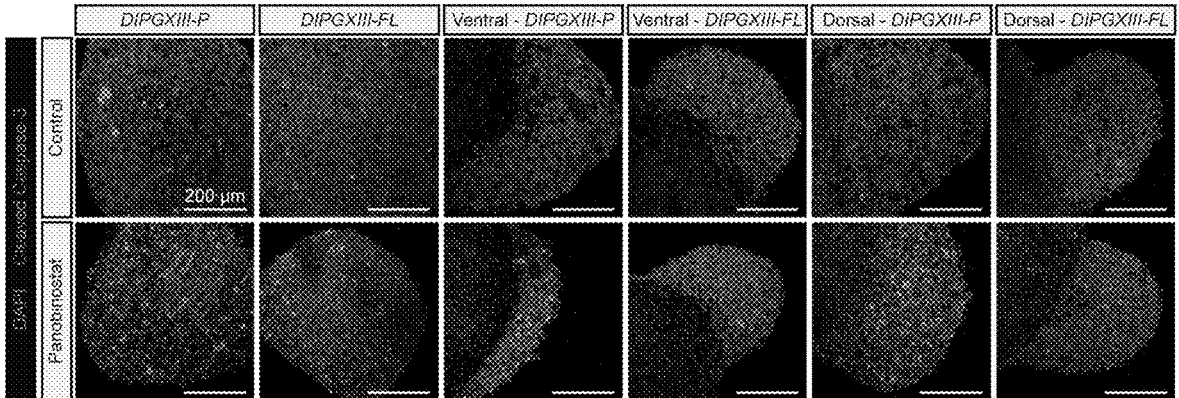
Figure 4D:
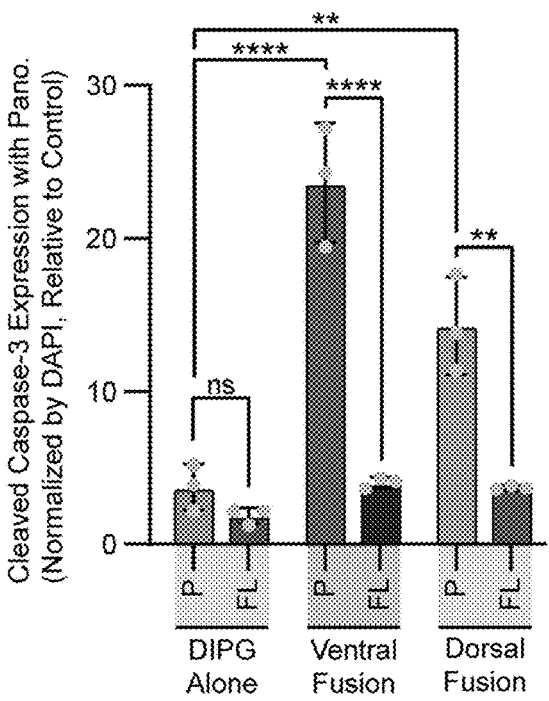
Figure 21:
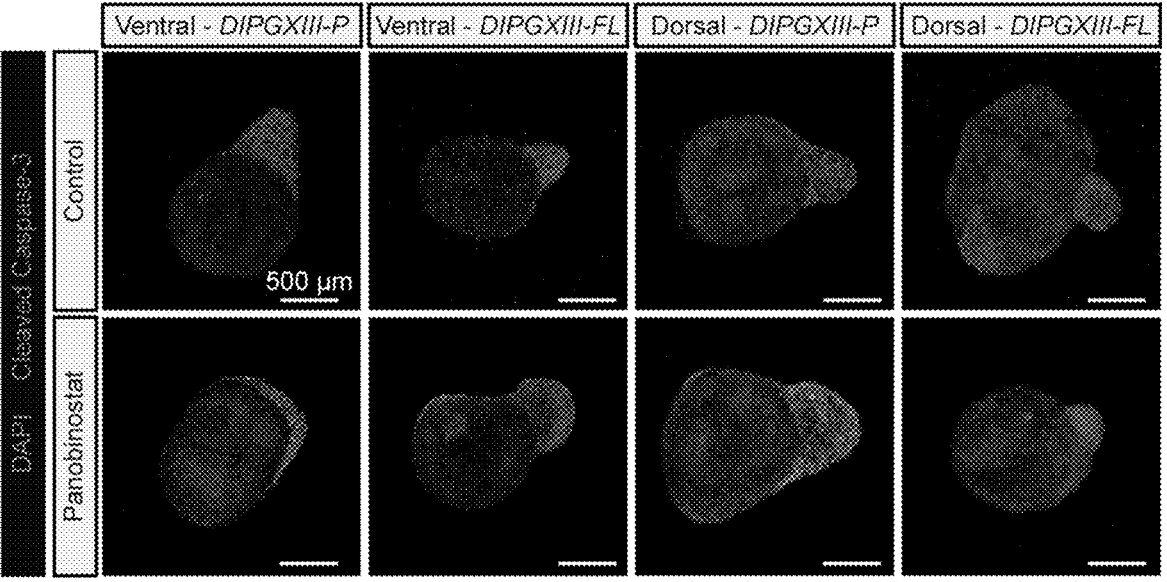
FIG. 21. Panobinostat does not induce substantial apoptosis in neural organoids. Representative IF images stained with the apoptosis marker cleaved caspase-3 of DIPG organoids, from the pons and frontal lobe, fused to ventral and dorsal neural organoids with and without 200 nM panobinostat.

As panobinostat was shown to decrease DIPG viability in vitro[34,36], we characterized the expression of the apoptosis marker cleaved caspase-3 in DIPG organoids following assembly and after panobinostat treatment (FIG. 4C). All DIPG organoids treated with panobinostat expressed higher levels of cleaved caspase-3 compared to untreated controls. Moreover, the adjacent neural organoids did not exhibit substantially increased cleaved caspase-3 expression following panobinostat treatment (FIG. 21). No statistically significant differences were observed between pontine and frontal lobe DIPG organoids in isolation (p=0.996); however, when fused to either dorsal or ventral neural organoids, pontine DIPG organoids expressed significantly higher levels of cleaved caspase-3 compared to frontal lobe DIPG organoids (ventral fusion: p<0.0001, dorsal fusion: p<0.01) (FIG. 4D). This suggests that panobinostat may induce greater degrees of apoptosis in DIPG cells that have not yet metastasized. Critically, this difference was only observable in assembloids, as opposed to the isolated DIPG organoids, highlighting the need for recapitulating cell-cell interactions.

Figure 4E:
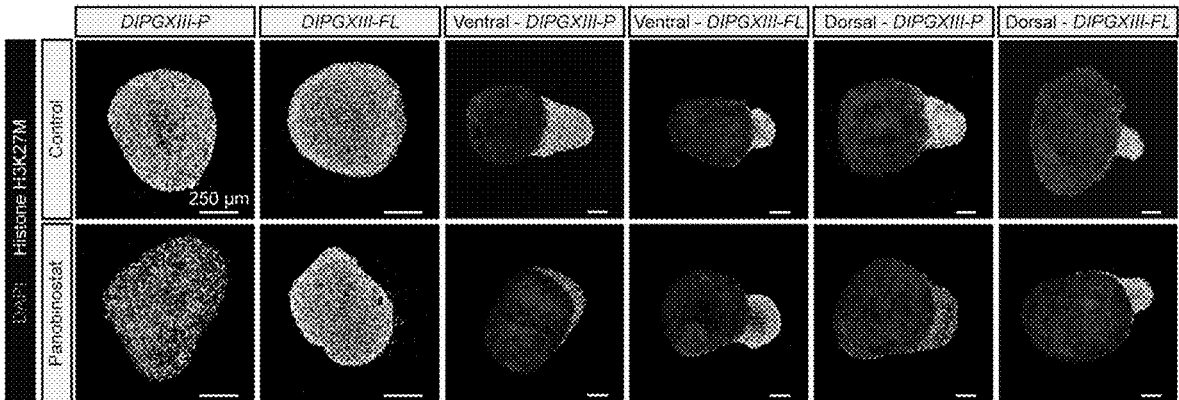
Figure 4F:
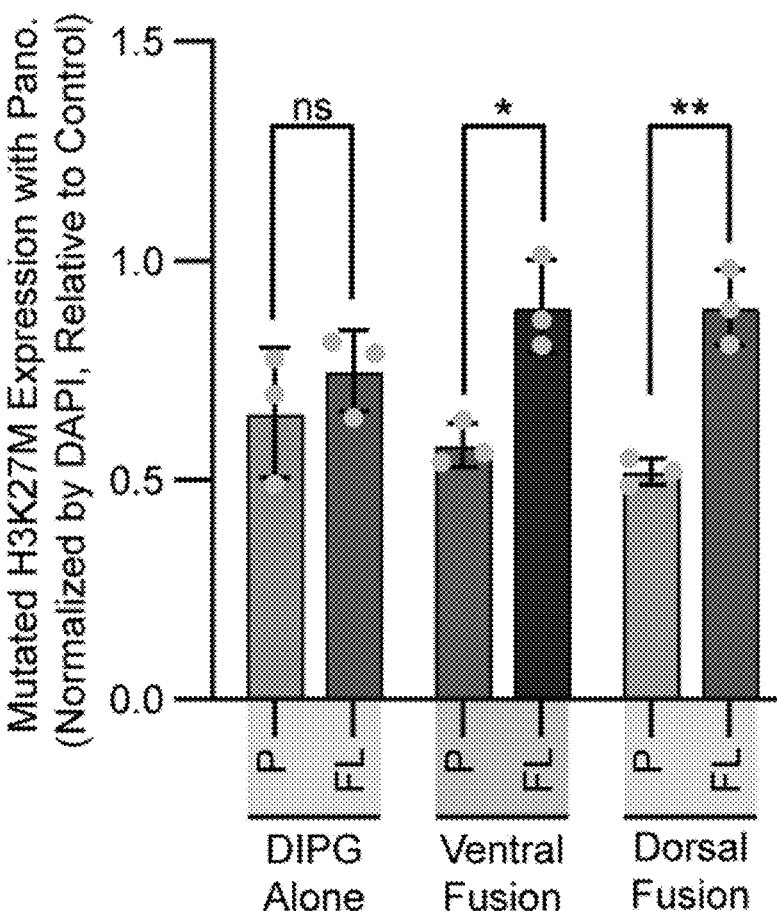

The H3K27M mutation perturbs polycomb repressive complex 2 resulting in global hypomethylation of K27 and DIPG oncogenesis[42-49]. As an HDAC inhibitor, panobinostat rescues the hypotrimethylation phenotype, which should specifically target DIPG cells with the H3K27M mutation. Given panobinostat's proposed mechanism of action and the observed differences in cleaved caspase-3 expression, we hypothesized that panobinostat treatment may deplete H3K27M populations within pontine DIPG organoids to a greater extent than frontal lobe DIPG organoids when fused to neural organoids. Accordingly, the H3K27M expression within isolated DIPG organoids was decreased following panobinostat treatment; however, it did not exhibit significant differences as a function of their metastatic profile (p=0.983) (FIGS. 4E, 4F). Conversely, H3K27M expression within assembled pontine DIPG organoids was significantly lower than that within assembled frontal lobe DIPG organoids following panobinostat treatment (ventral fusion: p<0.05, dorsal fusion: p<0.01). Taken together, these data suggest that panobinostat drives a disproportionate loss of DIPG cells with the H3K37M mutation in assembloids wherein the tumor organoid was derived from the originating tumor site. Further studies may be able to leverage STAMP as a platform for exploring additional brain region- or tumor-specific therapeutic modalities.

3. Discussion

Collective tissue behaviors, ranging from morphogenesis to tumor infiltration, are dependent upon cell-cell and cell-microenvironment interactions[50]. These processes are starting to be modeled in self-organizing organoid and assembloid models[1]. However, as we move towards recapitulating increasingly complex, multi-lineage interactions in vitro, synergizing advances in OBB creation with innovations in biofabrication will prove to be critical[18]. Here, we demonstrate that hiPSC-derived regionalized neural organoids as well as patient-derived glioma organoids can be controllably positioned in 3D with STAMP to create multiple types of assembloids.

This novel magnetic bioprinting approach is inspired by previously reported pick-and-place biofabrication techniques, namely AAB[13-16]. Compared to vacuum aspiration mediated OBB printing, STAMP reduces the concentrated localization of force on the tissue surface and is therefore uniquely suited for OBBs with low resistance to deformation and applications in which the cytoarchitecture of the OBB is relevant to the physiology of interest. Additionally, whereas AAB is predicated upon manual selection of OBBs within a media reservoir, STAMP utilizes a custom chip design with microwells for each OBB. This allows for the potential use of G-code to automate locating, lifting, and depositing the OBBs at a specified location within the support bath. It should be noted that the fusion of OBBs has also been previously achieved with the Kenzan method in which an OBB is aspirated, impaled with a metal microneedle, and, over the course of multiple such piercings with additional OBBs, fused into a single assembloid[51]. While this approach has been automated and commercialized, its dependency on puncturing the OBB and the concomitant deformation of the punctured OBB severely undermines its use for OBBs with conserved, biologically relevant cytoarchitecture. Moreover, this approach is limited in the complexity of OBB configurations it can create given the rigidity of the needles. Taken together, when compared to other OBB printing technologies, STAMP is a substantial improvement as it introduces spatial fidelity in 3D without damaging the constitutive OBB.

STAMP aims to serve as a complementary approach to conventional assembloid formation protocols that are dependent on the fusion of organoids due to confinement within a microcentrifuge tube[9]. While these protocols rely upon reagents and equipment readily available in most biology laboratories, the simplicity of the assembly itself limits the degree of control imparted over the spatial positioning of the OBB. Moreover, while linear assembloids composed of up to three distinct OBBs have been demonstrated[6], building assembloids in X, Y, and Z dimensions remains a challenge. As such, when compared to current state of the art OBB assembly protocols, magnetic bioprinting has the potential to serve as an improvement insofar as the electromagnet-modified 3D printer allows users to control the positioning of multiple OBBs in three dimensions.

Finally, as this bioprinting platform is OBB-agnostic, it can be utilized across a wide range of biological systems wherein signaling from distinct cell types, lineages, and oncogenic potential is relevant. Here, we leverage STAMP to construct multi-region neural assembloids consisting of regionalized constituents of neural circuits and tumor-host assembloids wherein the ratio and positioning of each OBB is controllably varied. Future studies may adopt the platform for investigations into the developmental trajectory of various tissues or etiology of various diseases and, in so doing, mediate the discovery and preclinical validation of therapeutics.

7. Methods

7.1 hiPSC Maintenance

The stemness and differentiation capacity of the human induced pluripotent stem cells (hiPSCs) used in this study were previously validated[52,53]. All hiPSCs were tested for and maintained *mycoplasma* free. In total, 4 hiPSC lines from two distinct donors were included. Approval for this study was obtained from the Stanford IRB, and informed consent was obtained from all donors.

hiPSCs were maintained using standard methods. Briefly, hiPSCs were cultured with mTESR-1 Plus (StemCell Tech) media in monolayer on hESC-qualified Matrigel (Sigma).

7.2 Neural Organoid Differentiation and Maturation

Dorsal and ventral forebrain neural organoids were differentiated in accordance with previously published protocols[2,9,54]. For both brain regions, hiPSCs were dissociated with Accutase (StemCell Tech), aggregated into uniform 5,000 cell aggregates with AggreWell800 plates (StemCell Tech), and allowed to stabilize for 16 hours in mTeSR-1 Plus with ROCK inhibitor Y-27632 (10 μM, StemCell Tech). hiPSC aggregates were then transferred to ultralow-attachment plastic dishes (Corning) with hiPSC media consisting of Essential 6 medium (Gibco) supplemented with penicillin-streptomycin (1:100, Life Technologies).

For dorsal brain region specific organoids, hiPSC media was additionally supplemented with the two dual SMAD inhibitors LDN-193189 (100 nM, Stemgent) and SB-431542 (10 μM, Tocris) and changed daily. On the sixth day in suspension, hiPSC medium was replaced with neural medium consisting of neurobasal-A (Life Technologies), B-27 supplement without vitamin A (1:50, Life Technologies), GlutaMax (1:100, Life Technologies), penicillin-streptomycin (1:100, Life Technologies), and supplemented with human EGF (20 ng ml$^{-1}$, PeproTech) and human FGF-2 (20 ng ml$^{-1}$, PeproTech) through day 24. From day 25 to 42, neural medium was supplemented with the growth factors BDNF (20 ng ml$^{-1}$, PeproTech) and NT3 (20 ng ml$^{-1}$, PeproTech) with medium changes every other day. From day 43 onward, dorsal neural organoids were maintained in neural medium with medium changes every four days.

For ventral brain region specific organoids, hiPSCs were differentiated following the same protocol described for dorsal neural organoids with two important amendments. Firstly, from day 4 to day 24, the WNT pathway inhibitor IWP2 (5 μM, Selleckchem) was added. Secondly, from day 12 to day 24, the SHH pathway agonist SAG (100 nM, Selleckchem) was added.

7.3 MSC and HUVEC Spheroid Culture

Human MSCs (Lonza) were expanded in high-glucose DMEM with GlutaMAX (Thermo Fisher Scientific) supplemented with FBS (1:10, Thermo Fisher Scientific) and penicillin-streptomycin (1:100, Life Technologies).

Human umbilical vein endothelial cells (PromoCell) were expanded in endothelial growth medium-2 (EGM-2 bullet kit, Lonza). To form uniform sized spheroids, MSCs and HUVECs were dissociated, aggregated as either 5,000 or 8,000 cell clusters, respectively, using AggreWell800 plates, and allowed to stabilize for 16 hours. Spheroid formation was confirmed by phase contrast microscopy and maintained with daily media changes.

7.4 DIPG Spheroid Culture

Patient-derived primary cells (SU-DIPG-XIII-FL and SU-DIPG-XIII-P) were provided by the lab of Prof. Michelle Monje-Deisseroth (Stanford University). All human DIPG cell cultures were generated with informed consent and under institutional review board (IRB)-approved protocols, as previously described[34,37,55]. DIPG cells were expanded as tumor neurospheres in tumor stem medium consisting of neurobasal (Life Technologies), B27 supplement without vitamin A (Life Technologies), human EGF (20 ng ml$^{-1}$, Shenandoah Biotech), human b-FGF (20 ng ml$^{-1}$, Shenandoah Biotech), human PDGF-AA (10 ng ml$^{-1}$, Shenandoah Biotech), human PDGF-BB (10 ng ml$^{-1}$, Shenandoah Biotech), and heparin (2 ng ml$^{-1}$, StemCell Tech). Media was changed once per week.

7.5 Organoid and Spheroid Mass, Diameter, and Surface Tension Measurements

The following characterizations were performed similarly for neural organoids, MSC spheroids, and HUVEC spheroids; to simplify the description of the methods, for this section alone, all three structures are broadly referred to as spheroids.

To measure mass, spheroids were manually transferred to an Eppendorf tube containing a small volume of DPBS (Corning) by first pipetting an individual spheroid onto the edge of a metal spatula, manually removing any excess media, then lightly tapping the spheroid to the surface of the DPBS. This process was repeated four additional times such that the Eppendorf tube contained five spheroids. The resultant mass was divided by five to obtain a single, averaged data point. This process was then repeated five times per spheroid type and time point.

To measure diameter, brightfield images were recorded with an epifluorescent microscope (Leica Microsystems, THUNDER Imager 3D Cell Culture) and the diameter was manually traced using ImageJ (NIH, v.2.1.0/1.53c).

To measure surface tension, spheroids were exposed to micropipette aspiration as previously described[13,56,57]. Briefly, a clear, plastic, blunt edge nozzle on a syringe was affixed to a DBPS-containing 35 mm plate. The syringe was connected to a pressure modulator, which was connected to a vacuum line. A range of pressures ($\Delta P=1-30$ mmHg) was applied to the spheroid surface, and the subsequent deformation was observed on an epifluorescent microscope (Leica Microsystems, THUNDER Imager 3D Cell Culture).

7.6 Vacuum Aspiration

Spheroids were exposed to vacuum aspiration pressures following the same protocol described above for surface tension measurements. Importantly, to ensure consistent pressure was applied to a given spheroid, the desired pressure was first reproducibly obtained in DPBS before the blunt edge nozzle was lowered to the surface of the spheroid.

7.7 Neural Organoid Viability

To characterize viability, organoids were submerged in a solution consisting of DPBS supplemented with 2 μM calcein AM and 4 UM ethidium homodimer for 20 min at 37° C. The samples were washed with DPBS and imaged with an epifluorescent microscope (Leica Microsystems, THUNDER Imager 3D Cell Culture) and confocal microscope (Leica SPE).

7.8 MNP Fabrication

Iron oxide magnetic particles were fabricated in-house by the conventional method of co-precipitation, in which ferrous and ferric ions are mixed in a 1:2 molar ratio in a basic solution[58]. Briefly, 0.05 M iron (II) sulfate (Sigma) and 0.1 M iron (III) chloride (Sigma-Aldrich) were first dissolved together in water at room temperature. A solution of 10% ammonium hydroxide was added to the reaction dropwise through a separatory funnel with constant stirring (500 rpm) for one hour. Following the completion of the reaction, the iron oxide particles were washed three times with water.

Commercial iron oxide nanoparticles were purchased from Alpha Nanotech Inc. (size: 300 nm, surface coating: polydopamine coating).

7.9 MNP Size Distribution and Zeta Potential

To determine the hydrodynamic size distribution, dynamic light scattering (DLS) was performed on a 0.1 wt % MNP in DPBS solution using a Malvern Zetasizer Nano ZS. To determine the distribution of aggregate sizes, a 0.1 wt % MNP in DPBS solution was sonicated in a bath sonicator for 5 minutes, sandwiched between two glass slides, imaged with a Leica THUNDER microscope, and processed with FIJI. To determine the zeta potential, a 0.01 wt % MNP in DPBS solution was sonicated in a bath sonicator for 5 minutes, suspended in folded capillary cells (Malvern, DTS1060), and characterized, with 10 runs per sample, in a Malvern Zetasizer Nano ZS.

7.10 MNP Surface Coverage

To quantify organoid surface MNP coverage, brightfield Z-stack images were taken using a Leica THUNDER microscope. Background subtraction was performed using the rolling ball algorithm (radius=25 pixels), and MNP coverage area was measured via thresholding and maximum Z projection.

7.11 Magnetic Field Strength Characterization

To characterize the magnetic field applied during lifting, magnetic field strength measurements were performed as a function of applied voltage and distance from the probe tip using a LATNEX MK-30K AC/DC Gauss meter and electromagnet-modified Prusa i3 MK3S 3D printer.

7.12 CNF Fabrication

Stock solutions of bacterial CNF for the magnetic ink and support scaffold were fabricated from nata de coco (Jubes). The nata de coco cubes were washed with flowing deionized water for two days. Following the washes, coco de nata and deionized water were blended together in a 1:1 ratio until homogenous. The solution was concentrated through centrifugation at 10000 rpm for 20 minutes, autoclaved for sterilization, and stored at 4° C. To calculate the concentration of the CNF stock solution, aliquots were weighed before and after drying. For use in the magnetic ink or support scaffold, the CNF stock was diluted with sterile DPBS.

7.13 CNF Microrheological Characterization

Mechanical testing of the CNF-based magnetic ink and support scaffold formulations was performed using an AR-G2 (TA Instruments) stress-controlled rheometer (8 mm parallel plate geometry with a 1 mm gap) at 25° C. For the storage and loss moduli, frequency sweeps were performed between 0.1 and 100 rad s$^{-1}$ at a strain of 1%, and measurements were confirmed to be within the linear viscoelastic regime. Viscosity tests were performed at shear rates ranging from 0.1 to $10^{s-1}$. For self-healing measurements, alternating strains of 0.1% and 300% were applied.

7.14 Magnetic Lifting

Organoids were coated with 10 μL of a magnetic ink composed of 1 wt % MNPs in 0.025 wt % CNF for 30 minutes. Magnetic rods were affixed to an electromagnet set to 15 V. The rod was then lowered until it was just above the surface of the coated organoid. Once the organoid attached to the rod, the entire construct was moved throughout DPBS to emulate the movement an organoid would experience in the printing process.

7.15 Bioprinting Chip Design and Fabrication

To facilitate automated magnetic bioprinting, we designed a chip which ensured that a series of OBBs were consistently located at a given position. Additional features included an offset platform for medium addition, a row of elongated U-bottom wells, and a raised connector channel between the wells and the reservoir which contained the support scaffold. The chip was created by pouring an uncured mixture of Sylgard 184 (Dow Corning) in 10:1 base to curing agent ratio into a 3D printed polylactic acid mold. The PDMS was degassed under vacuum for 20 minutes and cured at room temperature (RT) for 48 hours before being carefully removed from the mold.

7.16 Automated Magnetic Bioprinting

Automated transfer was achieved using an electromagnet-modified Monoprice MP Select Mini 3D Printer V2 and Kaiweets PS-3010F DC power supply. The printer was modified such that the print-head fan controls were wired, via a solid-state relay, to the power supply which, in turn, activated an electromagnet. As the fan can be turned on or off with G-Code, the electromagnet itself was controllable with the same code that was used to address the movement of the spheroid or organoid.

7.17 Precision of Automated Magnetic Bioprinting

For the measurement of XY localization, alginate beads with diameters comparable to those of neural organoids (1-2 mm) were coated with a magnetic ink composed of 1 wt % MNPs in 0.025 wt % CNF for 30 minutes and transferred from water to a pre-specified location within a 0.5 wt % CNF bath using the magnetic 3D bioprinting approach. FIJI was used to measure the XY deviation of the deposited alginate bead from the marked position.

To measure bioprinting precision in Z, alginate beads were transferred from water into a 0.5 wt % CNF support bath with the magnetic rod. The Z position of the bead was tracked via imaging over 3 days.

7.18 CNF Support Diffusivity Characterization

The diffusivity within the CNF support scaffold was assessed by fluorescent recovery after photobleaching (FRAP) measurements. Briefly, 0.5 wt % CNF was prepared with encapsulated FITC-dextran probes (Sigma) with molecular weights of 10 kDa, 20 kDa, 40 kDa, 70 kDa, 150 kDa, 250 kDa, and 500 kDa. The FRAP experiments were then performed on a confocal microscope (Leica SPE) with 1 min of photobleaching (100 μm×100 μm bleach area, 488 nm laser, 100% intensity) followed by 4 min of capture time (10% intensity). The diffusion coefficients for each probe size were determined using the open-source MATLAB code "frap_analysis" based on the Hankel transform method[59].

7.19 Cellulase-Mediated CNF Scaffold Degradation

For measurements of cellulase-mediated CNF support scaffold degradation, cellulase (Sigma) was dissolved in DMEM/F12 (Gibco) and added atop 0.5 wt % CNF in a 1:4 ratio by volume to approximate the ratio of media to CNF support within the bioprinting chip. All samples were incubated in a humidified 37° C. incubator for three days. Depending on the downstream measurement, cellulase solutions, as well as non-cellulase containing DMEM/F12 controls, were either changed every day or allowed to incubate over the full three days without a media change.

Viscosity and storage moduli were obtained with an AR-G2 (TA Instruments) stress-controlled rheometer (20 mm 1° cone and plate geometry with a 28 μm gap). To observe the effect of cellulase on the viscosity of CNF over 72 hours, samples were loaded onto the stage at 37° C. for a 5 min time sweep with 1% oscillatory strain and 1 rad/s angular frequency. This was followed by a frequency sweep from 0.1 to 100 Hz at 1% strain. To measure the storage modulus, samples were loaded onto the stage at 2 hours, 4 hours, 6 hours, 24 hours, 48 hours, and 72 hours and subjected to a frequency sweep at 1 rad/s angular frequency.

7.20 Cellulase-Mediated Degradation of CNF Surrounding Extracted Neural Organoids To characterize cellulase-mediated CNF degradation after neural organoid release from the support scaffold, neural organoids were first cultured in 0.5 wt % CNF support bath for 1 day and released through diluting the support bath with DPBS. A 0.5 wt % cellulase (Sigma) solution, made up in neural medium, was filtered through a 0.22 μm filter, warmed to 37° C., and added to the organoids with daily medium changes. Organoids were imaged every day with an epifluorescent microscope (Leica Microsystems, THUNDER Imager 3D Cell Culture). The area of residual CNF on the organoid surface was manually measured with ImageJ (NIH, v.2.3.0/1.53q).

7.21 Quantitative Reverse Transcription Polymerase Chain Reaction (qRT-PCR)

mRNA expression was quantified with qRT-PCR. Organoids were suspended in 500 μL of TRIzol reagent (Invitrogen) and disrupted via probe sonication (Heilscher UP50H, 50% amplitude (25 watts), 30 KHz frequency, 0.5 cycle). mRNA was purified by phenol-chloroform extraction with phase lock gels (Quantabio 5PRIME) followed by isopropyl alcohol precipitation. The resultant mRNA was resuspended in nuclease-free water (Thermo Fisher Scientific) and measured via NanoDrop (Thermo Scientific). 100 ng of mRNA was reverse transcribed using a High-Capacity cDNA Reverse Transcription Kit (Applied Biosystems). For qPCR, 6.6 μL of diluted cDNA was mixed with 0.9 μL of a 5 UM forward and reverse primer pair (Integrated DNA Technologies, Table 3) solution and 7.5 μL of Fast SYBR Green Master Mix (Applied Biosystems). Samples were run on a StepOnePlus Real Time PCR System (Applied Biosystems). CT values were calculated using the StepOnePlus software (v.2.3) and analyzed by the ACT method.

7.22 Immunohistochemistry (IHC)

Organoids and assembloids were fixed in 4% PFA for 2 hours at 4° C. They were then washed three times with DPBS, for 15 min each, and transferred to a 30% sucrose solution in DPBS for 24-48 hours at 4° C. Once the organoids or assembloids sank in the sucrose solution, they were embedded in a 1:1 mixture of OCT (Fisher Scientific) and 30% sucrose in DPBS. They were then snap frozen on dry ice and stored at −80° C. A cryostat (Leica) was used to cut 50 μm sections for immunostaining.

Cryosections were washed with DPBS to remove excess OCT, then permeabilized with 0.25% Triton X-100 (Thermo Fisher) in DPBS (DPBS-T) for 1 hour and blocked with 5% goat serum (Gibco), 5% bovine serum albumin (BSA, Sigma), and 0.5% Triton X-100 in DPBS for 3 hours, all at RT. Samples were stained with primary antibodies for GFP, (1:200, Invitrogen a11122), cleaved caspase-3 (1:400, Cell Signaling 9661), and histone H3 mutated K27M (1:400, Abcam ab190631). Primary antibodies were diluted in 2.5% goat serum, 2.5% BSA, and 0.5% Triton X-100 in DPBS and incubated with the samples overnight at 4° C., Next, the samples were washed with DPBS-T (3×30 min, RT) and incubated with secondary antibody Alexa Fluor 488 (1:500, Invitrogen, A-11034) and 4',6-diamidino-2-phenylindole (DAPI, 5 mg/mL stock, 1:2000, Invitrogen) in the same antibody dilution solution overnight at 4° C. Finally, the samples were washed with DPBS-T (3×20 min, RT) and mounted to No. 1 glass cover slips with ProLong Gold Antifade Reagent (Cell Signaling 9071). Stained samples were imaged using a confocal microscope (Leica SPE).

7.23 Image Analysis

Cleaved caspase-3 expression and H3K27M expression were analyzed from maximum projection immunofluorescence images using CellProfiler[60]. Images were cropped such that only the DIPG spheroid area was included in analysis. For each cell, nuclei and H3K27M objects were identified using the "IdentifyPrimaryObjects" command with a "Minimum Cross-Entropy" thresholding method. Cleaved caspase-3 objects were identified using the "IdentifyPrimaryObjects" command with an "Otsu" thresholding method. Overall area of expression was obtained using the "MeasureImageAreaOccupied" command. Cleaved caspase-3 expression and H3K27M expression were normalized by DAPI count and then normalized to the untreated control.

7.24 Statistical Analysis

Statistical analyses for this study were performed using GraphPad Prism v.9.3.1 software. Details of specific statistical methods and p-value results are included within the figure captions and summarized in Table 5. For all studies, ns=not significant (p>0.05), *=p<0.05, =p<0.01, *=p<0.001, ****=p<0.0001.

10. REFERENCES

1 Kelley, K. W. & Pasca, S. P. Human brain organogenesis: Toward a cellular understanding of development and disease. Cell 185, 42-61, doi:10.1016/j.cell.2021.10.003 (2022).

2 Birey, F. et al. Assembly of functionally integrated human forebrain spheroids. Nature 545, 54-59, doi:10.1038/nature22330 (2017).

3 Bagley, J. A., Reumann, D., Bian, S., Levi-Strauss, J. & Knoblich, J. A. Fused cerebral organoids model interactions between brain regions. Nature Methods 14, 743-751, doi:10.1038/nmeth.4304 (2017).

4 Xiang, Y. et al. Fusion of Regionally Specified hPSC-Derived Organoids Models Human Brain Development and Interneuron Migration. Cell Stem Cell 21, 383-398.e387, doi:10.1016/j.stem.2017.07.007 (2017).

5 Miura, Y. et al. Generation of human striatal organoids and cortico-striatal assembloids from human pluripotent stem cells. Nature Biotechnology 38, 1421-1430, doi:10.1038/s41587-020-00763-w (2020).

6 Andersen, J. et al. Generation of Functional Human 3D Cortico-Motor Assembloids. Cell 183, 1913-1929.e1926, doi:10.1016/j.cell.2020.11.017 (2020).

7 Kasai, T. et al. Hypothalamic Contribution to Pituitary Functions Is Recapitulated In Vitro Using 3D-Cultured Human iPS Cells. Cell Reports 30, 18-24.e15, doi:10.1016/j.celrep.2019.12.009 (2020).

8 Fligor, C. M. et al. Extension of retinofugal projections in an assembled model of human pluripotent stem cell-derived organoids. Stem Cell Reports 16, 2228-2241, doi:10.1016/j.stemcr.2021.05.009 (2021).

9 Miura, Y. et al. Engineering brain assembloids to interrogate human neural circuits. Nature Protocols 17, 15-35, doi:10.1038/s41596-021-00632-z (2022).

10 Wolf, K. J., Weiss, J. D., Uzel, S. G. M., Skylar-Scott, M. A. & Lewis, J. A. Biomanufacturing human tissues via organ building blocks. Cell Stem Cell 29, 667-677, doi:10.1016/j.stem.2022.04.012 (2022).

11 Goulart, E. et al. 3D bioprinting of liver spheroids derived from human induced pluripotent stem cells sustain liver function and viability in vitro. Biofabrication 12, 015010, doi:10.1088/1758-5090/ab4a30 (2019).

12 Skylar-Scott, M. A. et al. Biomanufacturing of organ-specific tissues with high cellular density and embedded vascular channels. Science Advances 5, eaaw2459, doi:10.1126/sciadv.aaw2459 (2019).

13 Ayan, B. et al. Aspiration-assisted bioprinting for precise positioning of biologics. Science Advances 6, eaaw5111, doi:10.1126/sciadv.aaw5111 (2020).

14 Daly, A. C., Davidson, M. D. & Burdick, J. A. 3D bioprinting of high cell-density heterogeneous tissue models through spheroid fusion within self-healing hydrogels. Nature Communications 12, 753, doi:10.1038/s41467-021-21029-2 (2021).

15 Ayan, B. et al. Aspiration-assisted freeform bioprinting of pre-fabricated tissue spheroids in a yield-stress gel. Communications Physics 3, 183, doi:10.1038/s42005-020-00449-4 (2020).

16 Kim, M. H., Banerjee, D., Celik, N. & Ozbolat, I. T. Aspiration-assisted freeform bioprinting of mesenchymal stem cell spheroids within alginate microgels. Biofabrication 14, 024103, doi:10.1088/1758-5090/ac4dd8 (2022).

17 Albanese, A. et al. Multiscale 3D phenotyping of human cerebral organoids. Scientific Reports 10, 21487, doi:10.1038/s41598-020-78130-7 (2020).

18 Roth, J. G. et al. Advancing models of neural development with biomaterials. Nature Reviews Neuroscience 22, 593-615, doi:10.1038/s41583-021-00496-y (2021).

19 Wang, Q. et al. Response of MAPK pathway to iron oxide nanoparticles in vitro treatment promotes osteogenic differentiation of hBMSCs. Biomaterials 86, 11-20, doi:10.1016/j.biomaterials.2016.02.004 (2016).

20 Brunel, L. G., Hull, S. M. & Heilshorn, S. C. Engineered assistive materials for 3D bioprinting: support baths and sacrificial inks. Biofabrication 14, 032001, doi:10.1088/1758-5090/ac6bbe (2022).

21 Gefen, A. & Margulies, S. S. Are in vivo and in situ brain tissues mechanically similar? J Biomech 37, 1339-1352, doi:10.1016/j.jbiomech.2003.12.032 (2004).

22 Elkin, B. S., Azeloglu, E. U., Costa, K. D. & Morrison, B., 3rd. Mechanical heterogeneity of the rat hippocampus measured by atomic force microscope indentation. J Neurotrauma 24, 812-822, doi:10.1089/neu.2006.0169 (2007).

23 Budday, S. et al. Rheological characterization of human brain tissue. Acta Biomater 60, 315-329, doi:10.1016/j.actbio.2017.06.024 (2017).

24 Narazaki, G. et al. Biocompatible polymers for scalable production of human neural organoids. bioRxiv, 2022.2003.2018.484949, doi:10.1101/2022.03.18.484949 (2022).

25 Marchín, O. Interneuron dysfunction in psychiatric disorders. Nat Rev Neurosci 13, 107-120, doi:10.1038/nrn3155 (2012).

26 Tuveson, D. & Clevers, H. Cancer modeling meets human organoid technology. Science 364, 952-955, doi:10.1126/science.aaw6985 (2019).

27 LeSavage, B. L., Suhar, R. A., Broguiere, N., Lutolf, M. P. & Heilshorn, S. C. Next-generation cancer organoids. Nat Mater 21, 143-159, doi:10.1038/s41563-021-01057-5 (2022).

28 Fisher, P. G. et al. A clinicopathologic reappraisal of brain stem tumor classification. Cancer 89, 1569-1576, doi:10.1002/1097-0142(20001001)89:7<1569:: AID-CNCR22>3.0.CO; 2-0 (2000).

29 Johung, T. B. & Monje, M. Diffuse Intrinsic Pontine Glioma: New Pathophysiological Insights and Emerging Therapeutic Targets. Curr Neuropharmacol 15, 88-97, doi:10.2174/1570159x14666160509123229 (2017).

30 Sturm, D. et al. Paediatric and adult glioblastoma: multiform (epi) genomic culprits emerge. Nat Rev Cancer 14, 92-107, doi:10.1038/nrc3655 (2014).

31 Jones, C. & Baker, S. J. Unique genetic and epigenetic mechanisms driving paediatric diffuse high-grade glioma. Nat Rev Cancer 14, doi:10.1038/nrc3811 (2014).

32 Lin, G. L. et al. Non-inflammatory tumor microenvironment of diffuse intrinsic pontine glioma. Acta Neuropathologica Communications 6, 51, doi:10.1186/s40478-018-0553-x (2018).

33 Lin, G. L. & Monje, M. A Protocol for Rapid Post-mortem Cell Culture of Diffuse Intrinsic Pontine Glioma (DIPG). J Vis Exp, doi:10.3791/55360 (2017).

34 Grasso, C. S. et al. Functionally defined therapeutic targets in diffuse intrinsic pontine glioma. Nat Med 21, 555-559, doi:10.1038/nm.3855 (2015).

35 Puget, S. et al. Biopsy in a series of 130 pediatric diffuse intrinsic Pontine gliomas. Childs Nerv Syst 31, 1773-1780, doi:10.1007/s00381-015-2832-1 (2015).

36 Lin, G. L. et al. Therapeutic strategies for diffuse midline glioma from high-throughput combination drug screening. Sci Transl Med 11, doi:10.1126/scitranslmed.aaw0064 (2019).

37 Qin, E. Y. et al. Neural Precursor-Derived Pleiotrophin Mediates Subventricular Zone Invasion by Glioma. Cell 170, 845-859.e819, doi:10.1016/j.cell.2017.07.016 (2017).

38 Louis, D. N. et al. The 2016 World Health Organization Classification of Tumors of the Central Nervous System: a summary. Acta Neuropathol 131, 803-820, doi:10.1007/s00401-016-1545-1 (2016).

39 Filbin, M. & Monje, M. Developmental origins and emerging therapeutic opportunities for childhood cancer. Nat Med 25, 367-376, doi:10.1038/s41591-019-0383-9 (2019).

40 Misuraca, K. L., Cordero, F. J. & Becher, O. J. Pre-Clinical Models of Diffuse Intrinsic Pontine Glioma. Front Oncol 5, 172, doi:10.3389/fonc.2015.00172 (2015).

41 Welby, J. P. et al. Current Murine Models and New Developments in H3K27M Diffuse Midline Gliomas. Front Oncol 9, 92, doi:10.3389/fonc.2019.00092 (2019).

42 Wu, G. et al. Somatic histone H3 alterations in pediatric diffuse intrinsic pontine gliomas and non-brainstem glioblastomas. Nat Genet 44, 251-253, doi:10.1038/ng. 1102 (2012).

43 Lewis, P. W. et al. Inhibition of PRC2 activity by a gain-of-function H3 mutation found in pediatric glioblastoma. Science 340, 857-861, doi:10.1126/science. 1232245 (2013).

44 Bender, S. et al. Reduced H3K27me3 and DNA hypomethylation are major drivers of gene expression in K27M mutant pediatric high-grade gliomas. Cancer Cell 24, 660-672, doi:10.1016/j.ccr.2013.10.006 (2013).

45 Chan, K. M. et al. The histone H3.3K27M mutation in pediatric glioma reprograms H3K27 methylation and gene expression. Genes Dev 27, 985-990, doi:10.1101/gad.217778.113 (2013).

46 Funato, K., Major, T., Lewis, P. W., Allis, C. D. & Tabar, V. Use of human embryonic stem cells to model pediatric gliomas with H3.3K27M histone mutation. Science 346, 1529-1533, doi:10.1126/science. 1253799 (2014).

47 Piunti, A. et al. Therapeutic targeting of polycomb and BET bromodomain proteins in diffuse intrinsic pontine gliomas. Nat Med 23, 493-500, doi:10.1038/nm.4296 (2017).

48 Stafford, J. M. et al. Multiple modes of PRC2 inhibition elicit global chromatin alterations in H3K27M pediatric glioma. Sci Adv 4, eaau5935, doi:10.1126/sciadv.aau5935 (2018).

49 Harutyunyan, A. S. et al. H3K27M induces defective chromatin spread of PRC2-mediated repressive H3K27me2/me3 and is essential for glioma tumorigenesis. Nat Commun 10, 1262, doi:10.1038/s41467-019-09140-x (2019).

50 Yang, Q. & Liberali, P. Collective behaviours in organoids. Curr Opin Cell Biol 72, 81-90, doi:10.1016/j.ceb.2021.06.006 (2021).

51 Moldovan, N. I., Hibino, N. & Nakayama, K. Principles of the Kenzan Method for Robotic Cell Spheroid-Based Three-Dimensional Bioprinting<sup/>. Tissue Eng Part B Rev 23, 237-244, doi:10.1089/ten.TEB.2016.0322 (2017).

52 Roth, J. G. et al. 16p11.2 microdeletion imparts transcriptional alterations in human iPSC-derived models of early neural development. Elife 9, doi:10.7554/eLife.58178 (2020).

53 Ang, L. T. et al. Generating human artery and vein cells from pluripotent stem cells highlights the arterial tropism of Nipah and Hendra viruses. Cell 185, 2523-2541.e2530, doi:10.1016/j.cell.2022.05.024 (2022).

54 Yoon, S. J. et al. Reliability of human cortical organoid generation. Nat Methods 16, 75-78, doi:10.1038/s41592-018-0255-0 (2019).

55 Nagaraja, S. et al. Transcriptional Dependencies in Diffuse Intrinsic Pontine Glioma. Cancer Cell 31, 635-652.e636, doi:10.1016/j.ccell.2017.03.011 (2017).

56 Heinrich, V., Leung, A. & Evans, E. Nano- to microscale dynamics of P-selectin detachment from leukocyte interfaces. II. Tether flow terminated by P-selectin dissociation from PSGL-1. Biophys J 88, 2299-2308, doi:10.1529/biophysj. 104.051706 (2005).

57 Guevorkian, K., Colbert, M. J., Durth, M., Dufour, S. & Brochard-Wyart, F. Aspiration of biological viscoelastic drops. Phys Rev Lett 104, 218101, doi:10.1103/PhysRevLett. 104.218101 (2010).

58 Wu, W., He, Q. & Jiang, C. Magnetic iron oxide nanoparticles: synthesis and surface functionalization strategies. Nanoscale Res Lett 3, 397-415, doi:10.1007/s11671-008-9174-9 (2008).

59 Jonsson, P., Jonsson, M. P., Tegenfeldt, J. O. & Hook, F. A method improving the accuracy of fluorescence recovery after photobleaching analysis. Biophys J 95, 5334-5348, doi:10.1529/biophysj. 108.134874 (2008).

60 McQuin, C. et al. CellProfiler 3.0: Next-generation image processing for biology. PLOS Biol 16, e2005970, doi:10.1371/journal.pbio.2005970 (2018).

TABLE 1

| | | | | | | |
|---|---|---|---|---|---|---|
| Previous demonstrations of AAB. | | | | | | |
| Cell Type | Spheroid Size (μm) | Vacuum Pressure (mmHg) | Nozzle Diameter (μm) | Support Type | Dimensionality | Reference |
| MSC, HUVEC, 3T3, 4T1, HDF | 200-600 | 20-60 | 250 | Agarose | 2D | Ayan, Ozbolat et al. *Sci. Adv.* 2020. |
| MSC | 150-400 | 20-300 | 150 | Carbopol | 3D | Ayan, Ozbolat et al. *Commun. Phys.* 2020. |
| MSC | 250-600 | 70 | 200 | Alginate | 3D | Kim, Ozbolat et al. *Biofabrication.* 2022. |
| MSC, hiPSC-CM | 200-400 | Not described | 100 | Hyaluronan | 3D | Daly, Burdick et al. *Nat. Commun.* 2021. |

Abbreviations: Aspiration-assisted bioprinting (AAB), Mesenchymal stromal cells (MSC), Human umbilical vein endothelial cells (HUVEC), NIH/3T3 murine embryonic fibroblasts (3T3), Murine breast cancer cell line derived from mammary gland (4T1), Human dermal fibroblasts (HDF), Human induced pluripotent stem cell-derived cardiomyocytes (hiPSC-CM).

TABLE 2

| | Characterization of MNPs. | |
|---|---|---|
| | Homemade (mean ± SD) | Commercial (mean ± SD) |
| Zeta Potential (mV) | −22.26 ± 1.342 | 49.50 ± 5.920 * |
| Aggregate Diameter (nm) | 2864 ± 4438 | 2545 ± 1926 |
| Hydrodynamic Diameter (nm) | 1003 ± 49.3 | 669.8 ± 41.0 |

Magnetic nanoparticles (MNPs)
* These values provided by Alpha Nanotech

TABLE 3

| Fluorescence recovery after photobleaching of 0.5 wt % CNF across MWs. | | |
|---|---|---|
| Diffusant MW (Da) | Hydrodynamic Radius (nm) | Diffusivity (um^2 s^-1) |
| 10,000 | 2.3 | 130 ± 9 |
| 20,000 | 3.3 | 105 ± 2 |
| 40,000 | 4.5 | 82 ± 2 |
| 70,000 | 6.0 | 85 ± 3 |
| 150,000 | 8.5 | 82 ± 2 |
| 250,000 | 10.6 | 63 ± 2 |
| 500,000 | 14.7 | 39 ± 1 |

Abbreviations:
Percent by weight (wt %)
Cellulose nanofiber (CNF)
Molecular weight (MW)

TABLE 4

| | Primer sequences. | |
|---|---|---|
| Target | Forward Primer (5' to 3') | Reverse Primer (5' to 3') |
| FGFR1 | CGTGGCCTTGACCTCCAACC (SEQ ID NO: 1) | GTCCGCCATTGGCAAGCTGG (SEQ ID NO: 2) |
| GAPDH | CATGAGAAGTATGACAACA GCCT (SEQ ID NO: 3) | AGTCCTTCCACGATACCA AAGT (SEQ ID NO: 4) |
| KRAS | GTCATGAACTGTACTACTCC (SEQ ID NO: 5) | GGATACTTCTAACAAGCTGC (SEQ ID NO: 6) |
| MAP2K2 | GTCACGGGATGGATAGCCGG (SEQ ID NO: 7) | CTCGGACCGCTTGATGAAGG (SEQ ID NO: 8) |
| MAP3K8 | CCTCACGACCACCTCATGAG (SEQ ID NO: 9) | CACATGGTCATTAGACTGGG (SEQ ID NO: 10) |
| RPS6KA1 | CCACCAGGACCTACAGCTTG (SEQ ID NO: 11) | CCTGTGGCCCGAATGCCCTG (SEQ ID NO: 12) |
| RPS6KA3 | CTTCAAGGTATTGCCATTCC (SEQ ID NO: 13) | CCCCATTCCCACCCATGACC (SEQ ID NO: 14) |

What is claimed is:

1. A bioprinter for producing a multi-spheroid tissue, the bioprinter comprising:

a plurality of microwells, wherein the microwells can be used for generating and culturing a plurality of spheroids;

a reservoir comprising a support scaffold;

a dual printhead comprising a first nozzle and a second nozzle, wherein the first nozzle comprises an extrusion channel, and the second nozzle is coupled to an electromagnet, wherein the electromagnet is connected to a rod that becomes magnetized when the electromagnet is turned on and demagnetized when the electromagnet is turned off;

a container containing magnetic ink comprising magnetic particles, wherein the container is connected to the extrusion channel to allow the first nozzle to deposit the magnetic ink;

a processor, wherein the processor is programmed to perform steps comprising:

(i) locating a microwell that contains a selected spheroid;

(ii) moving the dual printhead to a position over the microwell that contains the selected spheroid;

(iii) instructing the first nozzle to deposit the magnetic ink in the microwell containing the selected spheroid, wherein the selected spheroid is coated with the magnetic ink;

(iv) turning on the electromagnet, wherein the rod becomes magnetized;

(v) lowering the magnetized rod over the selected spheroid until the magnetized rod magnetically attaches to the magnetic particles of the magnetic ink coating the selected spheroid;

(vi) raising the magnetized rod, wherein the selected spheroid is lifted out of the microwell;

(vii) moving the magnetized rod carrying the selected spheroid to a selected position in the reservoir;

(viii) lowering the magnetized rod over a selected location in the support scaffold;

(ix) turning off the electromagnet to demagnetize the rod, wherein the selected spheroid detaches from the demagnetized rod and is deposited at the selected location in the support scaffold; and (x) repeating (i)-(ix), wherein additional selected spheroids are coated with the magnetic ink, lifted from the plurality of microwells with the magnetized rod, moved to the reservoir, and detached from the demagnetized rod and deposited at selected locations in the support scaffold to provide spatial control of the fusion of the plurality of spheroids to produce the multi-spheroid tissue.

2. The bioprinter of claim 1, wherein the rod comprises a ferromagnetic metal.

3. The bioprinter of claim 2, wherein the ferromagnetic metal is iron.

4. The bioprinter of claim 1, wherein the magnetic ink comprises iron oxide magnetic particles.

5. The bioprinter of claim 1, wherein the magnetic ink comprises magnetic particles embedded in a cytocompatible hydrogel.

6. The bioprinter of claim 5, wherein the hydrogel comprises a cellulose nanofiber (CNF).

7. The bioprinter of claim 6, wherein the hydrogel comprises 0.025 percent by weight (wt %) to 0.10 wt % CNF.

8. The bioprinter of claim 1, wherein the magnetic particles are magnetic nanoparticles.

9. The bioprinter of claim 8, wherein the magnetic ink comprises at least 1 wt % magnetic nanoparticles.

10. The bioprinter of claim 1, wherein the support scaffold comprises a cytocompatible hydrogel.

11. The bioprinter of claim 10, wherein the hydrogel of the support scaffold comprises 0.4 wt % to 0.6 wt % CNF.

12. The bioprinter of claim 1, wherein the processor is further programmed to instruct the bioprinter to add cellulase to the support scaffold after step (x), wherein the support scaffold is removed from the multi-spheroid tissue.

13. The bioprinter of claim 1, wherein voltage of the electromagnet and distance of the magnetic rod from the selected spheroid can be adjusted to control magnetic field strength surrounding the selected spheroid.

14. The bioprinter of claim 1, further comprising:

a pump;

a multiway selector valve, wherein the multiway selector valve is interfaced with the pump; and a media ramp comprising one or more containers or wells comprising one or more types of media, wherein the one or more containers or wells are fluidically connected to the multiway selector valve such that a user can select a medium from the one or more types of media for distribution to one or more selected microwells.

15. The bioprinter of claim 14, further comprising a container or well comprising cellulase, wherein the container or well comprising cellulase is fluidically connected to the multiway selector valve such that the user can select cellulase to add to one or more selected microwells.

16. The bioprinter of claim 1, further comprising a chip, wherein the plurality of microwells and the reservoir comprising the support scaffold are contained on the chip, wherein the plurality of microwells is arranged linearly in rows, where each row of microwells is fluidically connected to an inlet;

wherein for each row of microwells, the inlet further comprises a syringe alignment pad located at a first end of the row of microwells;

wherein for each row of microwells, the chip further comprises an offset platform for medium addition to the microwells, wherein the offset platform for medium addition to the microwells is located between the syringe alignment pad and the row of microwells; and wherein for each row of microwells, the chip further comprises a raised connector channel located between the microwells and the reservoir comprising the support scaffold.

17. The bioprinter of claim 16, wherein the chip further comprises a plurality of reservoirs comprising support scaffolds, wherein for each row of microwells, the syringe alignment pad is located at the first end of the row of microwells and one of the reservoirs of the plurality is located at the second end of the row of microwells, wherein each reservoir further comprises an inlet fluidically connected to the reservoir.

18. The bioprinter of claim 1, further comprising a temperature controller that maintains the microwells and the reservoir at a suitable temperature for culturing the plurality of spheroids and the multi-spheroid tissue.

19. The bioprinter of claim 1, further comprising a power source, wherein the power source controls a voltage applied to the electromagnet and the strength of the magnetic force used to lift the spheroids.

20. The bioprinter of claim 1, wherein the bioprinter comprises multiple dual printheads.

21. A method of using the bioprinter of claim 1 to produce a multi-spheroid tissue, the method comprising:

(a) adding cells to the plurality of microwells, (b) adding spheroid-specific media to the plurality of microwells;

(c) culturing the cells under suitable conditions, wherein the plurality of spheroids is generated from the cells;

(d) instructing the processor to perform the steps comprising:

(i) locating a microwell that contains a selected spheroid;

(ii) moving the dual printhead to a position over the microwell that contains the selected spheroid;

(iii) instructing the first nozzle to deposit the magnetic ink in the microwell containing the selected spheroid, wherein the selected spheroid is coated with the magnetic ink;

(iv) turning on the electromagnet, wherein the rod becomes magnetized;

(v) lowering the magnetized rod over the selected spheroid until the magnetized rod magnetically attaches to the magnetic particles of the magnetic ink coating the selected spheroid;

(vi) raising the magnetized rod, wherein the selected spheroid is lifted out of the microwell;

(vii) moving the magnetized rod carrying the selected spheroid to a selected position in the reservoir;

(viii) lowering the magnetized rod over a selected location in the support scaffold;

(ix) turning off the electromagnet to demagnetize the rod, wherein the selected spheroid detaches from the demagnetized rod and is deposited at the selected location in the support scaffold; and (x) repeating (i)-(ix), wherein additional selected spheroids are coated with the magnetic ink, lifted from the plurality of microwells with the magnetized rod, moved to the reservoir, and detached from the demagnetized rod and deposited at selected locations in the support scaffold; and (e) culturing the plurality of spheroids within the support scaffold under conditions suitable for growth of the spheroids, wherein fusion of the plurality of spheroids results in generation of the multi-spheroid tissue.

22. The method of claim 21, further comprising removing the support scaffold from the multi-spheroid tissue.

23. The method of claim 21, further comprising adjusting voltage of the electromagnet and distance of the magnetic rod from the selected spheroid to control magnetic field strength surrounding the selected spheroid.

24. The method of claim 23, wherein the bioprinter comprises multiple dual printheads, and wherein multiple coated spheroids are lifted and positioned in the support scaffold simultaneously.

\* \* \* \* \*

SEQUENCE LISTING

```
Sequence total quantity: 14
SEQ ID NO: 1            moltype = DNA   length = 20
FEATURE                Location/Qualifiers
source                 1..20
                       mol_type = other DNA
                       organism = synthetic construct
SEQUENCE: 1
cgtggccttg acctccaacc                                         20

SEQ ID NO: 2            moltype = DNA   length = 20
FEATURE                Location/Qualifiers
source                 1..20
                       mol_type = other DNA
                       organism = synthetic construct
SEQUENCE: 2
gtccgccatt ggcaagctgg                                         20

SEQ ID NO: 3            moltype = DNA   length = 23
FEATURE                Location/Qualifiers
source                 1..23
                       mol_type = other DNA
                       organism = synthetic construct
SEQUENCE: 3
catgagaagt atgacaacag cct                                     23

SEQ ID NO: 4            moltype = DNA   length = 22
FEATURE                Location/Qualifiers
source                 1..22
                       mol_type = other DNA
                       organism = synthetic construct
SEQUENCE: 4
agtccttcca cgataccaaa gt                                      22

SEQ ID NO: 5            moltype = DNA   length = 20
FEATURE                Location/Qualifiers
source                 1..20
                       mol_type = other DNA
                       organism = synthetic construct
SEQUENCE: 5
gtcatgaact gtactactcc                                         20
```

-continued

```
SEQ ID NO: 6              moltype = DNA  length = 20
FEATURE                   Location/Qualifiers
source                    1..20
                          mol_type = other DNA
                          organism = synthetic construct
SEQUENCE: 6
ggatacttct aacaagctgc                                              20

SEQ ID NO: 7              moltype = DNA  length = 20
FEATURE                   Location/Qualifiers
source                    1..20
                          mol_type = other DNA
                          organism = synthetic construct
SEQUENCE: 7
gtcacgggat ggatagccgg                                              20

SEQ ID NO: 8              moltype = DNA  length = 20
FEATURE                   Location/Qualifiers
source                    1..20
                          mol_type = other DNA
                          organism = synthetic construct
SEQUENCE: 8
ctcggaccgc ttgatgaagg                                              20

SEQ ID NO: 9              moltype = DNA  length = 20
FEATURE                   Location/Qualifiers
source                    1..20
                          mol_type = other DNA
                          organism = synthetic construct
SEQUENCE: 9
cctcacgacc acctcatgag                                              20

SEQ ID NO: 10             moltype = DNA  length = 20
FEATURE                   Location/Qualifiers
source                    1..20
                          mol_type = other DNA
                          organism = synthetic construct
SEQUENCE: 10
cacatggtca ttagactggg                                              20

SEQ ID NO: 11             moltype = DNA  length = 20
FEATURE                   Location/Qualifiers
source                    1..20
                          mol_type = other DNA
                          organism = synthetic construct
SEQUENCE: 11
ccaccaggac ctacagcttg                                              20

SEQ ID NO: 12             moltype = DNA  length = 20
FEATURE                   Location/Qualifiers
source                    1..20
                          mol_type = other DNA
                          organism = synthetic construct
SEQUENCE: 12
cctgtggccc gaatgccctg                                              20

SEQ ID NO: 13             moltype = DNA  length = 20
FEATURE                   Location/Qualifiers
source                    1..20
                          mol_type = other DNA
                          organism = synthetic construct
SEQUENCE: 13
cttcaaggta ttgccattcc                                              20

SEQ ID NO: 14             moltype = DNA  length = 20
FEATURE                   Location/Qualifiers
source                    1..20
                          mol_type = other DNA
                          organism = synthetic construct
SEQUENCE: 14
ccccattccc acccatgacc                                              20
```